US007348418B2

(12) United States Patent
Singh et al.

(10) Patent No.: US 7,348,418 B2
(45) Date of Patent: Mar. 25, 2008

(54) CARCINOMA-RELATED GENES AND POLYPEPTIDES AND METHODS OF USE THEREOF

(75) Inventors: Bhuvanesh Singh, New York, NY (US); Pabbathi Gopal Reddy, deceased, late of Gangadhara Mandal (IN); by Pabbathi Thirumal Reddy, legal representative, Gangadhara Mandal (IN)

(73) Assignee: Memorial Sloan-Kettering Cancer Center, New York, NY (US)

( * ) Notice: Subject to any disclaimer, the term of this patent is extended or adjusted under 35 U.S.C. 154(b) by 177 days.

(21) Appl. No.: 10/361,725

(22) Filed: Feb. 10, 2003

(65) Prior Publication Data

US 2004/0009541 A1 Jan. 15, 2004

Related U.S. Application Data

(60) Provisional application No. 60/355,009, filed on Feb. 8, 2002.

(51) Int. Cl.
| | |
|---|---|
| C07H 21/02 | (2006.01) |
| C07H 21/04 | (2006.01) |
| C12P 21/06 | (2006.01) |
| C12N 5/00 | (2006.01) |
| C12N 5/02 | (2006.01) |

(52) U.S. Cl. .................... 536/23.1; 435/325; 435/69.1
(58) Field of Classification Search ................ 530/350, 530/300
See application file for complete search history.

(56) References Cited

U.S. PATENT DOCUMENTS

| 5,928,884 A * | 7/1999 | Croce et al. ............... 435/7.23 |
| 2002/0164666 A1 * | 11/2002 | Cimbora et al. ........... 435/7.23 |

OTHER PUBLICATIONS

Mas C, Bourgeois F, Bulfone A, Levacher B, Mugnier C, Simonneau M. Cloning and expression analysis of a novel gene, RP42, mapping to an autism susceptibility locus on 6q16. Genomics. Apr. 1, 2000;65(1):70-4.*
New England Biolabs, Catalog Apr. 1993, #1230, Random Primer.*
Eck et al., (Gene-Based Therapy, In: The Pharmacological Basis of Therapeutics, Goodman and Gilman, Ed.s, 1996, pp. 77-101.*
Verma I and Somia N, Nature, 1997, vol. 389, pp. 239-242.*
Orkin et al., Report and Recommendation of the Panel to Assess the NIH Investment in Research on Gene Therapy, NIH, 1995.*
All the references cited in this action have been provided in the previous office actions.*
Reddy,P.G. and Singh,B.; GenBank Acc. No. AF456426; *Homo sapiens* leucine zipper protein (SCRO) mRNA, complete cds; (released to the public as of Feb. 19, 2002).
Mas,C., Bourgeois,F., Bulfone,A., Levacher,B., Mugnier,C. and Simmoneau,M.; GenBank Acc. No. NP 065691; RP42 homolog; squamous cell carcinoma-related oncogene [*Homo sapiens*]; (Genomics 65 (1), 70-74 (2000)).
Pourcel, C., Jaubert, J., Hadchouel, M., Wu, X. and Schweizer, J.; GenBank Acc. No. Np 296372; testis derived transcript 3 [*Mus musculus*]; (Gene (2000) 249 (1-2), 105-113).
Gao,E., Wang,Y., Alcorn,J.L. and Mendelson,C.R.; GenBank Acc. No. AF003894; *Oryctolagus cuniculus* upstream stimulatory factor 1a mRNA, complete cds; Sep. 12, 1997.
Kaminker,J.S., Bergman,C.M., Kronmiller,B., Carlson,J., Svirskas,R., Patel,S., Frise,E., Wheeler,D.A., Lewis,S.E., Rubin,G.M., Ashburner,M. and Celniker,S.E.; GenBank Acc. No. NP 648777; CG7427-PA [*Drosophila melanogaster*]; (*Genome Biol.* (2002) 3 (12), Research0084).
Bjorkqvist, A.M. et al.; DNA Gains in 31 Occur Frequently in Squamous Cell Carcinoma of the Lung, But Not in Adenocarcinoma; *Genes Chromosomes Cancer* (1998) 22, 79-82).
Boukamp P. et al.; Normal Keratinization in a Spontaneously Immortalized Aneuploid Human Keratinocyte Cell Line; *J. Cell Biol.* (1988) 106, 761-771.
Heselmeyer K., et al.; Gain of chromosome 3q defines the transition from severe dysplasia to invasive carcinoma of the uterine cervix; *Proc Natl Acad Sci U S A* (1996) 93:479-484.
Heselmeyer K, et al.; Advanced-Stage Cervical Carcinomas Are Defined by a Recurrent Pattern of Chromosomal Aberrations Revealing Hig Genetic Instability and a Consistent Gain of Chromosome Arm 3q; *Genes Chromosomes Cancer*, (1997) 19:233-240.
Lockhart, D.J. et al.; Expression monitoring by hybridization to high-density oligonucleotide arrays; *Nat Biotechnol* (1996) 14, 1675-1680.
Mahoney, MG et al.; Metastasis-associated protein ((MTA)I enhances migration, invasion, and anchorage-independent survival of immortalized human keratinocytes; *Oncogene* (2002) 21, 2161-2170.
Morrison, T.B. et al.; Quantification of Low-Copy Transcripts by Continuous SYBR Green I Monitoring during Amplification; *Biotechniques* (1998) 24, 954-962.
Motoyama, J. et al.; Essential function of *Gli 2* and *Gli3* in the formation of lung, trachea and oesophagus; *Nat Genet* (1998) 20, 54-57.
O-Charoenrat, P. et al.; Epidermal Growth Factor-like Ligands Differentially Up-Regulate Matrix Metalloproteinase 9 in Head and Neck Squamous Carcinoma Cells;*Cancer Res* (2000) 60, 1121-1128.
Park, H.L. et al.; Mouse *Gli1* mutants are viable but have defects in SHH signaling in combination with a *Gli2* mutation; *Development* (2000) 127, 1593-1605.

(Continued)

*Primary Examiner*—Shanon Foley
*Assistant Examiner*—Lei Yao
(74) *Attorney, Agent, or Firm*—Proteus Patent Practice LLC; Henry E. Auer

(57) ABSTRACT

Novel nucleic acids and polypeptides encoded thereby are provided that are highly duplicated and overexpressed in squamous cell carcinomas of a variety of tissues. Antibodies specific for binding the novel polypeptides are also provided. The invention further discloses several assays for gene duplication and overexpression of the novel gene and excessive production of the novel polypeptide in a sample. These assays permit assessing copy number in a sample from a subject, and contribute to the diagnosis, prognosis and development of therapeutic strategy for a pathology such as squamous cell carcinoma in a subject.

11 Claims, 10 Drawing Sheets

OTHER PUBLICATIONS

Pfaffl, M.W.; A new mathematical model for relative quantification in real-time RT—PCR; *Nucleic Acids Res* (2001) 29, E45-E45.

Schmittgen, T.D. and Zakrajsek, B.A.; Effect of experimental treatment on housekeeping gene expression: validation by real-time, quantitative RT-PCR; *J Biochem Biophys Methods* (2000) 46, 69-81.

Singh, B. et al.; Molecular Cytogenetic Characterization of Head and Neck Squamous Cell Carcinoma and Refinement of 3q Amplification; *Cancer Res* (2001) 61, 4506-4513.

Singh et al.; Spectral Karyotyping Analysis of Head and Neck Squamous Cell Carcinoma; *Laryngoscope* (2001) 111 : 1545-1550.

Singh et al.; p53 regulates cell survival by inhibiting PIK3CA in squamous cell carcinomas; *Genes Dev* (2002) 16:984-993.

Studer, L. et al.; Enhanced Proliferation, Survival, and Dopaminergic Differentiation Of CNS Precursors in Lowered Oxygen. *J Neurosci* (2000) 20, 7377-7383.

Upstate Biotechnology; pUSEamp(+) (empty expression vector) 5.4 kb; Upstate Group, Inc., Lake Placid, NY, 2001.

Weiner, J.A., et al.; E-box-binding Repressor Is Down-regulated in Hepatic Stellates Cells during Up-regulation of Mannose 6-Phosphate/Insulin-like Growth Factor-II Receptor Expression in Early Hepatic Fibrogenesis; *J Biol Chem* (1998) 273, 15913-15919.

* cited by examiner

Figure 1a

```
  1  cgccgtccattcgctgcggagccggaggaggagggagaggcctggaggacaccaacatgaacaagttga
                                                              M  N  K  L      4

71  aatcatcgcagaaggataaagttcgtcagtttatgatcttcacacaatctagtgaaaaaacagcagtaag
      K  S  S  Q  K  D  K  V  R  Q  F  M  I  F  T  Q  S  S  E  K  T  A  V  S  28

141  ttgtcttctcaaaatgactggaagttagatgttgcaacagataatttttccaaaatcctgaactttat
      C  L  S  Q  N  D  W  K  L  D  V  A  T  D  N  F  F  Q  N  P  E  L  Y    51

211  atacgagagagtgtaaaaggatcattggacaggaagaagttagaacagctgtacaatagatacaaagacc
      I  R  E  S  V  K  G  S  L  D  R  K  K  L  E  Q  L  Y  N  R  Y  K  D    74

281  ctcaagatgagaataaaattggaatagatggcatacagcagttctgtgatgacctggcactcgatccagc
      P  Q  D  E  N  K  I  G  I  D  G  I  Q  Q  F  C  D  D  L  A  L  D  P  A  98

351  cagcattagtgtgttgattattgcatggaagttcagagcagcaacacagtgcgagttctccaaacaggag
      S  I  S  V  L  I  I  A  W  K  F  R  A  A  T  Q  C  E  F  S  K  Q  E   121

421  ttcatggatggcatgacagaattaggatgtgacagcatagaaaaactaaaggcccagataccaagatgg
      F  M  D  G  M  T  E  L  G  C  D  S  I  E  R  L  K  A  Q  I  P  K  M   144

491  aacaagaattgaaagaaccaggacgatttaaggatttttaccagtttacttttaattttgcaaagaatcc
      E  Q  E  L  K  E  P  G  R  F  K  D  F  Y  Q  F  T  F  N  F  A  K  N  P 168

561  aggacaaaaaggattagatctagaaatggccattgcctactggaacttagtccttaatggaagatttaaa
      G  Q  K  G  L  D  L  E  M  A  I  A  Y  W  N  L  V  L  N  G  R  F  K   191

631  ttcttagacttatggaataaattttttgttggaacatcataaacgatcaataccaaaagacacttggaatc
      F  L  D  L  W  N  K  F  L  L  E  H  H  K  R  S  I  P  K  D  T  W  N   214

701  ttcttttagacttcagtacgatgattgcagatgacatgtctaattatgatgaagaaggagcatggcctgt
      L  L  L  D  F  S  T  M  I  A  D  D  M  S  N  Y  D  E  E  G  A  W  P  V 238

771  tcttattgatgactttgtggaatttgcacgccctcaaattgctgggacaaaaagtacaacagtgtagcac
      L  I  D  D  F  V  E  F  A  R  P  Q  I  A  G  T  K  S  T  T  V         259

841  taaaggaaccttctagaatgtacatagtctgtacaataaatacaacagaaaattgcacagtcaatttctg
911  ctggctgg
```

Figure 1b

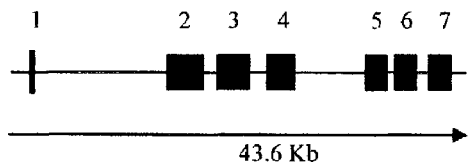

43.6 Kb

Figure 1c gi 187006561 SCCRO [H. sapiens]

gi 10190678 RP42 homolog [H. sapiens]

gi 15826860 Tes3 [M. musculus]

gi 2197096 [A. gambiae]

gi 24664675 CG7427-PA [D. melanogaster]

gi 18399737 Expressed protein [A. thaliana]

gi 25395686 H38K22.2 [C. elegans]

Figure 5.a
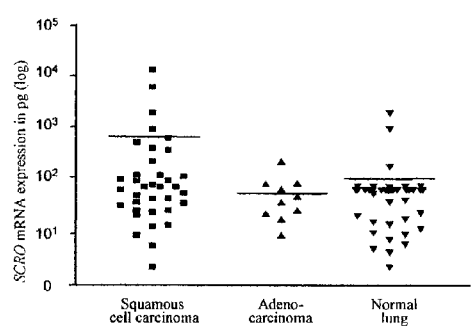
Figure 5.b
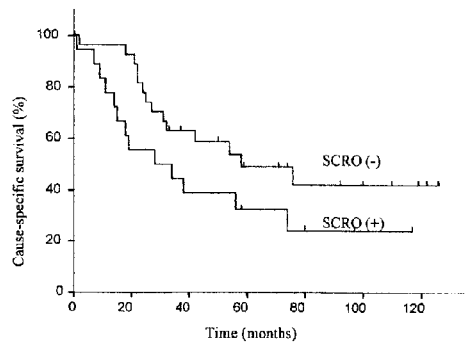
Figure 6
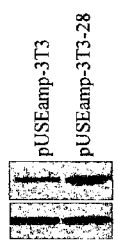
Figure 7
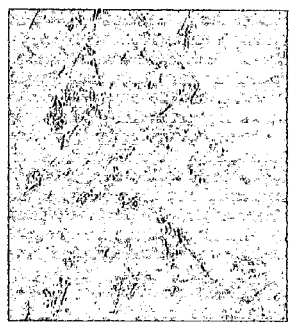 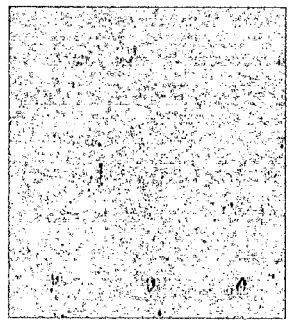
pUSEamp-3T3    pUSEamp-SCRO-3T3

Figure 8.a
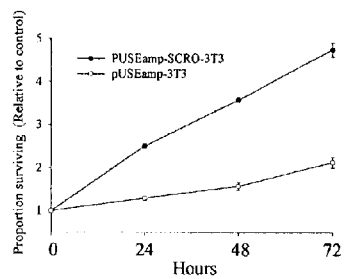
Figure 8.b
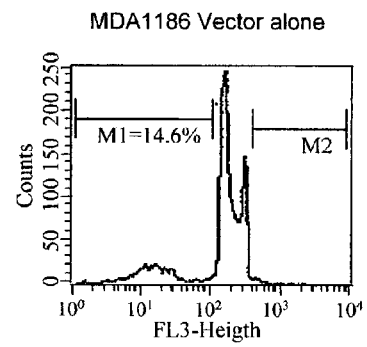
Figure 8.c
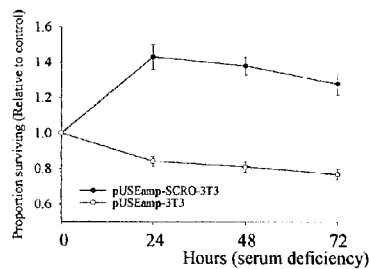
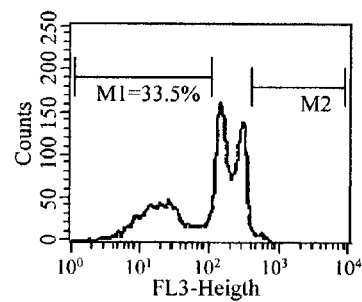
Figure 9.a
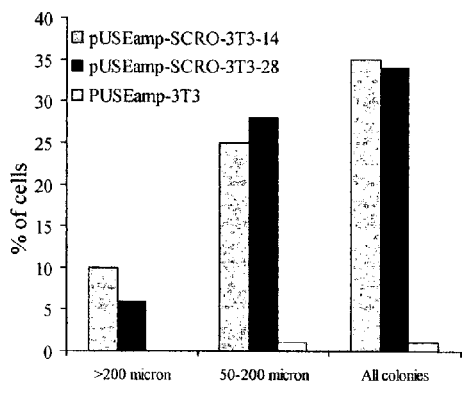
Figure 9.b
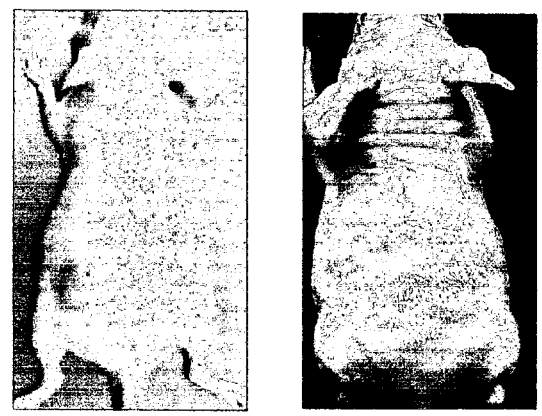
NIH3T3/pUSEamp-SCRO        NIH3T3/pUSEamp

SEQUENCE LISTING

```
<160> NUMBER OF SEQ ID NOS: 29

<210> SEQ ID NO 1
<211> LENGTH: 918
<212> TYPE: DNA
<213> ORGANISM: Homo sapiens
<220> FEATURE:
<221> NAME/KEY: CDS
<222> LOCATION: (58)...(837)

<400> SEQUENCE: 1
cgccgtccat tcgctgcgga gccggaggag gaggggagag gcctggagga caccaac atg      60
                                                                 Met
                                                                  1 aac aag ttg aaa tca tcg cag aag gat aaa gtt cgt cag ttt atg atc       108
Asn Lys Leu Lys Ser Ser Gln Lys Asp Lys Val Arg Gln Phe Met Ile
          5                  10                  15 ttc aca caa tct agt gaa aaa aca gca gta agt tgt ctt tct caa aat       156
Phe Thr Gln Ser Ser Glu Lys Thr Ala Val Ser Cys Leu Ser Gln Asn
     20                  25                  30 gac tgg aag tta gat gtt gca aca gat aat ttt ttc caa aat cct gaa       204
Asp Trp Lys Leu Asp Val Ala Thr Asp Asn Phe Phe Gln Asn Pro Glu
 35                  40                  45 ctt tat ata cga gag agt gta aaa gga tca ttg gac agg aag aag tta       252
Leu Tyr Ile Arg Glu Ser Val Lys Gly Ser Leu Asp Arg Lys Lys Leu
 50                  55                  60                  65 gaa cag ctg tac aat aga tac aaa gac cct caa gat gag aat aaa att       300
Glu Gln Leu Tyr Asn Arg Tyr Lys Asp Pro Gln Asp Glu Asn Lys Ile
                 70                  75                  80
```

```
gga ata gat ggc ata cag cag ttc tgt gat gac ctg gca ctc gat cca      348
Gly Ile Asp Gly Ile Gln Gln Phe Cys Asp Asp Leu Ala Leu Asp Pro
            85                  90                  95 gcc agc att agt gtg ttg att att gca tgg aag ttc aga gca gca aca      396
Ala Ser Ile Ser Val Leu Ile Ile Ala Trp Lys Phe Arg Ala Ala Thr
        100                 105                 110 cag tgc gag ttc tcc aaa cag gag ttc atg gat ggc atg aca gaa tta      444
Gln Cys Glu Phe Ser Lys Gln Glu Phe Met Asp Gly Met Thr Glu Leu
    115                 120                 125 gga tgt gac agc ata gaa aaa cta aag gcc cag ata ccc aag atg gaa      492
Gly Cys Asp Ser Ile Glu Lys Leu Lys Ala Gln Ile Pro Lys Met Glu
130                 135                 140                 145 caa gaa ttg aaa gaa cca gga cga ttt aag gat ttt tac cag ttt act      540
Gln Glu Leu Lys Glu Pro Gly Arg Phe Lys Asp Phe Tyr Gln Phe Thr
                150                 155                 160 ttt aat ttt gca aag aat cca gga caa aaa gga tta gat cta gaa atg      588
Phe Asn Phe Ala Lys Asn Pro Gly Gln Lys Gly Leu Asp Leu Glu Met
        165                 170                 175 gcc att gcc tac tgg aac tta gtg ctt aat gga aga ttt aaa ttc tta      636
Ala Ile Ala Tyr Trp Asn Leu Val Leu Asn Gly Arg Phe Lys Phe Leu
    180                 185                 190 gac tta tgg aat aaa ttt ttg ttg gaa cat cat aaa cga tca ata cca      684
Asp Leu Trp Asn Lys Phe Leu Leu Glu His His Lys Arg Ser Ile Pro
195                 200                 205 aaa gac act tgg aat ctt ctt tta gac ttc agt acg atg att gca gat      732
Lys Asp Thr Trp Asn Leu Leu Leu Asp Phe Ser Thr Met Ile Ala Asp
210                 215                 220                 225 gac atg tct aat tat gat gaa gaa gga gca tgg cct gtt ctt att gat      780
Asp Met Ser Asn Tyr Asp Glu Glu Gly Ala Trp Pro Val Leu Ile Asp
                230                 235                 240 gac ttt gtg gaa ttt gca cgc cct caa att gct ggg aca aaa agt aca      828
Asp Phe Val Glu Phe Ala Arg Pro Gln Ile Ala Gly Thr Lys Ser Thr
        245                 250                 255 aca gtg tag cactaaagga accttctaga atgtacatag tctgtacaat              877
Thr Val * aaatacaaca gaaaattgca cagtcaattt ctgctggctg g                        918

<210> SEQ ID NO 2
<211> LENGTH: 259
<212> TYPE: PRT
<213> ORGANISM: Homo sapiens

<400> SEQUENCE: 2

Met Asn Lys Leu Lys Ser Ser Gln Lys Asp Lys Val Arg Gln Phe Met
 1               5                  10                  15

Ile Phe Thr Gln Ser Ser Glu Lys Thr Ala Val Ser Cys Leu Ser Gln
            20                  25                  30

Asn Asp Trp Lys Leu Asp Val Ala Thr Asp Asn Phe Phe Gln Asn Pro
        35                  40                  45

Glu Leu Tyr Ile Arg Glu Ser Val Lys Gly Ser Leu Asp Arg Lys Lys
    50                  55                  60

Leu Glu Gln Leu Tyr Asn Arg Tyr Lys Asp Pro Gln Asp Glu Asn Lys
65                  70                  75                  80

Ile Gly Ile Asp Gly Ile Gln Gln Phe Cys Asp Asp Leu Ala Leu Asp
                85                  90                  95

Pro Ala Ser Ile Ser Val Leu Ile Ile Ala Trp Lys Phe Arg Ala Ala
            100                 105                 110
```

-continued

```
Thr Gln Cys Glu Phe Ser Lys Gln Glu Phe Met Asp Gly Met Thr Glu
            115                 120                 125

Leu Gly Cys Asp Ser Ile Glu Lys Leu Lys Ala Gln Ile Pro Lys Met
        130                 135                 140

Glu Gln Glu Leu Lys Glu Pro Gly Arg Phe Lys Asp Phe Tyr Gln Phe
145                 150                 155                 160

Thr Phe Asn Phe Ala Lys Asn Pro Gly Gln Lys Gly Leu Asp Leu Glu
                165                 170                 175

Met Ala Ile Ala Tyr Trp Asn Leu Val Leu Asn Gly Arg Phe Lys Phe
            180                 185                 190

Leu Asp Leu Trp Asn Lys Phe Leu Glu His His Lys Arg Ser Ile
        195                 200                 205

Pro Lys Asp Thr Trp Asn Leu Leu Leu Asp Phe Ser Thr Met Ile Ala
    210                 215                 220

Asp Asp Met Ser Asn Tyr Asp Glu Glu Gly Ala Trp Pro Val Leu Ile
225                 230                 235                 240

Asp Asp Phe Val Glu Phe Ala Arg Pro Gln Ile Ala Gly Thr Lys Ser
                245                 250                 255

Thr Thr Val
```

<210> SEQ ID NO 3
<211> LENGTH: 876
<212> TYPE: DNA
<213> ORGANISM: Homo sapiens
<220> FEATURE:
<221> NAME/KEY: CDS
<222> LOCATION: (16)...(795)

<400> SEQUENCE: 3

```
ctggaggaca ccaac atg aac aag ttg aaa tca tcg cag aag gat aaa gtt      51
               Met Asn Lys Leu Lys Ser Ser Gln Lys Asp Lys Val
                 1               5                  10 cgt cag ttt atg atc ttc aca caa tct agt gaa aaa aca gca gta agt      99
Arg Gln Phe Met Ile Phe Thr Gln Ser Ser Glu Lys Thr Ala Val Ser
            15                  20                  25 tgt ctt tct caa aat gac tgg aag tta gat gtt gca aca gat aat ttt     147
Cys Leu Ser Gln Asn Asp Trp Lys Leu Asp Val Ala Thr Asp Asn Phe
     30                  35                  40 ttc caa aat cct gaa ctt tat ata cga gag agt gta aaa gga tca ttg     195
Phe Gln Asn Pro Glu Leu Tyr Ile Arg Glu Ser Val Lys Gly Ser Leu
45                  50                  55                  60 gac agg aag aag tta gaa cag ctg tac aat aga tac aaa gac cct caa     243
Asp Arg Lys Lys Leu Glu Gln Leu Tyr Asn Arg Tyr Lys Asp Pro Gln
                65                  70                  75 gat gag aat aaa att gga ata gat ggc ata cag cag ttc tgt gat gac     291
Asp Glu Asn Lys Ile Gly Ile Asp Gly Ile Gln Gln Phe Cys Asp Asp
            80                  85                  90 ctg gca ctc gat cca gcc agc att agt gtg ttg att att gcg tgg aag     339
Leu Ala Leu Asp Pro Ala Ser Ile Ser Val Leu Ile Ile Ala Trp Lys
        95                 100                 105 ttc aga gca gca aca cag tgc gag ttc tcc aaa cag gag ttc atg gat     387
Phe Arg Ala Ala Thr Gln Cys Glu Phe Ser Lys Gln Glu Phe Met Asp
    110                 115                 120 ggc atg aca gaa tta gga tgt gac agc aca gaa aaa cta aag gcc cag     435
Gly Met Thr Glu Leu Gly Cys Asp Ser Thr Glu Lys Leu Lys Ala Gln
125                 130                 135                 140 ata ccc aag atg gaa caa gaa ttg aaa gaa cca gga cga ttt aag gat     483
Ile Pro Lys Met Glu Gln Glu Leu Lys Glu Pro Gly Arg Phe Lys Asp
                145                 150                 155
```

```
ttt tac cag ttt act ttt aat ttt gca aag aat cca gga caa aaa gga      531
Phe Tyr Gln Phe Thr Phe Asn Phe Ala Lys Asn Pro Gly Gln Lys Gly
        160                 165                 170 tta gat cta gaa atg gcc att gcc tac tgg aac tta gtg ctt aat gga      579
Leu Asp Leu Glu Met Ala Ile Ala Tyr Trp Asn Leu Val Leu Asn Gly
            175                 180                 185 aga ttt aga ctc tta gac tta tgg aat aaa ttt ttg ttg gaa cat cat      627
Arg Phe Arg Leu Leu Asp Leu Trp Asn Lys Phe Leu Leu Glu His His
        190                 195                 200 aaa cga tca ata cca aaa gac act tgg aat ctt ctt tta gac ttc agt      675
Lys Arg Ser Ile Pro Lys Asp Thr Trp Asn Leu Leu Leu Asp Phe Ser
205                 210                 215                 220 acg atg att gca gat gac atg tct aat tat gat gaa gaa gga gca tgg      723
Thr Met Ile Ala Asp Asp Met Ser Asn Tyr Asp Glu Glu Gly Ala Trp
                225                 230                 235 cct gtt ctt att gat gac ttt gtg gaa ttt gca cgc cct caa att gct      771
Pro Val Leu Ile Asp Asp Phe Val Glu Phe Ala Arg Pro Gln Ile Ala
            240                 245                 250 ggg aca aaa agt aca aca gtg tag cactaaagga accttctaga atgtacatag    825
Gly Thr Lys Ser Thr Thr Val *
            255 tctgtacaat aaatacaaca gaaaattgca cagtcaattt ctgctggctg g             876

<210> SEQ ID NO 4
<211> LENGTH: 259
<212> TYPE: PRT
<213> ORGANISM: Homo sapiens

<400> SEQUENCE: 4

Met Asn Lys Leu Lys Ser Ser Gln Lys Asp Lys Val Arg Gln Phe Met
 1               5                  10                  15

Ile Phe Thr Gln Ser Ser Glu Lys Thr Ala Val Ser Cys Leu Ser Gln
                20                  25                  30

Asn Asp Trp Lys Leu Asp Val Ala Thr Asp Asn Phe Phe Gln Asn Pro
            35                  40                  45

Glu Leu Tyr Ile Arg Glu Ser Val Lys Gly Ser Leu Asp Arg Lys Lys
        50                  55                  60

Leu Glu Gln Leu Tyr Asn Arg Tyr Lys Asp Pro Gln Asp Glu Asn Lys
65                  70                  75                  80

Ile Gly Ile Asp Gly Ile Gln Phe Cys Asp Asp Leu Ala Leu Asp
                85                  90                  95

Pro Ala Ser Ile Ser Val Leu Ile Ile Ala Trp Lys Phe Arg Ala Ala
                100                 105                 110

Thr Gln Cys Glu Phe Ser Lys Gln Glu Phe Met Asp Gly Met Thr Glu
            115                 120                 125

Leu Gly Cys Asp Ser Thr Glu Lys Leu Lys Ala Gln Ile Pro Lys Met
130                 135                 140

Glu Gln Glu Leu Lys Glu Pro Gly Arg Phe Lys Asp Phe Tyr Gln Phe
145                 150                 155                 160

Thr Phe Asn Phe Ala Lys Asn Pro Gly Gln Lys Gly Leu Asp Leu Glu
                165                 170                 175

Met Ala Ile Ala Tyr Trp Asn Leu Val Leu Asn Gly Arg Phe Arg Leu
            180                 185                 190

Leu Asp Leu Trp Asn Lys Phe Leu Leu Glu His His Lys Arg Ser Ile
        195                 200                 205

Pro Lys Asp Thr Trp Asn Leu Leu Leu Asp Phe Ser Thr Met Ile Ala
    210                 215                 220
```

```
Asp Asp Met Ser Asn Tyr Asp Glu Glu Gly Ala Trp Pro Val Leu Ile
225                 230                 235                 240

Asp Asp Phe Val Glu Phe Ala Arg Pro Gln Ile Ala Gly Thr Lys Ser
                245                 250                 255

Thr Thr Val

<210> SEQ ID NO 5
<211> LENGTH: 21
<212> TYPE: DNA
<213> ORGANISM: Artificial Sequence
<220> FEATURE:
<223> OTHER INFORMATION: PCR Primer

<400> SEQUENCE: 5
tgggggaaag aatggatgaa c                                        21

<210> SEQ ID NO 6
<211> LENGTH: 21
<212> TYPE: DNA
<213> ORGANISM: Artificial Sequence
<220> FEATURE:
<223> OTHER INFORMATION: PCR Primer

<400> SEQUENCE: 6
cttggtacag cgctgggcgc t                                        21

<210> SEQ ID NO 7
<211> LENGTH: 20
<212> TYPE: DNA
<213> ORGANISM: Artificial Sequence
<220> FEATURE:
<223> OTHER INFORMATION: PCR Primer

<400> SEQUENCE: 7
ctggaggaca ccaacatgaa                                          20

<210> SEQ ID NO 8
<211> LENGTH: 20
<212> TYPE: DNA
<213> ORGANISM: Artificial Sequence
<220> FEATURE:
<223> OTHER INFORMATION: PCR Primer

<400> SEQUENCE: 8
ccagccagca gaaattgact                                          20

<210> SEQ ID NO 9
<211> LENGTH: 27
<212> TYPE: DNA
<213> ORGANISM: Artificial Sequence
<220> FEATURE:
<223> OTHER INFORMATION: RACE Primer

<400> SEQUENCE: 9
catgcaataa tcaacacact aatgctg                                  27

<210> SEQ ID NO 10
<211> LENGTH: 23
<212> TYPE: DNA
<213> ORGANISM: Artificial Sequence
<220> FEATURE:
<223> OTHER INFORMATION: RACE Primer
```

```
<400> SEQUENCE: 10
atcgagtgcc aggtcatcac aga                                           23

<210> SEQ ID NO 11
<211> LENGTH: 27
<212> TYPE: DNA
<213> ORGANISM: Artificial Sequence
<220> FEATURE:
<223> OTHER INFORMATION: RACE Primer

<400> SEQUENCE: 11
tacactctct cgtatataaa gttcagg                                       27

<210> SEQ ID NO 12
<211> LENGTH: 20
<212> TYPE: DNA
<213> ORGANISM: Artificial Sequence
<220> FEATURE:
<223> OTHER INFORMATION: Blot probe

<400> SEQUENCE: 12
ctggaggaca ccaacatgaa                                               20

<210> SEQ ID NO 13
<211> LENGTH: 20
<212> TYPE: DNA
<213> ORGANISM: Artificial Sequence
<220> FEATURE:
<223> OTHER INFORMATION: Blot probe

<400> SEQUENCE: 13
ccagccagca gaaattgact                                               20

<210> SEQ ID NO 14
<211> LENGTH: 21
<212> TYPE: DNA
<213> ORGANISM: Artificial Sequence
<220> FEATURE:
<223> OTHER INFORMATION: Blot probe

<400> SEQUENCE: 14
tgggacgaca tggagaaaat c                                             21

<210> SEQ ID NO 15
<211> LENGTH: 20
<212> TYPE: DNA
<213> ORGANISM: Artificial Sequence
<220> FEATURE:
<223> OTHER INFORMATION: Blot probe

<400> SEQUENCE: 15
agggaggagc tggaagcagc                                               20

<210> SEQ ID NO 16
<211> LENGTH: 20
<212> TYPE: DNA
<213> ORGANISM: Artificial Sequence
<220> FEATURE:
<223> OTHER INFORMATION: PCR Primer

<400> SEQUENCE: 16
tgttgtggga gggaagaaac                                               20
```

```
<210> SEQ ID NO 17
<211> LENGTH: 20
<212> TYPE: DNA
<213> ORGANISM: Artificial Sequence
<220> FEATURE:
<223> OTHER INFORMATION: PCR Primer

<400> SEQUENCE: 17
tggcagggct ctgactaact                                                 20

<210> SEQ ID NO 18
<211> LENGTH: 20
<212> TYPE: DNA
<213> ORGANISM: Artificial Sequence
<220> FEATURE:
<223> OTHER INFORMATION: PCR Primer

<400> SEQUENCE: 18
tgcgtatcac agggtatgga                                                 20

<210> SEQ ID NO 19
<211> LENGTH: 20
<212> TYPE: DNA
<213> ORGANISM: Artificial Sequence
<220> FEATURE:
<223> OTHER INFORMATION: PCR Primer

<400> SEQUENCE: 19
tttaagtgga aatgggagcg                                                 20

<210> SEQ ID NO 20
<211> LENGTH: 20
<212> TYPE: DNA
<213> ORGANISM: Artificial Sequence
<220> FEATURE:
<223> OTHER INFORMATION: PCR Primer

<400> SEQUENCE: 20
aggagccgca cttatctgaa                                                 20

<210> SEQ ID NO 21
<211> LENGTH: 20
<212> TYPE: DNA
<213> ORGANISM: Artificial Sequence
<220> FEATURE:
<223> OTHER INFORMATION: PCR Primer

<400> SEQUENCE: 21
aactgccatc aaacagggac                                                 20

<210> SEQ ID NO 22
<211> LENGTH: 20
<212> TYPE: DNA
<213> ORGANISM: Artificial Sequence
<220> FEATURE:
<223> OTHER INFORMATION: PCR Primer

<400> SEQUENCE: 22
cctgtccaaa ctaaggctcg                                                 20

<210> SEQ ID NO 23
<211> LENGTH: 20
<212> TYPE: DNA
<213> ORGANISM: Artificial Sequence
<220> FEATURE:
<223> OTHER INFORMATION: PCR Primer
```

-continued

```
<400> SEQUENCE: 23
tgttgtacaa agcgagcacc                                               20

<210> SEQ ID NO 24
<211> LENGTH: 20
<212> TYPE: DNA
<213> ORGANISM: Artificial Sequence
<220> FEATURE:
<223> OTHER INFORMATION: PCR Primer

<400> SEQUENCE: 24
tcctcttgag cagggacagt                                               20

<210> SEQ ID NO 25
<211> LENGTH: 20
<212> TYPE: DNA
<213> ORGANISM: Artificial Sequence
<220> FEATURE:
<223> OTHER INFORMATION: PCR Primer

<400> SEQUENCE: 25
gagaaacctg ggaagggaag                                               20

<210> SEQ ID NO 26
<211> LENGTH: 20
<212> TYPE: DNA
<213> ORGANISM: Artificial Sequence
<220> FEATURE:
<223> OTHER INFORMATION: PCR Primer

<400> SEQUENCE: 26
gtaacagccc tagcaggcag                                               20

<210> SEQ ID NO 27
<211> LENGTH: 20
<212> TYPE: DNA
<213> ORGANISM: Artificial Sequence
<220> FEATURE:
<223> OTHER INFORMATION: PCR Primer

<400> SEQUENCE: 27
cgcagagatg cagagacttg                                               20

<210> SEQ ID NO 28
<211> LENGTH: 20
<212> TYPE: DNA
<213> ORGANISM: Artificial Sequence
<220> FEATURE:
<223> OTHER INFORMATION: PCR Primer

<400> SEQUENCE: 28
caccatcacc tctgctctca                                               20

<210> SEQ ID NO 29
<211> LENGTH: 20
<212> TYPE: DNA
<213> ORGANISM: Artificial Sequence
<220> FEATURE:
<223> OTHER INFORMATION: PCR Primer

<400> SEQUENCE: 29
cagacactgc tgtcctccaa                                               20
```

CARCINOMA-RELATED GENES AND POLYPEPTIDES AND METHODS OF USE THEREOF

RELATED APPLICATION

This application claims the benefit of priority of U.S. Ser. No. 60/355,009, filed Feb. 8, 2002, the contents of which are incorporated herein in their entirety.

FIELD OF THE INVENTION

The present invention relates to novel nucleic acids and polynucleotides, to novel proteins and polypeptides encoded thereby, and to novel methods of use of these compositions in fields associated with oncogenesis, tumor progression, and to diagnosis, prognosis and therapeutic approaches related to various cancers.

BACKGROUND OF THE INVENTION

Duplication of genetic information is an essential mechanism for oncogene activation. Genome wide screening using comparative genomic hybridization has resulted in the identification of many recurrent amplification events in a variety of tumors systems. Duplication at 3q is of particular interest as it is present in a wide range of tumors with a prevalence as high as 92%. Squamous cell carcinomas of mucosal origin show a particular predilection for duplication of this locus, including those originating from the lung, head and neck, esophagus, and cervix. Moreover, the presence of 3q duplication is associated with tumor progression and an aggressive clinical course. However, the gene targets driving selection for 3q amplification remain ill defined. Knowledge of the gene targets is required to develop diagnostic and prognostic methods. In addition, identification of relevant gene targets permits the development of specific therapeutic strategies designed to inhibit tumor progression. These persisting needs are addressed in the present invention.

SUMMARY OF THE INVENTION

In a first aspect, the present invention provides an isolated polynucleotide (an "Oncoseq" polynucleotide) and an isolated polypeptide encoded thereby (an "Oncoseq" polypeptide), wherein the polynucleotide includes a nucleotide sequence chosen from the group consisting of:

a) a nucleotide sequence encoding the polypeptide given by SEQ ID NO:2 or SEQ ID NO:4;

b) a nucleotide sequence complementary to a nucleotide sequence encoding the polypeptide given by SEQ ID NO:2 or SEQ ID NO:4;

c) a nucleotide sequence encoding a polypeptide whose amino acid sequence is at least 90% identical to the amino acid sequence given by SEQ ID NO:2 or SEQ ID NO:4;

d) a nucleotide sequence complementary to a nucleotide sequence encoding a polypeptide whose amino acid sequence is at least 90% identical to the amino acid sequence given by SEQ ID NO:2 or SEQ ID NO:4;

e) a nucleotide sequence that is a fragment of any of the nucleotide sequences of a) through d); and f) a nucleotide sequence that hybridizes to a nucleotide sequence given by a) through e).

In important embodiments, the nucleotide sequence encodes the polypeptide given by SEQ ID NO:2 or SEQ ID NO:4, or is complementary to SEQ ID NO:2 or SEQ ID NO:4. In a still further important embodiment, the nucleotide sequence is given by SEQ ID NO:1 or SEQ ID NO:3, or sequences complementary to SEQ ID NO:1 or SEQ ID NO:3. In various embodiments the polynucleotide may be either a RNA or a DNA. In another important embodiment, the polynucleotides of the invention encode fragments of an Oncoseq polypeptide that may be used as immunogens in stimulating the production of antibodies. The invention further discloses pharmaceutical compositions that contain a polynucleotide of the invention in a pharmaceutically acceptable carrier, as well as kits that provide a polynucleotide of the invention in a container. In an advantageous embodiment the polynucleotide in the kit is an antisense polynucleotide, a small inhibitory. Polynucleotide, or a micro polynucleotide.

In another embodiment of this aspect of the invention, a vector that includes any polynucleotide sequence of the invention is provided; in significant embodiments the vector is an expression vector in which the polynucleotide sequence is operably linked to provide for expression of the encoded polypeptide. In a further important embodiment of the invention, a vector is a component of a host cell, and such a host cell may: be employed in a method of preparing any polypeptide of the invention by steps including culturing the host cell described above under conditions suitable for expression of the polypeptide, and isolating the polypeptide. In a significant embodiment of this method, the vector encodes the amino acid sequence given by SEQ ID NO:2 or SEQ ID NO:4.

In another aspect of the invention, an antibody that binds immunospecifically to any polypeptide of the invention is provided. In an important embodiment, the antibody binds immunospecifically to a polypeptide whose amino acid sequence is given by SEQ ID NO:2 or SEQ ID NO:4. In significant embodiments, the antibody may be a polyclonal antibody, a monoclonal antibody, a humanized antibody, or a fully human antibody. Kits that include an antibody of the invention placed in a container are also provided.

The invention provides several additional aspects, which are methods of using the polynucleotides of the invention. In one such aspect, the invention provides a method of detecting the presence of or quantifying the amount of an Oncoseq polynucleotide in a sample including the steps of:

a) providing a sample that includes sample nucleic acid; and b) detecting the presence of or quantifying the amount of an Oncoseq polynucleotide in the sample nucleic acid.

In another aspect of the invention, a method is provided for determining whether the copy number of an Oncoseq sequence in a sample differs from the copy number of the Oncoseq sequence in a reference, wherein the method includes the steps of:

a) providing a sample having sample nucleic acid comprising the Oncoseq sequence;

b) detecting whether the amount of the Oncoseq sequence in the sample nucleic acid differs from the amount of the Oncoseq sequence in a reference nucleic acid comprising the Oncoseq sequence.

If it is found that the amounts differ then the copy number of the Oncoseq sequence in the sample differs from the copy number of the Oncoseq sequence in the reference.

In a further aspect, the invention provides a method of contributing to the diagnosis of, prognosis of, or to developing a therapeutic strategy for, a pathology in a first subject. In this pathology, the copy number of an Oncoseq sequence is known to differ from the copy number of the Oncoseq sequence in a nonpathological state. This method includes the steps of:

a) providing a sample from the first subject that includes sample nucleic acid, wherein the sample nucleic acid includes the Oncoseq sequence;

b) detecting whether the amount of the Oncoseq sequence in the sample nucleic acid differs from the amount of the Oncoseq sequence in a reference nucleic acid, wherein the reference nucleic acid is from a reference from a second subject known not to have the pathology and wherein the reference nucleic acid includes the Oncoseq sequence; and c) determining that the copy number of the Oncoseq sequence in the first subject differs from the copy number of the Oncoseq sequence in the second subject when the amounts detected in step b) differ from each other.

This finding contributes to the diagnosis of, prognosis of, or developing a therapeutic strategy for, the pathology.

With respect to the various aspects providing the above methods employing polynucleotides, in important embodiments, a target nucleotide sequence that includes at least a portion of the Oncoseq sequence in the sample nucleic is expanded, and tie detecting or quantifying in step b) is performed on the expanded target Oncoseq sequence. Advantageously, the expanding comprises reverse transcription or a polymerase chain reaction, or both. In additional significant embodiments, the detecting or quantifying in step b) includes fluorescence in situ hybridization or a real-time polymerase chain reaction; significantly, as an alternative, the detecting or quantifying in step b) includes contacting the sample nucleic acid with a probe nucleic acid includes a polynucleotide of the invention that hybridizes to an Oncoseq polynucleotide under conditions that assure specific hybridization of the Oncoseq polynucleotide to the probe, and detecting the presence of or quantifying the amount of the Oncoseq polynucleotide that hybridizes to the probe nucleic acid. In further significant embodiments the Oncoseq polynucleotide includes a label, which may be a fluorochrome; and, in still further advantageous embodiments, the detecting or quantifying includes detecting or quantifying the label. In still additional significant embodiments of the methods, the probe nucleic acid is bound to a solid surface, such as may occur in a microarray. In yet additional significant embodiments of the methods directed to assessing copy number, and to contributing to diagnosis, prognosis, or development of therapy for a pathology, the sample is provided from a mammal and the reference is provided from the same species of mammal, and more significantly the sample is provided from a human and the reference is provided from a human. In still other important embodiments the sample includes a cancer cell but the reference does not include a cancer cell. In embodiments related to a pathology, important examples of such pathologies include a cancer, a tumor, a carcinoma, a sarcoma, a blastoma, a lymphoma, a leukemia, or a neoplastic disease.

Additional significant aspects of the invention are directed to assaying for an Oncoseq polypeptide. In one aspect, a method is provided of detecting the presence or quantifying the amount of an Oncoseq polypeptide in a sample including the steps of:

a) providing a sample that includes sample polypeptides wherein the sample polypeptides are suspected to include the Oncoseq polypeptide;

b) contacting the polypeptide with a specific binding agent that binds an Oncoseq polypeptide of the invention under conditions that assure binding of the Oncoseq polypeptide to the specific binding agent; and c) detecting the presence or quantifying the amount of the specific binding agent that binds to the Oncoseq polypeptide.

In an additional aspect, the invention provides a method of determining whether the amount of an Oncoseq polypeptide in a sample differs from the amount of the Oncoseq polypeptide in a reference.

This method includes the steps of:

a) providing a sample suspected to include the Oncoseq polypeptide;

b) contacting the sample with a specific binding agent that binds an Oncoseq polypeptide of the invention under conditions that assure binding of the Oncoseq polypeptide to the specific binding agent; and c) detecting whether the amount of the specific binding agent that binds to the sample differs from the amount of the specific binding agent that binds to a reference, wherein the reference is prepared by providing a reference that includes a standard or reference amount of the Oncoseq polypeptide, and contacting the reference with the specific binding agent used in step b) under the same conditions used in step b).

In a still further aspect, the invention provides a method of contributing to the diagnosis, prognosis, or therapy of a pathology in a first subject. In this pathology the amount of an Oncoseq polypeptide is known to differ from the amount of the Oncoseq polypeptide in a nonpathological state. The method includes the steps of:

a) providing a sample from the first subject suspected to include the Oncoseq polypeptide;

b) contacting the sample with a specific binding agent that binds an Oncoseq polypeptide of the invention under conditions that assure binding of the Oncoseq polypeptide to the specific binding agent; and c) detecting whether the amount of the specific binding agent that binds to the sample differs from the amount of the specific binding agent that binds to a reference, wherein the reference is provided from a second subject known not to have the pathology and wherein the reference includes the Oncoseq polypeptide, and contacting the reference with the specific binding agent used in step b) under the same conditions used in step b).

The result of this comparison contributes to the diagnosis, prognosis, or therapy of the pathology.

With respect to the various aspects providing the above methods related to the assaying of the Oncoseq polypeptides, in significant embodiments, the specific binding agent includes a label, or the specific binding agent binds a secondary binding agent that includes a label, which may be a fluorochrome; and the detecting or quantifying includes detecting or quantifying the label. In still additional significant embodiments of the methods, the specific binding agent is an antibody, and the Oncoseq polypeptide is bound to a solid surface, such as may occur in a microtiter plate or a microarray. In yet additional significant embodiments of the methods directed to assessing copy number, and to contributing to diagnosis, prognosis, or development of therapy for a pathology, the sample is provided from a human and the reference is provided from a human. In still other important embodiments the sample includes a cancer cell but the reference does not include a cancer cell. In embodiments related to a pathology, important examples of such pathologies include a cancer, a tumor, a carcinoma, a sarcoma, a blastoma, a lymphoma, a leukemia, or a neoplastic disease.

In yet a further aspect, the invention provides a method of inhibiting the growth of a cell. This method includes contacting the cell with a composition that lowers expression of an Oncoseq nucleotide sequence in the cell. In advantageous embodiments of this method the composition includes an Oncoseq polynucleotide of the invention. In another significant embodiment of this method, the copy number of the Oncoseq gene in the cell is pathologically high.

In still an additional aspect of the invention, a method is provided of inhibiting the growth of a cell in a sample. In this method, the cell has a copy number of an Oncoseq gene characteristic of a pathology. The method includes contacting the cell with a composition that includes an Oncoseq polynucleotide of the invention or an Oncoseq polypeptide of the invention. In significant embodiments of this method, the sample is located in a human subject. In an additional important embodiment, the polynucleotide includes an antisense polynucleotide, a small inhibitory polynucleotide, or a micro polynucleotide. In significant embodiments of the invention the composition interferes with the activity of an Oncoseq gene or an Oncoseq polypeptide; such a composition may be a polypeptide that includes an Oncoseq polypeptide fragment, such as a fragment that includes an amino acid sequence beginning at residue 136 and ending at residue 245 of SEQ ID NO:2 or SEQ ID NO:4. In still additional important embodiments the pathology is a cancer, a tumor, a carcinoma, a sarcoma, a blastoma, a lymphoma, a leukemia, or a neoplastic disease, and in particular the pathology is a squamous cell carcinoma.

BRIEF DESCRIPTION OF THE FIGURES

FIG. 1. Structural and expression analysis of Oncoseq. Panel a. Representation of a polynucleotide sequence (SEQ ID NO:1) that includes an open reading frame of 780 nucleotides for Oncoseq, and the amino acid sequence of the 259-residue polypeptide encoded thereby (SEQ ID NO:2). The predicted start codon is indicated by an asterisk. A polyadenylation signal, AATAAA is underlined. The functional domain DUF298 containing a basic helix-loop-helix leucine zipper motif is highlighted in bold font. Panel b. Image of genomic DNA for the human Oncoseq gene, spanning approximately 43.6 Kb showing 7 exons encoding the gene product. Panel c. Dendrogram representing the phylogenetic conservation of human Oncoseq (identified as SCCRO, top branch) with orthologous genes identified in several species.

FIG. 5. Panel a Expression of Oncoseq mRNA determined using real-time PCR on 45 non-small cell lung carcinomas (23 squamous cell carcinomas and 12 adenocarcinomas) and 45 histologically normal lung tissues. The ordinate scale is logarithmic. Panel b. Survival times of human patients without and with high extents of Oncoseq (labeled as SCRO) gene duplication.

FIG. 6. Western blot analysis of NIH-3T3 cells stably transfected with pUSEamp (shown as pUSEamp-3T3) and pUSEamp-Oncoseq (clone 28; shown as pUSEamp-3T3-28). The top gel set shows detection using anti-Oncoseq antibody and the bottom set uses anti-beta actin antibody.

FIG. 7. Photomicrographs of NIH-3T3 cells transfected with pUSEamp (left panel) and with pUSEamp-Oncoseq (center and right panels).

FIG. 8. Panel a. Growth curves of NIH-3T3 cells transfected with pUSEampOncoseq (clone 28; shown as PUSEamp-SCRO-3T3) or pUSEamp (clone 28; shown as pUSEamp-3T3). Panel b. FACS analysis of effect of transfection of MDA 1186 cells with an antisense vector to Oncoseq. Panel c. Change in cell growth in serum deficient medium for NIH-3T3 cells transfected with pUSEamp-Oncoseq (upper curve) compared to transfection with pUSEamp (lower curve).

FIG. 9. Panel a. Growth in soft agar assay showing colony formation for NIH-3T3 cells transfected with pUSEampOncoseq (identified as pUSEamp-SCRO-3T3) clones 14 and 28 compared with NIH-3T3 cells transfected with pUSEamp. The first two labels at the bottom refer to colony size. Panel b. Photographs showing tumor growth in a BALB/c athymic nude mouse injected with NIH-3T3 cells transfected with pUSEampOncoseq (shown as pUSEamp-SCRO) compared with a mouse transfected NIH-3T3 cells transfected with vector alone.

DETAILED DESCRIPTION OF THE INVENTION

TABLE 1

Figure 2A:
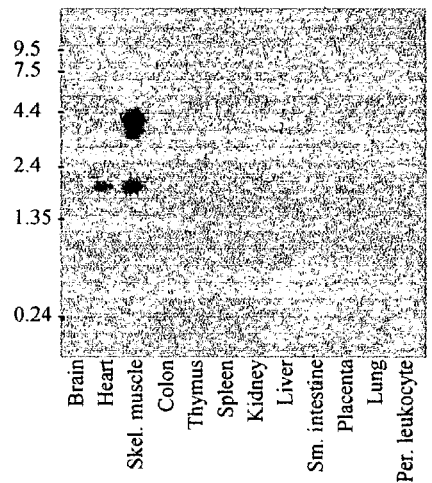
FIG. 2. Expression of Oncoseq polynucleotides in tissues. Panel a. Image of a northern blot of several tissues probed using a full-length Oncoseq sequence. Panel b. Real-time PCR analysis of Oncoseq expression in adult tissues. Panel c. Real-time PCR analysis of Oncoseq expression in fetal tissues.

Correspondence of Compositions and SEQ ID NOS

| COMPOSITION | POLYNUCLEOTIDE SEQ ID NO: | POLYPEPTIDE SEQ ID NO: |
| --- | --- | --- |
| Oncoseq1 | 1 | 2 |
| Oncoseq2 | 3 | 4 |
| PCR Primer P1 | 5 | |
| PCR Primer P2 | 6 | |
| PCR Primer P3 | 7 | |
| PCR Primer P4 | 8 | |
| RACE Primer R-1 | 9 | |
| RACE Primer NR-1 | 10 | |
| RACE Primer R-2 | 11 | |
| Probe Oncoseq1 | 12 | |
| Probe Oncoseq2 | 13 | |
| Probe β-actin1 | 14 | |
| Probe β-actin2 | 15 | |
| Gli1 5' | 16 | |
| Gli1 3' | 17 | |
| Hormone receptor 5' | 18 | |
| Hormone receptor 3' | 19 | |
| 11β-hydroxysteroid dehydrogenase 5' | 20 | |
| 11β-hydroxysteroid dehydrogenase 3' | 21 | |
| TGF-β1 5' | 22 | |
| TGF-β1 3' | 23 | |
| Insulin-like growth factor 2 5' | 24 | |
| Insulin-like growth factor 2 3' | 25 | |
| NOV 5' | 26 | |
| NOV 3' | 27 | |
| LTBP 5' | 28 | |
| LTBP 3' | 29 | |

The present invention relates to novel polynucleotide sequences and their encoded polypeptides, herein designated as Oncoseq nucleic acids, Oncoseq polynucleotides, Oncoseq proteins, Oncoseq polypeptides and similar terminology. In one embodiment an Oncoseq polynucleotide and an Oncoseq polypeptide relate to the sequences presented in FIG. 1a, and to fragments, variants and similar sequences thereto. The polynucleotide of FIG. 1a is designated SEQ ID NO:1, and the encoded polypeptide as SEQ ID NO:2. In an additional embodiment of the invention the polynucleotide contained within SEQ ID NO:1 beginning at position number 58 and ending at position number 837 is disclosed. The polynucleotide of SEQ ID NO:1, positions 58-837 encodes a polypeptide that is identical to the polypeptide of SEQ ID NO:2. The polynucleotide of SEQ ID NO:1, positions 43-918 and the polypeptide of SEQ ID NO:2 are disclosed in GenBank Acc. No. AF456425 (released to the public as of Feb. 19, 2002). The invention further relates to an Oncoseq2 polynucleotide presented in Table 2 (SEQ ID NO:3) and to fragments, variants and similar sequences thereto. An Oncoseq2 polypeptide encoded by SEQ ID NO:3 is presented in Table 2 using the one-letter amino acid code (SEQ ID NO:4); the invention further relates to fragments, variants and similar sequences thereto. The polynucleotide of SEQ ID NO:3 and the polypeptide of SEQ ID NO:4 are disclosed in GenBank Acc. No. AF456426 (released to the public as of Feb. 19, 2002).

TABLE 2

An Oncoseq2 Polynucleotide

```
  1 ctggaggaca ccaacatgaa caagttgaaa tcatcgcaga aggataaagt tcgtcagttt 61 atgatcttca cacaatctag tgaaaaaaca gcagtaagtt gtctttctca aaatgactgg 121 aagttagatg ttgcaacaga taatttttc caaaatcctg aactttatat acgagagagt 181 gtaaaaggat cattggacag gaagaagtta gaacagctgt acaatagata caaagaccct 241 caagatgaga ataaaattgg aatagatggc atacagcagt tctgtgatga cctggcactc 301 gatccagcca gcattagtgt gttgattatt gcgtggaagt tcagagcagc aacacagtgc 361 gagttctcca aacaggagtt catggatggc atgacagaat taggatgtga cagcacagaa 421 aaactaaagg cccagatacc caagatggaa caagaattga agaaccagg acgatttaag 481 gattttacc agtttacttt taattttgca aagaatccag acaaaaagg attagatcta 541 gaaatggcca ttgcctactg gaacttagtg cttaatggaa gatttagact cttagactta
```

TABLE 2-continued

An Oncoseq2 Polynucleotide

```
601 tggaataaat ttttgttgga acatcataaa cgatcaatac caaaagacac ttggaatctt
661 cttttagact tcagtacgat gattgcagat gacatgtcta attatgatga agaaggagca
721 tggcctgttc ttattgatga ctttgtggaa tttgcacgcc ctcaaattgc tgggacaaaa
781 agtacaacag tgtagcacta aaggaacctt ctagaatgta catagtctgt acaataaata
841 caacagaaaa ttgcacagtc aatttctgct ggctgg
```

TABLE 2

An Oncoseq2 Polypeptide

MNKLKSSQKDKVRQFMIFTQSSEKTAVSCLSQNDWKLDVATDNFFQNPELYIRESVKGSLDRKKLEQLYN

RYKDPQDENKIGIDGIQQFCDDLALDPASISVLIIAWKFRAATQCEFSKQEFMDGMTELGCDSTEKLKAQ

IPKMEQELKEPGRFKDFYQFTFNFAKNPGQKGLDLEMAIAYWNLVLNGRFRLLDLWNKFLLEHHKRSIPK

DTWNLLLDFSTMIADDMSNYDEEGAWPVLIDDFVEFARPQIAGTKSTTV

As used herein and in the claims, "Oncoseq" or any "OncoseqX", where "X" may be 1, 2, 3, or 4, relates generally to nucleic acids, polynucleotides, and oligonucleotides whose sequences are given by or contained within SEQ ID NO:1 or 3, or whose sequences are similar to sequences of SEQ ID NO:1 or 3, or to fragments thereof, or to complementary sequences thereto. Further as used herein and in the claims, "Oncoseq" or any "OncoseqX" where "X" may be 1, 2, 3, or 4, relates generally to proteins, polypeptides, and oligopeptides whose sequences are given by or contained within SEQ ID NO:2 or 4, or whose sequences are similar to sequences of SEQ ID NO:2 or 4, or to fragments thereof.

Oncoseq alleles, which are disclosed and characterized in the present invention, are novel oncogenes identified in primary squamous cell carcinoma tissues as being colocalized with the highest gene duplication peak within the 3q26.3 locus, using a positional cloning approach. Oncoseq itself is highly duplicated in these carcinomas. Overexpression of Oncoseq is correlated with gene duplication, aggressive clinical behavior, and malignant transformation in vitro, making it a strong candidate as the target for 3q amplification The gene is highly oncogenic, for as shown herein, Oncoseq induces malignant transformation in vitro and imparts an aggressive phenotype to aberrantly expressing primary squamous cell carcinomas. The Oncoseq gene is evolutionarily conserved and has a basic region-helix-loop-helix-leucine zipper motif, suggesting it may function as a transcription factor. This assertion is corroborated by the a strong positive effect of Oncoseq expression observed on Gli1 promoter activity Thus Oncoseq may be involved in hedgehog signaling, based on its ability to regulate Gli1 transcription. The Oncoseq protein was found to localize to the nucleus under stress conditions, inducing a significant increase in Gli1 transcription. These data indicate that Oncoseq is the gene driving selection for 3q amplification in squamous cell carcinomas and may be activator of Gli1 transcription. The effects characterized for Oncoseq, including growth promotion and Gli1 activation are inhibited in a dose-dependent fashion by an antisense Oncoseq polynucleotide.

As used herein, the term "isolated", and similar words based on these, when used to describe a nucleic acid, a polynucleotide, an oligonucleotides, a protein, a polypeptide, or an oligopeptide, relate to being altered "by the hand of man" from its natural state; i.e., if it occurs in nature, it has been changed or removed from its original environment, or both. For example, a naturally occurring polynucleotide or a polypeptide naturally present in a living organism in its natural state is not "isolated," but the same polynucleotide or polypeptide separated from materials with which it coexists in its natural state is "isolated", as the term is employed herein. Generally, removal of at least one significant coexisting material constitutes "isolating" a nucleic acid, a polynucleotide, an oligonucleotide, a protein, a polypeptide, or an oligopeptide. In many cases several, many, or most coexisting materials may be removed to isolate the nucleic acid, a polynucleotide, an oligonucleotides, a protein, a polypeptide, or an oligopeptide. By way of nonlimiting example, with respect to polynucleotides, the term "isolated" may mean that it is separated from the chromosome and cell in which it naturally occurs. Further by way of example, "isolating" a protein or polypeptide may mean separating it from another component in a cell lysate or cell homogenate.

A nucleic acid, a polynucleotide, an oligonucleotides, a protein, a polypeptide, or an oligopeptide that is the product of an in vitro synthetic process or a chemical synthetic process is essentially isolated as the result of the synthetic process. In important embodiments such synthetic products are treated to remove reagents and precursors used, and side products produced, by the process.

As part of or following isolation from the natural state in which it occurs, Oncoseq polynucleotides can be joined to other polynucleotides, for mutagenesis, to form fusion proteins, and for propagation or expression in a host, for instance. The isolated polynucleotides, alone or joined to other polynucleotides such as vectors, can be introduced into host cells, in culture or in whole organisms, after which such DNAs still would be isolated, as the term is used herein, because they would not be in their naturally occurring form or environment.

Similarly, the polynucleotides and polypeptides may occur in a composition, such as a media formulations, solutions for introduction of polynucleotides or polypeptides, for example, into cells, compositions or solutions for chemical or enzymatic reactions, for instance, which are not naturally occurring compositions, and, therein remain isolated polynucleotides or polypeptides within the meaning of that term as it is employed herein.

As used herein and in the claims, a "nucleic acid" or "polynucleotide", and similar terms based on these, refer to polymers composed of naturally occurring nucleotides as well as to polymers composed of synthetic or modified nucleotides. Thus, as used herein, a polynucleotide that is a RNA, or a polynucleotide that is a DNA may include naturally occurring moieties such as the naturally occurring bases and ribose or deoxyribose rings, or they may be composed of synthetic or modified moieties as described in the following. The linkages between nucleotides is commonly the 3'-5' phosphate linkage, which may be a natural phosphodiester linkage, a phosphothioester linkage, and still other synthetic linkages. Examples of modified backbones include, phosphorothioates, chiral phosphorothioates, phosphorodithioates, phosphotriesters, aminoalkylphosphotriesters, methyl and other alkyl phosphonates including 3'-alkylene phosphonates, 5'-alkylene phosphonates and chiral phosphonates, phosphinates, phosphoramidates including 3'-amino phosphoramidate and aminoalkylphosphoramidates, thionophosphoramidates, thionoalkylphosphonates, thionoalkylphosphotriesters, selenophosphates and boranophosphates. Additional linkages include phosphotriester, siloxane, carbonate, carboxymethylester, acetamidate, carbamate, thioether, bridged phosphoramidate, bridged methylene phosphonate, bridged phosphorothioate and sulfone internucleotide linkages. Other polymeric linkages include 2'-5' linked analogs of these. See U.S. Pat. Nos. 6,503,754 and 6,506,735 and references cited therein, incorporated herein by reference. Nucleic acids and polynucleotides may be 20 or more nucleotides in length, or 100 or more, or 1000 or more, or tens of thousands or more, or hundreds of thousands or more, in length. Examples of polynucleotides of great length include polynucleotide sequence subjects of the invention incorporated into bacterial artificial chromosomes (BACs) or yeast artificial chromosomes (YACs), for example.

As used herein, "oligonucleotides" and similar terms based on this relate to short polymers composed of naturally occurring nucleotides as well as to polymers composed of synthetic or modified nucleotides, as described in the immediately preceding paragraph. Oligonucleotides may be 10 or more nucleotides in length, or 11, 12, 13, 14, 15, 16, 17, 18, 19, 20 or more, 22 or more, 24 or more, 26 or more, 28 or more, 30 or more, 35 or more, 40 or more, 45 or more, up to about 50, nucleotides in length.

As used herein and in the claims "nucleotide sequence", "oligonucleotide sequence" or "polynucleotide sequence", "polypeptide sequence", "amino acid sequence", "peptide sequence", "oligopeptide sequence", and similar terms, relate interchangeably both to the sequence of bases or amino acids that an oligonucleotide or polynucleotide, or polypeptide, peptide or oligopeptide has, as well as to the oligonucleotide or polynucleotide, or polypeptide, peptide or oligopeptide structure possessing the sequence. A nucleotide sequence or a polynucleotide sequence, or polypeptide sequence, peptide sequence or oligopeptide sequence furthermore relates to any natural or synthetic polynucleotide or oligonucleotide, or polypeptide, peptide or oligopeptide, in which the sequence of bases or amino acids is defined by description or recitation of a particular sequence of letters designating bases or amino acids as conventionally employed in the field.

The bases in oligonucleotides and polynucleotides may be "unmodified" or "natural" bases include the purine bases adenine (A) and guanine (G), and the pyrimidine bases thymine (T), cytosine (C) and uracil (U). In addition they may be bases with modifications or substitutions. As used herein, modified bases include other synthetic and natural bases such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl uracil and cytosine and other alkynyl derivatives of pyrimidine bases, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 0.5-substituted uracils and cytosines, 7=methylguanine and 7-methyladenine, 2-fluoro-adenine, 2-amino-adenine, 8-azaguanine and 8-azaadenine, 7-deazaguanine and 7-deazaadenine and 3-deazaguanine and 3-deazaadenine. Further modified bases include tricyclic pyrimidines such as phenoxazine cytidine (1H-pyrimido[5,4-b][1,4]benzoxazin-2(3H)-one), phenothiazine cytidine (1-pyrimido[5,4b][1,4]benzothiazin-2(3H)-one), G-clamps such as a substituted phenoxazine cytidine (e.g. 9-(2-aminoethoxy)-H-pyrimido[5,4-b][1,4]benzoxazin-2(3H)-one), carbazole cytidine (2H-pyrimido[4,5-b]indol-2-one), pyridoindole cytidine (H-pyrido[3',2':4,5]pyrrolo[2,3-d]pyrimidin-2-one). Modified bases may also include those in which the purine or pyrimidine base is replaced with other heterocycles, for example 7-deazaadenine, 7-deazaguanosine, 2-aminopyridine and 2-pyridone. Further bases include those disclosed in U.S. Pat. No. 3,687,808, those disclosed in The Concise Encyclopedia Of Polymer Science And Engineering, pages 858-859, Kroschwitz, J. I., ed. John Wiley & Sons, 1990, those disclosed by Englisch et al., Angewandte Chemie, International Edition (1991) 30, 613, and those disclosed by Sanghvi, Y. S., Chapter 15, Antisense Research and Applications, pages 289-302, Crooke, S. T. and Lebleu, B., ed., CRC Press, 1993. Certain of these bases are particularly useful for increasing the binding affinity of the oligomeric compounds of the invention. These include 5-substituted pyrimidines, 6-azapyrimidines and N-2, N-6 and O-6 substituted purines, including 2-aminopropyladenine, 5-propynyluracil and 5-propynylcytosine. 5-methylcytosine substitutions have been shown to increase nucleic acid duplex stability by 0.6-1.2.degree. C. (Sanghvi, Y. S., Crooke, S. T. and Lebleu, B., eds., Antisense Research and Applications, CRC Press, Boca Raton, 1993, pp. 276-278) and are presently preferred base substitutions, even more particularly when combined with 2'-O-methoxyethyl sugar modifications. See U.S. Pat. Nos. 6,503,754 and 6,506,735 and references cited therein, incorporated herein by reference.

As used herein and in the claims, the term "complementary" and similar words based on this, relate to the ability of a first nucleic acid base in one strand of a nucleic acid, polynucleotide or oligonucleotide to interact specifically only with a particular second nucleic acid base in a second strand of a nucleic acid, polynucleotide or oligonucleotide. By way of nonlimiting example, if the naturally occurring bases are considered, A and T or U interact with each other, and G and C interact with each other. As employed in this invention and in the claims, "complementary" is intended to signify "fully complementary", namely, that when two polynucleotide strands are aligned with each other, there will be at least a portion of the strands in which each base in a sequence of contiguous bases in one strand is complementary to an interacting base in a sequence of contiguous bases of the same length on the opposing strand.

As used herein, "hybridize", "hybridization" and similar words relate to a process of forming a nucleic acid, polynucleotide, or oligonucleotide duplex by causing strands with complementary sequences to interact with each other. The interaction occurs by virtue of complementary bases on each of the strands specifically interacting to form a pair. The ability of strands to hybridize to each other depends on a variety of conditions, as set forth below. Nucleic acid strands hybridize with each other when a sufficient number of corresponding positions in each strand are occupied by nucleotides that can interact with each other. It is understood by workers of skill in the field of the present invention, including by way of nonlimiting example molecular biologists and cell biologists, that the sequences of strands forming a duplex need not be 100% complementary to each other to be specifically hybridizable.

As used herein "fragment" and similar words based on this, relate to portions of a nucleic acid, polynucleotide or oligonucleotide, or to portions of a protein or polypeptide shorter than the full sequence of a reference. The sequence of bases, or the sequence of amino acid residues, in a fragment is unaltered from the sequence of the corresponding portion of the molecule from which it arose; there are no insertions or deletions in a fragment in comparison with the corresponding portion of the molecule from which it arose. As contemplated herein, a fragment of a nucleic acid or polynucleotide, such as an oligonucleotide, is 15 or more bases in length, or 16 or more, 17 or more, 18 or more, 21 or more, 24 or more, 27 or more, 30 or more, 50 or more, 75 or more, 100 or more bases in length, up to a length that is one base shorter than the full length sequence. Oligonucleotides may be chemically synthesized and may be used as probes. A fragment of a protein or polypeptide, such as a peptide or oligopeptide, may be 5 amino acid residues or more in length, or 6 or more, 7 or more, 8 or more, 9 or more, 10 or more, 15 or more, 20 or more, 25 or more, 30 or more, 50 or more, 10 or more residues in length, up to a length that is one residue shorter than the full length sequence.

As used herein the term "protein" or "polypeptide", and similar words based on these, relate to polymers of alpha amino acids joined in peptide linkage. Alpha amino acids include those encoded by triplet codons of nucleic acids, polynucleotides and oligonucleotides. They may also include amino acids with side chains that differ from those encoded by the genetic code.

As used herein, a "mature" form of a polypeptide or protein disclosed in the present invention is the product of a naturally occurring polypeptide or precursor form or proprotein. The naturally occurring polypeptide, precursor or proprotein includes, by way of nonlimiting example, the full length gene product, encoded by the corresponding gene. Alternatively, it may be defined as the polypeptide, precursor or proprotein encoded by an open reading frame described herein. The product "mature" form arises, again by way of nonlimiting example, as a result of one or more naturally occurring processing steps as they may take place within the cell, or host cell, in which the gene product arises. Examples of such processing steps leading to a "mature" form of a polypeptide or protein include the cleavage of the N-terminal methionine residue encoded by the initiation codon of an open reading frame, or the proteolytic cleavage of a signal peptide or leader sequence. Thus a mature form arising from a precursor polypeptide or protein that has residues 1 to N, where residue 1 is the N-terminal methionine, would have residues 2 through N remaining after removal of the N-terminal methionine. Alternatively, a mature form arising from a precursor polypeptide or protein having residues 1 to N, in which an N-terminal signal sequence from residue 1 to residue M is cleaved, would have the residues from residue M+1 to residue N remaining. Further as used herein, a "mature" form of a polypeptide or protein may arise from a step of post-translational modification other than a proteolytic cleavage event. Such additional processes include, by way of non-limiting example, glycosylation, myristoylation or phosphorylation. In general, a mature polypeptide or protein may result from the operation of only one of these processes, or a combination of any of them.

As used herein, the term "quantifying", "quantitation", and similar words based on these, relate to determining at least approximately the quantity, mass, or concentration in a unit volume, of a nucleic acid, polynucleotide or oligonucleotide, or a protein or polypeptide molecule. Optimally, determining the quantity, mass or concentration will provide a result that is highly accurate and highly precise. Any physical or chemical property of the molecule that is approximately linearly related to the quantity, mass, or concentration may be used in quantitating the molecule. Furthermore, any physical or chemical property of a molecule that may be indirectly characterized in a way that preserves an approximately linear relationship to the quantity, mass, or concentration may similarly be used in quantifying the molecule. Any equivalent means for quantitating a nucleic acid, polynucleotide or oligonucleotide, or a protein or polypeptide, is contemplated within the scope of the invention.

As used herein, the term "copy number", and similar words based on this, relate to the multiplicity of occurrence of a given gene or DNA sequence in the genome of a cell, and therefore in the DNA obtained from a sample such as a tissue sample constituted primarily or entirely of the cell. The DNA sequence whose copy number is signified here may be the DNA sequence of a gene encoding a gene product, or may be a portion of the DNA sequence of a gene encoding a gene product.

As used herein the terms "duplication", "gene duplication", and similar words based on these, relate to process or result in which a gene present in most normal cells at a given level of copy number becomes multiplied by a number equal to or greater than 2 in the genome of the cell. It is understood that, as used herein, "duplication", "gene duplication" and similar words refer not only to a doubling of the copy number of a gene, but generally to multiplication of a gene to any extent that may be observed in a cell. The copy number of duplicated genes may indeed be much higher than twice the copy number in most normal cells, or can be lower than twice the copy number in most normal cells (as when there are three copies of a certain gene). All such high extents of replication are comprehended within the terms "duplication", "gene duplication".

As used herein, the term "sample" and similar words based on this, relate to any substance, composition or object that comprises a nucleic acid, polynucleotide or oligonucleotide, or a protein or polypeptide, in a form identical to, or minimally altered from, the form of the a nucleic acid, polynucleotide or oligonucleotide, or a protein or polypeptide, in an intact cell. Broadly, a sample can be a biological sample comprising intact cells. In this broad sense, DNA in a sample is genomic DNA, and RNA in a sample includes mRNA, tRNA, rRNA, and similar RNA. A sample may also contain DNA that is minimally altered (see below) from genomic DNA in view of steps such as isolating nuclei from a sample of cells, or disrupting nuclei contained in a sample of cells. In several embodiments contemplated herein, a sample comprising a nucleic acid, polynucleotide or oligonucleotide, or a protein or polypeptide, is obtained from a subject suspected of having, or diagnosed as having, a particular pathology. The term "sample nucleic acid" or "sample polynucleotide" relates to a nucleic acid or polynucleotide contained in or obtained from a sample as defined in this paragraph. The term "sample polypeptide" relates to a polypeptide contained in or obtained from a sample as defined in this paragraph.

As used herein, the term "reference" and similar words based on this, relate to any substance, composition or object as defined above for "sample", with the exception that, in those embodiments of methods in which the sample is obtained from a subject suspected of having, or diagnosed as having, a particular pathology, a reference used in a conjugate step in the same method is from a subject known not to have the pathology. More broadly, a reference is from a source that reliably can serve as a control, or as characterizing a nonexperimental status, or nonpathological state. The term "reference nucleic acid" or "reference polynucleotide" relates to a nucleic acid or polynucleotide contained in or obtained from a reference as defined in this paragraph. The term "reference polypeptide" relates to a polypeptide contained in or obtained from a reference as defined in this paragraph.

As used herein, the term "expanding", "expansion", and similar words based on these, when used to describe a process carried out with sample nucleic acid or sample polynucleotide, or with reference nucleic acid or reference polynucleotide, relate to replicating a sequence, or sequences, present in the population of nucleic acids manyfold to provide an expanded population of polynucleotide sequences. The sequences of the polynucleotides in the expanded population are preserved essentially intact, being essentially identical to the sequences of the corresponding sequences in the unexpanded population.

As used herein, the term "probe nucleic acid", and similar phrases based on this, relate to a nucleic acid molecule used to interrogate a population of polynucleotide molecules. The probe nucleic acid is characterized according to its properties; a property of interest in many embodiments of the present invention is the nucleotide sequence of the probe. Another property of interest is the ability of a probe nucleic acid to hybridize with a sequence on a second nucleic acid, polynucleotide or oligonucleotide under conditions that promote hybridization to occur.

Origins of Sample Nucleic Acid And Reference Nucleic Acid. The methods of the present invention operate on sample nucleic acid and on reference nucleic acid. These compositions are obtained from, or derived from, biological samples of interest. In many instances, the biological samples are of interest in a particular experimental environment or clinical setting. In general the samples and reference, providing-the sample nucleic acid and the reference nucleic acid, respectively, are cells obtained from a subject. The cells may be present in a biological fluid, the fluid including by way of nonlimiting example, blood, a blood fraction containing nucleated cells, sputum, saliva, semen, and the like. The cells may be obtained from an epithelial surface such as buccal epithelium, vaginal epithelium, colonic epithelium, and similar epithelial surfaces. Furthermore cells may be obtained from endothelial surfaces such as vascular endothelium. The cells additionally may be obtained from a surgical procedure such as a biopsy or a surgical removal of an organ or tissue. By way of nonlimiting example, biopsy and surgical sources for such cells include lung, esophagus, stomach, small intestine, large intestine, rectum, breast, ovary, testis, uterus, kidney, pancreas, brain, bladder, adipose, skeletal muscle, and so on. In particular embodiments of the present invention, sample nucleic acid is obtained from squamous cells of the buccal cavity, nasal cavity, pharynx, esophagus, bronchial passages, other head and neck sources, lung, ovary and cervix. Generally, sources of sample and reference cells are known to workers of skill in the field of the present invention, including by way of nonlimiting example molecular biologists, cell biologists, diagnostic clinicians, oncologists, surgeons, and so on. Equivalent sources of sample nucleic acid and reference nucleic acid are contemplated within the scope of the present invention.

Sample Nucleic Acid And Reference Nucleic Acid. The sample or reference includes sample nucleic acid or reference nucleic acid, respectively, which generally includes genomic DNA or cellular RNA including mRNA, tRNA, rRNA, and similar RNA. Sample nucleic acid and reference nucleic acid may be used in any state of isolation or purification. By way of nonlimiting example, the sample and reference may be disrupted such that the cells and nuclei are lysed, thereby providing the nucleic acid in the complete cell lysate. The sample and reference may alternatively be further processed to separate the nucleic acid from other components Of the cell lysate, and may further be fractionated to yield compositions enriched in deoxyribonucleoprotein and/or cellular RNA, or processed to provide compositions enriched in cellular or genomic DNA free of its complexed proteins. All such compositions, and similar compositions of lesser or greater extents of purification of the nucleic acid present in the sample and reference, are contemplated in the methods of this invention. Broadly, experimental methods that can be applied to carry out fractionation or separation of subcellular components in a cell lysate, include, by way of nonlimiting example, variations in pH, ionic strength, use of divalent cations, addition of organic solvents such as aliphatic alcohols, centrifugation, filtration, ultrafiltration, chromatography, and the like. Generally, methods of providing sample and reference nucleic acid compositions are known to workers of skill in the field of the present invention, including by way of nonlimiting example molecular biologists, cell biologists, biochemists, diagnostic clinicians, and so on.

Expansion of DNA Populations. Sample nucleic acid and reference nucleic acid are expanded to provide an expanded population of polynucleotides encompassing at least a portion of an Oncoseq sequence. Expanding the fragments is accomplished by various processes that use a DNA polymerase to synthesize new polynucleotide chains. Oligonucleotides used to prime the polymerase activity have sequences specifically designed to bind to an Oncoseq sequence and target expansion of at least a portion of an Oncoseq sequence. Appropriate DNA polymerases are available to use in the expansion of the fragments generated by site-specific cleavage such as occurs with restriction endonucleases, and primed according to methods such as those disclosed herein. In particular embodiments of the present invention a cDNA to an Oncoseq mRNA is prepared; in such embodiments a further step is reverse transcription of the mRNA in a sample nucleic acid and a reference nucleic acid to provide the cDNA.

Processes for expanding DNA fragments are widely described in the fields related to the present invention, and are known to workers of skill in these fields. Such workers include those skilled in molecular biology, cell biology, biochemistry, clinical research, and so on. Processes include amplification by polymerase chain reaction (PCR), and are described, by way of nonlimiting example, in Molecular Cloning: A Laboratory Manual (3$^{rd}$ Edition) (Sambrook, J et al. (2001) Cold Spring Harbor Laboratory Press, Cold Spring Harbor, N.Y.), Short protocols in molecular biology (5$^{th}$ Ed.) (Ausubel FM et al. (2002) John Wiley & Sons, New York City), U.S. Pat. Nos. 4,683,195 and 4,683,202. Additional expansion methods include anchor PCR or RACE PCR, or, alternatively, a ligation chain reaction (LCR) (see, e.g., Landegran et al. (1988) *Science* 241:1077-1080; and Nakazawa et al. (1994) *Proc. Natl. Acad. Sci. USA* 91:360-364; see also Abravaya et al. (1995) *Nucl Acids Res* 23:675-682).

Alternative-expansion methods include: self sustained sequence replication (Guatelli et al., 1990, *Proc Natl Acad Sci USA* 87:1874-1878), transcriptional amplification system (Kwoh, et al., 1989, *Proc Natl Acad Sci USA* 86:1173-1177), Q-Beta Replicase (Lizardi et al, 1988, *BioTechnology* 6:1197). Equivalent procedures that accomplish expansion of an Oncoseq sequence are also contemplated within the present invention.

Detection and Labeling. An Oncoseq polynucleotide may be detected in many ways. Detecting may include any one or more processes that result in the ability to observe the presence and or the amount of an Oncoseq polynucleotide. In one embodiment a sample nucleic acid containing an Oncoseq polynucleotide may be detected prior to expansion. In an alternative embodiment an Oncoseq polynucleotide in a sample may be expanded to provide an expanded Oncoseq polynucleotide, and the expanded polynucleotide is detected or quantitated. Physical, chemical or biological methods may be used to detect and quantitate an Oncoseq polynucleotide. Physical methods include, by way of nonlimiting example, surface plasmon resonance (SPR) detection such as binding a probe to a surface and using SPR to detect binding of an Oncoseq polynucleotide to the immobilized probe, or having a probe in a chromatographic medium and detecting binding of an Oncoseq polynucleotide in the chromatographic medium. Physical methods further include a gel electrophoresis or capillary electrophoresis format in which Oncoseq polynucleotides are resolved from other polynucleotides, and the resolved Oncoseq polynucleotides are detected. Chemical methods include hybridization methods generally in which an Oncoseq polynucleotide hybridizes to a probe. Biological methods include causing an Oncoseq polynucleotide to exert a biological effect on a cell, and detecting the effect. The present invention discloses examples of biological effects which may be used as a biological assay. In many embodiments, the polynucleotides may be labeled as described below to assist in detection and quantitation. For example, in embodiments not including expansion, a sample nucleic acid may be labeled by chemical or enzymatic addition of a labeled moiety such as a labeled nucleotide or a labeled oligonucleotide linker.

Expanded polynucleotides may be detected and/or quantitated directly. For example, an expanded polynucleotide may be subjected to electrophoresis in a gel that resolves by size, and stained with a dye that reveals its presence and amount. Alternatively an expanded Oncoseq polynucleotide may be detected upon exposure to a probe nucleic acid under hybridizing conditions (see below) and binding by hybridization is detected and/or quantitated. Detection is accomplished in any way that permits determining that an Oncoseq polynucleotide has bound to the probe. This can be achieved by detecting the change in a physical property of the probe brought about by hybridizing a fragment. A nonlimiting example of such a physical detection method is SPR.

An alternative way of accomplishing detection is to use a labeled form of the expanded polynucleotide, and to detect the bound label. The polynucleotide may be labeled as an additional feature in the process of expanding the nucleic acid. A Label may be incorporated into the fragments by use of modified nucleotides included in the compositions used to expand the fragment populations. A label may be a radioisotopic label, such as $^{125}$I, $^{35}$S, $^{32}$P, $^{14}$C, or $^{3}$H, for example, that is detectable by its radioactivity. Alternatively, a label may be selected such that it can be detected using a spectroscopic method, for example. In one instance, a label may be a chromophore, absorbing incident light. A preferred label is one detectable by luminescence. Luminescence includes fluorescence, phosphorescence, and chemiluminescence. Thus a label that fluoresces, or that phosphoresces, or that induces a chemiluminscent reaction, may be employed. Examples of suitable fluorescent labels, or fluorochromes, include a $^{152}$Eu label, a fluorescein label, a rhodamine label, a phycoerythrin label, a phycocyanin label, Cy-3, Cy-5, an allophycocyanin label, an o-phthaldehyde label, and a fluorescamine label. Luminescent labels afford detection with high sensitivity. A label may furthermore be a magnetic resonance label, such as a stable free radical label detectable by electron paramagnetic resonance, or a nuclear label, detectable by nuclear magnetic resonance. A label may still further be a ligand in a specific ligand-receptor pair; the presence of the ligand is then detected by the secondary binding of the specific receptor, which commonly is itself labeled for detection. Non limiting examples of such ligand-receptor pairs include biotin and streptavidin or avidin, a hapten such as digoxigenin or antigen and its specific antibody, and so forth. In summary, labeling can be accomplished in a wide variety of ways.

Detecting, quantitating, including labeling, methods are known generally to workers of skill in fields related to the present invention, including, by way of nonlimiting example, workers of skill in spectroscopy, nucleic acid chemistry, biochemistry, molecular biology and cell biology. Quantitating permits determining the quantity, mass, or concentration of a nucleic acid or polynucleotide, or fragment thereof, that has bound to the probe. Quantitation includes determining the amount of change in a physical, chemical, or biological property as described in this and preceding paragraphs. For example the intensity of a signal originating from a label may be used to assess the quantity of the nucleic acid bound to the probe. Any equivalent process yielding a way of detecting the presence and/or the quantity, mass, or concentration of a polynucleotide or fragment thereof that hybridizes to a probe nucleic acid is envisioned to be within the scope of the present invention.

Probe Nucleic Acids. A probe nucleic acid may be any nucleic acid molecule that includes a nucleotide sequence of at least a portion of an Oncoseq sequence, or a sequence complementary to at least a portion of an Oncoseq sequence. By way of nonlimiting example, a probe nucleic acid may be a ribonucleic acid, a deoxyribonucleic acid, a cDNA or fragment thereof, or a modified nucleic acid in which the modification may be a chemical modification of the bases, of the ribose or deoxyribose rings, or of the phosphodiester bonds. Commonly modifications may be introduced to confer enhanced stability on the probe nucleic acid against degradation or for other purposes. Such modifications include, by way of nonlimiting example, methylation of bases, derivatization or substitution of hydroxyl groups on the pentose rings, or use of phosphorothioate or phosphorodithioate linkages between nucleotides.

Preparation and use of probe nucleic acids are broadly described in the fields related to the present invention, and are known to workers of skill in these fields. Such workers include those skilled in molecular biology, cell biology, biochemistry, oncology, inflammatory disease, metabolic disease, clinical research, and so on. Equivalent compositions that bind an Oncoseq sequence are also contemplated to serve as probes in the present invention.

In certain embodiments of the present invention a probe nucleic acid is immobilized on a solid surface for ease of manipulation.

Microarrays. Particular embodiments of the present invention contemplate use in a high throughput environment, in which a plurality of probe nucleic acids is used simultaneously to interrogate a population of polynucleotides or fragments thereof. Furthermore the methods of the invention are intended to minimize the requirements for the amount of sample nucleic acid and reference nucleic acid required. An advantageous way to accomplish this is to prepare microarrays of probe nucleic acids, wherein each locus in the array includes a distinct probe nucleic acid characterized or characterizable as described above. In a microarray the dimensions of each locus are minimized to the greatest extent possible, and the detection methods correspondingly are adapted to obtain signals from the miniaturized locus. Probe nucleic acids may be affixed to a solid surface such as is used in a microarray by a wide variety of procedures. A probe may be bound to a surface by noncovlaent or covalent interactions.

Covalent binding may be accomplished, for example, by coating a surface with a composition that includes moieties that react with the probe, then contacting the surface at an intended locus with the probe, thereby binding the probe to the surface. Preparation of microarrays is described in U.S. Pat. No. 6,506,558 and references cited therein. Methods of preparing microarrays are widely known to workers of skill in fields related to the present invention, including molecular biology, cell biology, biochemistry, clinical research, solid state chemistry, microtechnology, nanotechnology, and so on. Any equivalent process that accomplishes binding a probe nucleic acid to a solid surface, and in particular that allows formation of a microarray suitable for interrogation of a population of polynucleotides or fragments thereof and detection and/or quantitation of the binding of a DNA fragment, is contemplated as being within the scope of the invention.

Hybridization. An expanded polynucleotide is interrogated for the presence of an Oncoseq sequence by hybridizing to a probe nucleic acid, or to a microarray comprising a plurality of probe nucleic acids. Hybridizing results in the formation of a double stranded nucleic acid structure in which the base sequences of the two strands are at least partly complementary to each other. Hybridization of complementary nucleic acid sequences to each other depends on factors that include, by way of nonlimiting example, the length of the complementary sequence, the base composition of the complementary sequences, the relative concentrations of the two strands, the time allowed for hybridization to occur, the overall ionic strength of the hybridzing environment, the concentration of divalent cations such as $Mg^{+2}$, the presence of destabilizing organic cosolvents, such as formamide, and the temperature. Hybridization conditions are chosen that assure optimal hybridization of the probe and the DNA molecule to each other. As used herein, the phrase "specific hybridization conditions", and similar terms, refers to conditions under which a probe, primer or oligonucleotide will hybridize to a target sequence; optimally the probe will hybridize to no other sequences, and more generally will not hybridize to sequences below a specified degree of similarity to the probe. Generally, specific conditions are selected to be about 5° C. lower than the thermal melting point (Tm) for the specific sequence in a medium of defined composition and pH. The Tm is the temperature (under defined ionic strength, pH and nucleic acid concentration) at which 50% of the probes complementary to the target sequence hybridize to the target sequence at equilibrium. Hybridization procedures are widely known to workers of skill in fields related to the present invention, including those skilled in molecular biology, cell biology, biochemistry, oncology, inflammatory disease, clinical research, and so on. For example, workers of skill in fields related to the present invention know that hybridization conditions are broadly discussed in sources such as Sambrook et al., 2001, and Ausubel et al., 2002. These skilled workers know how to vary hybridization conditions in a routine fashion in order to optimize binding of a fragment to a probe. Any equivalent set of conditions that accomplishes hybridization of a member of a population of polynucleotides or fragments thereof to a complementary probe is within the scope of the present invention.

Detection and Quantitation of a Hybridized Oncoseq Sequence. The presence and/or the amount of an expanded Oncoseq polynucleotide bound to a probe nucleic acid is then detected and/or quantitated. As discussed earlier, any physical, spectroscopic or analogous property of the hybridized duplex may be used in making this determination. The method used must be suitable for use at the locus at which the probe is found; in the case of a microarray, the method must have the spatial resolution to detect and/or quantitate binding at each locus in the microarray. Instruments, apparatuses and methods of detection and/or quantitation are widely known to workers of skill in fields related to the present invention, including those skilled in molecular biology, cell biology, biochemistry, oncology, inflammatory disease, metabolic disease, clinical research, spectroscopy, solid state chemistry, microtechnology, nanotechnology, and so on. Detection and/or quantitation may include methods, such as algorithmic processes resident in the memory of a computer, that transform raw signal information into a result that provides a symbol corresponding to detecting the presence or absence of binding of a fragment to a probe, or corresponding to a quantity that represents the amount, mass or concentration of a fragment bound to a probe. Any equivalent process that provides for the detection and/or quantitation of binding is contemplated within the scope of the invention.

A "specific binding agent" of an Oncoseq polypeptide or an Oncoseq oligopeptide is any substance that specifically binds the Oncoseq polypeptide or oligopeptide, but binds weakly or not at all to other polypeptides and oligopeptides. Nonlimiting examples of specific binding agents include antibodies, specific receptors for Oncoseq polypeptides, binding domains of such antibodies and receptors, aptamers, imprinted polymers, and so forth.

The present invention includes methods of determining the degree of gene duplication of an Oncoseq gene in a subject. As an alternative, methods of determining the copy number of an Oncoseq gene in a subject are presented in the invention. The invention furthermore includes methods of determining the degree, or fold-enhancement, of transcriptional expression of an Oncoseq gene in a subject. Still further, the invention includes methods of determining the degree, or fold-enhancement of protein expression of an Oncoseq gene in a subject. Such a subject may be suspected of suffering from a pathology, or may already have been diagnosed as suffering from a pathology, wherein the pathology may, by way of nonlimiting example, be a cancer, a tumor, a carcinoma, a sarcoma, a blastoma, a lymphoma, a leukemia, a neoplastic disease, a congenital disorder, a metabolic disorder, diabetes, or an inflammatory disease.

The results obtained from the methods of determining the degree of gene duplication, or the copy number, or the degree of transcriptional expression, or the degree of protein expression, of an Oncoseq gene in such a subject contribute to a diagnosis, to a prognosis, and/or to development of a therapeutic strategy with respect to the subject. Such results contribute to diagnosis of the pathology, for the information resulting from the determination provides additional data concerning the state of the pathology in the subject. They contribute to prognosis of the pathology in the subject, for the information that results from the determinations convey useful data related to the severity and stage of progression of the pathology, which impacts on a prognosis for the pathology. They contribute to development of a therapeutic strategy, since assessment of the state of the pathology and its stage of progression are factors in determining a course of treatment. Various alternative courses of treatment include, by way of nonlimiting example, a first surgical resection of a pathological tissue or organ if not already done, further surgical removal of pathological tissue from a tissue or organ, radiological treatment of a pathology, and selection of a particular chemotherapeutic treatment. If the pathology is a cancer, a tumor, a carcinoma, a sarcoma, a blastoma, a lymphoma, a leukemia, or a neoplastic disease, for example, chemotherapeutic agents may be chosen from pharmaceutical substances, nonlimiting examples of which include taxol (paclitaxel), cisplatin, carboplatin, phosphamide, adriamycin, doxorubicin, actinomycin, an immunoconjugate with a toxin, and similar substances.

The results obtained using methods of the present invention may additionally be used in assigning a stage to a pathology in a subject, and also to monitoring the efficacy of a course of therapy during and after the therapy is applied to a subject.

Comparison and evaluation of results obtained using the methods of the present invention are procedures widely known to workers of skill in fields related to the invention, including by way of nonlimiting example, workers in clinical diagnostics, internal medicine, oncology, clinical statistics, molecular biologists, and the like. Any equivalent means of carrying out the comparison and evaluation of these results is within the scope of the invention.

Nucleic Acids

The novel nucleic acids of the invention include those that encode an Oncoseq protein or a protein resembling an Oncoseq protein, or biologically active portions thereof The nucleic acids include nucleic acids encoding polypeptides that include the amino acid sequence of one or more of SEQ ID NOS:2 and 4.

In some embodiments, a nucleic acid encoding a polypeptide having the amino acid sequence of one or more of SEQ ID NOS:2 and 4 includes the nucleic acid sequence of any of SEQ ID NOS:1 and 3, or a fragment thereof Additionally, the invention includes mutant or variant nucleic acids of any of SEQ ID NOS:1 and 3, or a fragment thereof, any of whose bases may be changed from the disclosed sequence while still encoding a protein that maintains its Oncoseq protein-like activities and physiological functions. The invention further includes the complement of the nucleic acid sequence of any of SEQ ID NOS:1 and 3, including fragments, derivatives, analogs and homolog thereof. The invention additionally includes nucleic acids or nucleic acid fragments, or complements thereto, whose structures include chemical modifications.

Also included are nucleic acid fragments sufficient for use as hybridization probes to identify Oncoseq protein-encoding nucleic acids (e.g., Oncoseq mRNA) and fragments for use as polymerase chain reaction (PCR) primers for the amplification or mutation of Oncoseq nucleic acid molecules. As used herein, the term "nucleic acid molecule" is intended to include DNA molecules (e.g., cDNA or genomic DNA), RNA molecules (e.g., mRNA), analogs of the DNA or RNA generated using nucleotide analogs, and derivatives, fragments and homologs thereof The nucleic acid molecule can be single-stranded or double-stranded, but preferably is double-stranded DNA.

A nucleic acid molecule of the present invention, e.g., a nucleic acid molecule having the nucleotide sequence of SEQ ID NOS:1 and 3, or a complement of any of this nucleotide sequence, can be isolated using standard molecular biology techniques and the sequence information provided herein. Using all or a portion of the nucleic acid sequence of any of SEQ ID NOS:1 and 3 as a hybridization probe, Oncoseq nucleic acid sequences can be isolated using standard hybridization and cloning techniques (e.g., as described in Sambrook et al., eds., MOLECULAR CLONING: A LABORATORY MANUAL $2^{nd}$ Ed., Cold Spring Harbor Laboratory Press, Cold Spring Harbor, N.Y., 1989 and Ausubel, et al., eds., CURRENT PROTOCOLS IN MOLECULAR BIOLOGY, John Wiley & Sons, New York, N.Y., 1993.)

A nucleic acid of the invention can be expanded using cDNA, mRNA or alternatively, genomic DNA, as a template and appropriate oligonucleotide primers according to standard PCR amplification techniques. The nucleic acid so amplified can be cloned into an appropriate vector and characterized by DNA sequence analysis. Furthermore, oligonucleotides corresponding to Oncoseq nucleotide sequences can be prepared by standard synthetic techniques, e.g., using an automated DNA synthesizer.

In another embodiment, an isolated nucleic acid molecule of the invention comprises a nucleic acid molecule that is a complement of the nucleotide sequence shown in any of SEQ ID NOS:1 and 3, or a portion of this nucleotide sequence. A nucleic acid molecule that is complementary to the nucleotide sequence shown in of any of SEQ ID NOS:1 and 3 can form hydrogen bonds with no mismatches to the nucleotide sequence shown in of any of SEQ ID NOS:1 and 3, thereby forming a stable duplex.

As used herein, the term "binding" means the physical or chemical interaction between two polypeptides or compounds or associated polypeptides or compounds or combinations thereof. Binding includes ionic, polar, hydrogen bonding, van der Waals, hydrophobic interactions, and other noncovlaent interactions. In certain circumstances binding may be covalent. A physical interaction can be either direct or indirect. Indirect interactions may be through or due to the effects of another polypeptide or compound. Direct binding refers to interactions that do not take place through, or due to, the effect of another polypeptide or compound, but instead are without other substantial chemical intermediates.

Derivatives and analogs of polynucleotides and polypeptides may be full length or other than full length, if the derivative or analog contains a modified nucleic acid or amino acid, as described below. Derivatives or analogs of the nucleic acids or proteins of the invention include, but are not limited to, molecules comprising regions that are substantially similar to the nucleic acids or proteins of the invention, in various embodiments, by at least about 70%, 80%, 85%, 90%, 95%, 98%, or even 99% identity (with a preferred identity of 80-99%) over a nucleic acid or amino acid sequence of identical size or when compared to an aligned sequence using methods described in detail below.

"Percent identity", or "percent similarity", or "homology", or variations thereof, when used to characterize a nucleic acid sequence or an amino acid sequence, refer to sequences characterized by a similarity at the nucleotide level or amino acid level as discussed above. Similar nucleotide sequences encode those sequences coding for isoforms of an Oncoseq polypeptide. Isoforms can be expressed in different tissues of the same organism as a result of, for example, alternative splicing of RNA. Alternatively, isoforms can be encoded by different genes. In the present invention, similar nucleotide sequences include nucleotide sequences encoding for an Oncoseq polypeptide of species other than humans, including, but not limited to, mammals, and thus can include, e.g., mouse, rat, rabbit, dog, cat cow, horse, and other organisms. Similar nucleotide sequences also include, but are not limited to, naturally occurring allelic variations and mutations of the nucleotide sequences set forth herein. A similar nucleotide sequence does not, however, include the nucleotide sequence encoding a human Oncoseq protein. Similar nucleic acid sequences include those nucleic acid sequences that encode conservative amino acid substitutions (see below) in any of SEQ ID NOS:2 and 4 as well as a polypeptide having Oncoseq protein activity. Biological activities of the Oncoseq proteins are described herein.

The nucleotide sequence determined from the cloning of the human Oncoseq gene allows for the generation of probes and primers designed for use in identifying the cell types disclosed and/or cloning Oncoseq homologues in other cell types, e.g., from other tissues, as well as Oncoseq homologues from other mammals. The probe/primer typically comprises a substantially purified oligonucleotide. The oligonucleotide typically comprises a region of nucleotide sequence that hybridizes with high specificity under suitable conditions to at least about 12, 25, 50, 100, 150, 200, 250, 300, 350 or 400 or more consecutive sense strand nucleotide sequence of SEQ ID NOS:1 and 3; or an anti-sense strand nucleotide sequence of SEQ ID NOS:1 and 3; or of a naturally occurring mutant of SEQ ID NOS:1 and 3.

Probes based on the human Oncoseq nucleotide sequence can be used to detect transcripts or genomic sequences encoding the same or similar proteins. In various embodiments, the probe further Comprises a label group attached thereto, e.g., the label group can be a radioisotope, a fluorescent compound, an enzyme, or an enzyme co-factor. Such probes can be used as a part of a diagnostic test kit for identifying cells or tissue which misexpress an Oncoseq protein, such as by measuring a level of an Oncoseq protein-encoding nucleic acid in a sample of cells from a subject e.g., detecting Oncoseq mRNA levels or determining whether a genomic Oncoseq gene has been mutated or deleted.

A polypeptide having a "biologically active portion" of an Oncoseq protein refers to polypeptides exhibiting activity similar, but not necessarily identical to, an activity of a polypeptide of the present invention, including mature forms, as measured in a particular biological assay, with or without dose dependency. A nucleic acid fragment encoding a "biologically active portion" of an Oncoseq protein can be prepared by isolating a portion of SEQ ID NOS:1 and 3, that encodes a polypeptide having an Oncoseq protein biological activity such as those disclosed herein, expressing the encoded portion of Oncoseq protein (e.g., by recombinant expression in vitro) and assessing the activity of the encoded portion of Oncoseq protein.

Oncoseq Variants

The invention further encompasses nucleic acid molecules that differ from the disclosed Oncoseq nucleotide sequences due to degeneracy of the genetic code. These nucleic acids thus encode the same Oncoseq protein as that encoded by the nucleotide sequence shown in SEQ ID NOS:1 and 3. In another embodiment, an isolated nucleic acid molecule of the invention has a nucleotide sequence encoding a protein having an amino acid sequence shown in any of SEQ ID NOS:2 and 4.

In addition to the human Oncoseq nucleotide sequence show in any of SEQ ID NOS:1 and 3, it will he appreciated by those skilled in the art that DNA sequence polymorphisms that lead to changes in the amino acid sequences of Oncoseq protein may exist within a population (e.g., the human population). Such genetic polymorphism in the Oncoseq gene may exist among individuals within a population due to natural allelic variation. As used herein, the terms "gene" and "recombinant gene" refer to nucleic acid molecules comprising an open reading frame encoding an Oncoseq protein, preferably a mammalian Oncoseq protein. Such natural allelic variations can typically result in 1-5% variance in the nucleotide sequence of the Oncoseq gene. Any and all such nucleotide variations and resulting amino acid polymorphisms in the Oncoseq protein that are the result of natural allelic variation and that do not alter the functional activity of the Oncoseq protein are intended to be within the scope of the invention.

Moreover, nucleic acid molecules encoding Oncoseq proteins from other species, and thus that have a nucleotide sequence that differs from the human sequence of any of SEQ ID NOS:1 and 3, are intended to be within the scope of the invention. Nucleic acid molecules corresponding to natural allelic variants and homologues of the Oncoseq cDNAs of the invention can be isolated based on their homology to the human Oncoseq nucleic acids disclosed herein using the human cDNAs, or a portion thereof, as a hybridization probe according to standard hybridization techniques under stringent hybridization conditions.

Homologs, orthologs and paralogs to a, nucleic acid encoding an Oncoseq protein can be obtained by varying the hybridization conditions with all or a portion of the particular human sequence as a probe using methods well known in the art for nucleic acid hybridization and cloning.

Conservative Mutations

In addition to naturally-occurring allelic variants of the Oncoseq sequence that may exist in the population, the skilled artisan will further appreciate that changes can be introduced by mutation into the nucleotide sequence of any of SEQ ID NOS:1 and 3, thereby leading to changes in the amino acid sequence of the encoded Oncoseq protein, without altering the functional ability of the Oncoseq protein. For example; nucleotide substitutions leading to amino acid substitutions at "non-essential" amino acid residues can be made in the sequence of any of SEQ ID NOS:1 and-3. A "non-essential" amino acid residue is a residue at a position in the sequence that can be altered from the wild-type sequence of the Oncoseq protein without altering the biological activity, whereas an "essential" amino acid residue is a residue at a position that is required for biological activity. For example, amino acid residues that are invariant among members of a family of Oncoseq proteins, of which the Oncoseq proteins of the present invention are members, are predicted to be particularly unamenable to alteration. Whether a position in an amino acid sequence of polypeptide is invariant or subject to substitution is readily apparent upon examination of a multiple sequence alignment of homologs, orthologs and paralogs of the polypeptide.

Another aspect of the invention pertains to nucleic acid molecules encoding Oncoseq proteins that contain changes in amino acid residues that are not essential for activity. Such Oncoseq proteins differ in amino acid sequence from any of SEQ ID NOS:2 and 4 yet retain biological activity. In one embodiment, the isolated nucleic acid molecule comprises a nucleotide sequence encoding a protein, wherein the protein comprises an amino acid sequence at least about 75% similar to the amino acid sequence of any of SEQ ID NOS:2 and 4. Preferably, the protein encoded by the nucleic acid is at least about 80% identical to any of SEQ ID NOS:2 and 4, more preferably at least about 90%, 95%, 98%, and most preferably at least about 99% identical to SEQ ID NOS:2 and 4. Nonlimiting examples of particular amino acid residues whose codons may changed in a variant nucleic acid molecule are identified as the result of an alignment of an OncoseqX polypeptide with a homologous or paralogous polypeptide, examples of which include the polypeptides encoded by the homologs or paralogs presented in the dendrogram of FIG. 1c (NP_065691. RP42 homolog [gi:10190678]; NP_296372 testis derived transcript 3[gi: 15826860]; AF003894. upstream stimulatory factor 1a mRNA [gi:2197096]; and NP_648777. CG7427-PA [gi:24664675]; and so forth (see FIG. 1c).

An isolated nucleic acid molecule encoding a protein similar to the protein of any of SEQ ID NOS:2 and 4 can be created by introducing one or more nucleotide substitutions, additions or deletions into the corresponding nucleotide sequence, such that one or more amino acid substitutions, additions or deletions are introduced into the encoded protein.

Preferably, conservative amino acid substitutions are made at one or more predicted nonessential amino acid residues. A "conservative amino acid substitution" is one in which the amino acid residue is replaced with an amino acid residue having a similar side chain. Families of amino acid residues having similar side chains have been defined in the art. Certain amino acids have side chains with more than one classifiable characteristic, such as polar amino acid with a long aliphatic side chain. These families include amino acids with basic side chains (e.g., lysine, arginine, histidine), acidic side chains (e.g., aspartic acid, glutamic acid), uncharged polar side chains (e.g., asparagine, glutamine, serine, threonine, tyrosine, tryptophan, cysteine), nonpolar side chains (e.g., glycine, alanine, valine, leucine, isoleucine, proline, phenylalanine, methionine, tyrosine, tryptophan, lysine), beta-branched side chains (e.g., threonine, valine, isoleucine) aromatic side chains (e.g., tyrosine, phenylalanine, tryptophan, histidine) and metal-complexing side chains (e.g., aspartic acid, glutamic acid, asparagine, glutamine, serine, threonine, tyrosine, cysteine, methionine and histidine). Thus, a predicted nonessential amino acid residue in an Oncoseq protein is replaced with another amino acid residue from the same side chain family. Mutations can be introduced into SEQ ID NOS:1 and 3 by standard techniques, such as site-directed mutagenesis and PCR-mediated mutagenesis. Alternatively, in another embodiment, mutations can be introduced randomly along all or part of an Oncoseq coding sequence, such as by saturation mutagenesis, and the resultant mutants can be screened for Oncoseq protein biological activity to identify mutants that retain activity. Following mutagenesis of SEQ ID NOS:1 and 3 the encoded protein can be expressed by any recombinant technology known in the art and the activity of the protein can be determined.

In one embodiment, a variant Oncoseq protein can be assayed for (1) the ability to form protein:protein interactions with other Oncoseq proteins, other cell-surface proteins, or biologically active portions thereof, (2) complex formation between a variant Oncoseq protein and an Oncoseq protein receptor; (3) the ability of a variant Oncoseq protein to bind to an intracellular target protein or biologically active portion thereof; (e.g., avidin proteins); (4) the ability to bind BRA protein; or (5) the ability to specifically bind an anti-Oncoseq protein antibody.

Determining Similarity Between Two or More Sequences

To determine the percent similarity of two amino acid sequences or of two nucleic acids, the sequences are aligned for optimal comparison purposes (e.g., gaps can be introduced in either of the sequences being compared for optimal alignment between the sequences). The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position (i.e., as used herein amino acid or nucleic acid "identity" is equivalent to amino acid or nucleic acid "homology").

The term "sequence identity" refers to the degree to which two polynucleotide or polypeptide sequences are identical on a residue-by-residue basis over a particular region of comparison. The term "percentage of sequence identity" is calculated by comparing two optimally aligned sequences over that region of comparison, determining the number of positions at which the identical nucleic acid base (e.g., A, T or U, C, G, or I, in the case of nucleic acids) occurs in both sequences to yield the number of matched positions, dividing the number of matched positions by the total number of positions in the region of comparison (i.e., the window size), and multiplying the result by 100 to yield the percentage of sequence identity. The term "substantial identity" as used herein denotes a characteristic of a polynucleotide sequence, wherein the polynucleotide comprises a sequence that has at least 80 percent sequence identity, preferably at least 85 percent identity and often 90 to 95 percent sequence identity, more usually at least 99 percent sequence identity as compared to a reference sequence over a comparison region. The term "percentage of positive residues" is calculated by comparing two optimally aligned sequences over that region of comparison, determining the number of positions at which the identical and conservative amino acid substitutions, as defined above, occur in both sequences to yield the number of matched positions, dividing the number of matched positions by the total number of positions in the region of comparison (i.e., the window size), and multiplying the result by 100 to yield the percentage of positive residues.

"Identity," as known in the art, is a relationship between two or more polypeptide sequences or two or more polynucleotide sequences, as determined by, comparing the sequences. In the art, "identity" also means the degree of sequence relatedness between polypeptide or polynucleotide sequences, as the case may be, as determined by the match between strings of such sequences. "Identity" and "similarity" can be readily calculated by known methods, including but not limited to those described in (Computational Molecular Biology, Lesk A. M., ed., Oxford University Press, New York, 1988; Biocomputing: Informatics and Genome Projects, Smith, D. W., ed., Academic Press, New York, 1993; Computer Analysis of Sequence Data, Part I. Griffin, A. M., and Griffin, H. G., eds. Humana Press, New Jersey, 1994; Sequence Analysis in Molecular Biology, von Heinje, G., Academic Press, 1987; and Sequence Analysis Primer, Gribskov, M. and Devereux, J., eds., M Stockton Press New York, 1991; and Carillo, H., and Lipman, D., SIAM J. Applied Math (1988) 48: 1073. Preferred methods to determine identity are designed to give the largest match between the sequences tested. Methods to determine identity and similarity are codified in publicly available computer programs. Preferred computer program methods to determine identity and similarity between two sequences include, but are not limited to, the GCG program package (Devereux, J., et al. (1984) Nucleic Acids Research 12(1): 387), BLASTP, BLASTN, and FASTA (Atschul, S. F. et al. (1990) J. Molec. Biol 215: 403-410. The BLAST X program is publicly available from NCBI and other sources (BLAST Manual, Altschul, S., et al., NCBI NLM NIH Bethesda, Md. 20894; Altschul, S., et al. (1990) J. Mol. Biol 215: 403-410. The well known Smith Waterman algorithm may also be used to determine identity.

Parameters for polypeptide sequence comparison include the following: Algorithm: Needleman and Wunsch, J. Mol Biol. 48: 443-453 (1970).

Comparison matrix BLOSSUM62 from Hentikoff and Hentikoff, (1992) Proc. Natl. Acad. Sci. USA. 89:10915-10919.

Gap Penalty: 12
Gap Length Penalty: 4

A program useful with these parameters is publicly available as the "gap" program from Genetics Computer Group, Madison Wis. The aforementioned parameters are the default parameters for peptide comparisons (along with no penalty for end gaps).

Parameters for polynucleotide comparison include the following: Algorithm: Needleman and Wunsch. J. Mol Biol. 48: 443-453 (1970).

Comparison matrix: matches=+10, mismatch=0
Gap Penalty: 50
Gap Length Penalty: 3

Available as: The "gap" program from Genetics Computer Group, Madison Wis., These are the default parameters for nucleic acid comparisons.

A preferred meaning for "identity" for polynucleotides and polypeptides as the case may be, are provided below.

Polynucleotide embodiments further include an isolated polynucleotide comprising a polynucleotide sequence having at least a 50, 60, 70, 80, 85, 90, 95, 97 or 100% identity to the reference sequence of SEQ ID NO:1 or SEQ ID NO:3, wherein said polynucleotide sequence may be identical to the reference sequence of SEQ ID NO:1 or SEQ ID NO:3, or may include up to a certain integer number of nucleotide alterations as compared to the reference sequence, wherein said alterations are selected from the group consisting of at least one nucleotide deletion, substitution including transition and transversion, or insertion, and wherein said alterations may occur at the 5' or 3' terminal positions of the reference nucleotide sequence or anywhere between those terminal positions interspersed either individually among the nucleotides in the reference sequence or in one or more contiguous groups within the reference sequence, and wherein said number of nucleotide alterations is determined by multiplying the total number of nucleotides in SEQ ID NO:1 or SEQ ID NO:3 by the integer defining the percent identity divided by 100 and then subtracting that product from said total number of nucleotides in SEQ ID NO:1 or SEQ ID NO:3, or:

$$n_n \leq x_n - (x_n \cdot y)$$

wherein $n_n$ is the number of nucleotide alterations, $x_n$ is the total number of nucleotides in SEQ ID NO:1 or SEQ ID NO:3, y is 0.50 for 50%, 0.60 for 60%, 0.70 for 70%, 0.80 for 80%, 0.85 for 85% 0.90 for 90%, 0.95 for 95%. 0.97 for 97% or 10.00 for 100%, and · is the symbol for the multiplication operator, and wherein any non-integer product of $x_n$ and y is rounded down to the nearest integer prior to subtracting it from $x_n$. Alterations of a polynucleotide sequence encoding the polypeptide of SEQ ID NO:2 or SEQ ID NO:4 may create nonsense, missense or frameshift mutations in this coding sequence and thereby alter the polypeptide encoded by the polynucleotide following such alterations.

Additionally the BLAST alignment tool is useful for detecting similarities and percent identity between two sequences. BLAST is available on the World Wide Web at the National Center for Biotechnology Information site. References describing BLAST analysis include Madden, T. L., Tatusov, R. L. & Zhang, J. (1996) Meth. Enzymol. 266:131-141; Altschul, S. F., Madden, T. L., Schäffer, A. A., Zhang, J., Zhang, Z., Miller, W. & Lipman, D. J. (1997) Nucleic Acids Res. 25:3389-3402; and Zhang, J. & Madden, T. L. (1997) Genome Res. 7:649-656.

Antisense Nucleic Acids

Another aspect of the invention pertains to isolated antisense nucleic acid molecules that are hybridizable to or complementary to the nucleic acid molecule comprising the nucleotide sequence of SEQ ID NOS:1 and 3, or fragments, analogs or derivatives thereof. An "antisense" nucleic acid comprises a nucleotide sequence that is complementary to a "sense" nucleic acid encoding a protein, e.g., complementary to the coding strand of a double-stranded cDNA molecule or complementary to an mRNA sequence. In specific aspects, antisense nucleic acid molecules are provided that comprise a sequence complementary to at least about 10, 25, 50, 100, 250 or 500 nucleotides or an entire Oncoseq coding strand, or to only a portion thereof Nucleic acid molecules encoding fragments, homologs, derivatives and analogs of an Oncoseq protein of any of SEQ ID NOS:2 and 4 or antisense nucleic acids complementary to an Oncoseq nucleic acid sequence of SEQ ID NOS:1 and 3 are additionally provided.

In one embodiment, an antisense nucleic acid molecule is antisense to a "coding region" of the coding strand of a nucleotide sequence encoding an Oncoseq protein. The term "coding region" refers to the region of the nucleotide sequence comprising codons which are translated into amino acid residues (e.g., the protein coding region of a human Oncoseq protein that corresponds to any of SEQ ID NOS:2 and 4). In another embodiment, the antisense nucleic acid molecule is antisense to a "noncoding region" of the coding strand of a nucleotide sequence encoding an Oncoseq protein. The term "noncoding region" refers to 5' and 3' sequences which flank the coding region that are not translated into amino acids (i.e., also referred to as 5' and 3' untranslated regions), but that may contain sequences regulating expression.

Given the coding strand sequences encoding an Oncoseq protein disclosed herein (e.g., SEQ ID NOS:1 and 3), antisense nucleic acids of the invention can be designed according to the rules of Watson and Crick or Hoogsteen base pairing. The antisense nucleic acid molecule can be complementary to the entire coding region of an Oncoseq mRNA, but more preferably is an oligonucleotide that is antisense to only a portion of the coding or noncoding region of an Oncoseq mRNA. For example, the antisense oligonucleotide can be complementary to the region surrounding the translation start site of the Oncoseq mRNA. An antisense oligonucleotide can be, for example, about 5, 10, 15, 20, 25, 30, 35, 40, 45 or 50 nucleotides in length. An antisense nucleic acid of the invention can be constructed using chemical synthesis or enzymatic ligation reactions using procedures known in the art. For example, an antisense nucleic acid (e.g., an antisense oligonucleotide) can be chemically synthesized using naturally occurring nucleotides or variously modified nucleotides designed to increase the biological stability of the molecules or to increase the physical stability of the duplex formed between the antisense and sense nucleic acids, e.g., phosphorothioate derivatives aid acridine substituted nucleotides can be used. Alternatively, the antisense nucleic acid can be produced biologically using an expression vector into which a nucleic acid has been subcloned in an antisense orientation (I.e., RNA transcribed from the inserted nucleic acid will be of an antisense orientation to a target nucleic acid of interest, described further in the following subsection).

The antisense nucleic acid molecules of the invention are typically administered to a subject or generated in situ such that they hybridize with or bind to cellular mRNA and/or genomic DNA encoding an Oncoseq protein to thereby inhibit expression of the protein, e.g., by inhibiting transcription and/or translation. The hybridization can be by conventional nucleotide complementarity to form a stable duplex, or, for example, in the case of an antisense nucleic acid molecule that binds to DNA duplexes, through specific interactions in the major groove of the double helix. An example of a route of administration of antisense nucleic acid molecules of the invention includes direct injection at a tissue site. Alternatively, antisense nucleic acid molecules can be modified to target selected cells and then administered systemically. For example, for systemic administration, antisense molecules can be modified such that they specifically bind to receptors or antigens expressed on a selected cell surface, e.g., by linking the antisense nucleic acid molecules to peptides or antibodies that bind to cell surface receptors or antigens. The antisense nucleic acid molecules can also be delivered to cells using the vectors described herein. To achieve sufficient intracellular concentrations of antisense molecules, vector constructs in which the antisense nucleic acid molecule is placed under the control of a strong pol II or pol III promoter are generally preferred.

In yet another embodiment, the antisense nucleic acid molecule of the invention is an a-anomeric nucleic acid molecule. An α-anomeric nucleic acid molecule forms specific double-stranded hybrids with complementary RNA in which, contrary to the usual β-units, the strands run parallel to each other (Gaultier et al. (1987) *Nucleic Acids Res* 15: 6625-6641). The antisense nucleic acid molecule can also comprise a 2'-O-methylribonucleotide (Inoue et al. (1987) *Nucleic Acids Res* 15: 6131-6148) or a chimeric RNA-DNA analogue (Inoue et al. (1987) *FEBS Lett* 215: 327-330).

Interfering RNA

In one aspect of the invention, Oncoseq gene expression can be attenuated by RNA interference. One approach well-known in the art is short interfering RNA (siRNA) or micro RNA (also designated as an interfering polynucleotide or a micro polynucleotide herein) mediated gene silencing where expression products of an Oncoseq gene are targeted by specific double stranded Oncoseq derived siRNA nucleotide sequences that are complementary to at least a 19-25 nt long segment of the Oncoseq gene transcript, including the 5' untranslated (UT) region, the ORF, or the 3' UT region. See, e.g., PCT applications WO00/44895, WO99/32619, WO01/75164, WO01/92513, WO01/29058, WO01/89304, WO02/16620, and WO02/29858, each incorporated by reference herein in their entirety. Targeted genes can be an Oncoseq gene, or an upstream or downstream modulator of the Oncoseq gene. Nonlimiting examples of upstream or downstream modulators of an Oncoseq gene include, e.g., a transcription factor that binds the Oncoseq gene promoter, a kinase or phosphatase that interacts with an Oncoseq polypeptide, and polypeptides involved in an Oncoseq regulatory pathway.

According to the methods of the present invention, Oncoseq gene expression is silenced using short interfering RNA. An Oncoseq polynucleotide according to the invention includes a siRNA polynucleotide. Such an Oncoseq siRNA can be obtained using an Oncoseq polynucleotide sequence, for example, by processing the Oncoseq ribopolynucleotide sequence in a cell-free system, such as but not limited to a *Drosophila* extract or by transcription of recombinant double stranded Oncoseq RNA or by chemical synthesis of nucleotide sequences similar to an Oncoseq sequence. See, e.g., Tuschl, Zamore, Lehmann, Bartel and Sharp (1999), Genes & Dev. 13: 3191-3197, incorporated herein by reference in its entirety. When synthesized, a typical 0.2 micromolar-scale RNA synthesis provides about 1 milligram of siRNA, which is sufficient for 1000 transfection experiments using a 24-well tissue culture plate format.

The most efficient silencing is generally observed with siRNA duplexes composed of a 21-nt sense strand and a 21-nt antisense strand, paired in a manner to have a 2-nt 3' overhang. The sequence of the 2-nt 3' overhang makes an additional small contribution to the specificity of siRNA target recognition. The contribution to specificity is localized to the unpaired nucleotide adjacent to the first paired bases. In one embodiment, the nucleotides in the 3' overhang are ribonucleotides. In an alternative embodiment, the nucleotides in the 3' overhang are deoxyribonucleotides. Using 2'-deoxyribonucleotides in the 3' overhangs is as efficient as using ribonucleotides, but deoxyribonucleotides are often cheaper to synthesize and are most likely more nuclease resistant.

A contemplated recombinant expression vector of the invention comprises an Oncoseq DNA molecule cloned into an expression vector comprising operatively-linked regulatory sequences flanking the Oncoseq sequence in a manner that allows for expression (by transcription of the DNA molecule) of both strands. An RNA molecule that is antisense to Oncoseq mRNA is transcribed by a first promoter (e.g., a promoter sequence 3' of the cloned DNA) and an RNA molecule that is the sense strand for the Oncoseq mRNA is transcribed by a second promoter (e.g., a promoter sequence 5' of the cloned DNA). The sense and antisense strands may hybridize in vivo to generate siRNA constructs for silencing of the Oncoseq gene. Alternatively, two constructs can be utilized to create the sense and anti-sense strands of a siRNA construct. Finally, cloned DNA can encode a construct having secondary structure, wherein a single transcript has both the sense and complementary antisense sequences from the target gene or genes. In an example of this embodiment, a hairpin RNAi product is similar to all or a portion of the target gene In another example, a hairpin RNAi product is a siRNA. The regulatory sequences flanking the Oncoseq sequence may be identical or may be different, such that their expression may be modulated independently, or in a temporal or spatial manner.

In a specific embodiment, siRNAs are transcribed intracellularly by cloning the Oncoseq gene templates into a vector containing, e.g., a RNA pol III transcription unit from the smaller nuclear RNA (snRNA) U6, or the human RNase P RNA H1. One example of a vector system is the GeneSuppressor™ RNA Interference kit (commercially available from Imgenex). The U6 and H1 promoters are members of the type III class of Pol III promoters. The +1 nucleotide of the U6-like promoters is always guanosine, whereas the +1 for H1 promoters is adenosine. The termination signal for these promoters is defined by five consecutive thymidines. The transcript is typically cleaved after the second uridine Cleavage at this position generates a 3' UU overhang in the expressed siRNA, which is similar to the 3' overhangs of synthetic siRNAs. Any sequence less than 400 nucleotides in length can be transcribed by these promoter, therefore they are ideally suited for the expression of around 21-nucleotide siRNAs in, e.g., an approximately 50-nucleotide RNA stem-loop transcript.

A siRNA vector appears to have an advantage over synthetic siRNAs where long term knock-down of expression is desired. Cells transfected with a siRNA expression vector would experience steady, long-term mRNA inhibition. In contrast, cells transfected with exogenous synthetic siRNAs typically recover from mRNA suppression within seven days or ten rounds of cell division. The long-term gene silencing ability of siRNA expression vectors may provide for applications in gene therapy.

In general, siRNAs are chopped from longer dsRNA by an ATP-dependent ribonuclease called DICER. DICER is a member of the RNase III family of double-stranded RNA-specific endonucleases. The siRNAs assemble with cellular proteins into an endonuclease complex. In vitro studies in *Drosophila* suggest that the siRNAs/protein complex (siRNP) is then transferred to a second enzyme-complex, called an RNA-induced silencing complex (RISC), which contains an endoribonuclease that is distinct from DICER. RISC uses the sequence encoded by the antisense siRNA strand to find and destroy mRNAs of complementary sequence. The siRNA thus acts as a guide, restricting the ribonuclease to cleave only mRNAs complementary to one of the two siRNA strands.

An Oncoseq mRNA region to be targeted by siRNA is generally selected from a desired Oncoseq sequence beginning 50 to 100 nt downstream of the start codon. Alternatively, 5' or 3' UTRs and regions nearby the start codon can be used but are generally avoided, as these may be richer in regulatory protein binding sites. UTR-binding proteins and/or translation initiation complexes may interfere with binding of the siRNP or RISC endonuclease complex. An initial BLAST homology search for the selected siRNA sequence is done against an available nucleotide sequence library to ensure that only one gene is targeted Specificity of target recognition by siRNA duplexes indicate that a single point mutation located in the paired region of an siRNA duplex is sufficient to abolish target mRNA degradation. See, Elbashir et al. 2001 EMBO J. 20(23):6877-88. Hence, consideration should be taken to accommodate SNPs, polymorphisms, allelic variants or species-specific variations when targeting a desired gene.

In one embodiment, a complete Oncoseq siRNA experiment includes the proper negative control. A negative control siRNA generally has the same nucleotide composition as the Oncoseq siRNA but lack significant sequence homology to the genome. Typically, one would scramble the nucleotide sequence of the Oncoseq siRNA and do a homology search to make sure it lacks homology to any other gene.

Two independent Oncoseq siRNA duplexes can be used to knock-down a target Oncoseq gene. This helps to control for specificity of the silencing effect. In addition, expression of two independent genes can be simultaneously knocked down by using equal concentrations of different Oncoseq siRNA duplexes, e.g., an Oncoseq siRNA and an siRNA for a regulator of an Oncoseq gene or polypeptide. Availability of siRNA-associating proteins is believed to be more limiting than target mRNA accessibility.

A targeted Oncoseq region is typically a sequence of two adenines (AA) and two thymidines (TT) divided by a spacer region of nineteen (N19) residues (e.g., AA(N19)TT). A desirable spacer region has a G/C-content of approximately 30% to 70%, and more preferably of about 50%. If the sequence AA(N19)TT is not present in the target sequence, an alternative target region would be AA(N21). The sequence of the Oncoseq sense siRNA corresponds to (N 19}TT or N21, respectively. In the latter case, conversion of the 3' end of the sense siRNA to TT can be performed if such a sequence does not naturally occur in the Oncoseq polynucleotide. The rationale for this sequence conversion is to generate a symmetric duplex with respect to the sequence composition of the sense and antisense 3' overhangs. Symmetric 3' overhangs may help to ensure that the siRNPs are formed with approximately equal ratios of sense and antisense target RNA-cleaving siRNPs. See, e.g., Elbashir, Lendeckel and Tuschl (2001). Genes & Dev. 15: 188-200, incorporated by reference herein in its entirely. The modification of the overhang of the sense sequence of the siRNA duplex is not expected to affect targeted mRNA recognition, as the antisense siRNA strand guides target recognition.

Alternatively, if the Oncoseq target mRNA does not contain a suitable AA(N21) sequence, one may search for the sequence NA(N21). Further, the sequence of the sense strand and antisense strand may still be synthesized as 5' (N19)TT, as it is believed that the sequence of the 3'-most nucleotide of the antisense siRNA does not contribute to specificity. Unlike antisense or ribozyme technology, the secondary structure of the target mRNA does not appear to have a strong effect on silencing. See, Harborth, et al. (2001) J. Cell Science 114: 4557-4565, incorporated by reference in its entirety.

Transfection of Oncoseq siRNA duplexes can he achieved using standard nucleic acid transfection methods, for example, OLIGOFECTAMINE Reagent (commercially available from Invitrogen). An assay for Oncoseq gene silencing is generally performed approximately 2 days after transfection. No Oncoseq gene silencing has been observed in the absence of transfection reagent, allowing for a comparative analysis of the wild-type and silenced Oncoseq phenotypes. In a specific embodiment, for one well of a 24-well plate, approximately 0.84 μg of the siRNA duplex is generally sufficient. Cells are typically seeded the previous day, and are transfected at about 50% confluence. The choice of cell culture media and conditions are routine to those of skill in the art, and will vary with the choice of cell type. The efficiency of transfection may depend on the cell type, but also on the passage number and the confluency of the cells. The time and the manner of formation of siRNA-liposome complexes (e.g. inversion versus vortexing) are also critical. Low transfection efficiencies are the most frequent cause of unsuccessful Oncoseq silencing. The efficiency of transfection needs to be carefully examined for each new cell line to be used. Preferred cell are derived from a mammal, more preferably from a rodent such as a rat or mouse, and most preferably from a human. Where used for therapeutic treatment, the cells are preferentially autologous, although non-autologous cell sources are also contemplated as within the scope of the present invention.

For a control experiment, transfection of 0.84 µg single-stranded sense Oncoseq siRNA will have no effect on Oncoseq silencing, and 0.84 µg antisense siRNA has a weak silencing effect when compared to 0.84 µg of duplex siRNAs. Control experiments again allow for a comparative analysis of the wild-type and silenced Oncoseq phenotypes. To control for transfection efficiency, targeting of common proteins is typically performed, for example targeting of lamin A/C or transfection of a CMV-driven EGFP-expression plasmid (e.g. commercially available from Clontech). In the above example, a determination of the fraction of lamin A/C knockdown in cells is determined the next day by such techniques as immunofluorescence, Western blot, Northern blot or other similar assays for protein expression or gene expression. Lamin A/C monoclonal antibodies may be obtained from Santa Cruz Biotechnology.

Depending on the abundance and the half life (or turn-over) of the targeted Oncoseq polynucleotide in a cell, a knock-down phenotype may become apparent after 1 to 3 days, or even later. In cases where no Oncoseq knock-down phenotype is observed, depletion of the Oncoseq polynucleotide may be observed by immunofluorescence or Western blotting. If the Oncoseq polynucleotide is still abundant after 3 days, cells need to be split and transferred to a fresh 24-well plate for re-transfection. If no knock-down of the targeted protein is observed it may be desirable to analyze whether the target mRNA (Oncoseq or an Oncoseq upstream or downstream gene) was effectively destroyed by the transfected siRNA duplex. Two days after transfection, total RNA is prepared, reverse transcribed using a target-specific primer, and PCR-amplified with a primer pair covering at least one exon-exon junction in order to control for amplification of pre-mRNAs. RT/PCR of a non-targeted mRNA is also needed as control. Effective depletion of the mRNA yet undetectable reduction of target protein may indicate that a large reservoir of stable Oncoseq protein may exist in the cell. Multiple transfection in sufficiently long intervals may be necessary until the target protein is finally depleted to a point where a phenotype may become apparent. If multiple transfection steps are required, cells are split 2 to 3 days after transfection The cells may be transfected immediately after splitting.

An inventive therapeutic method of the invention contemplates administering an Oncoseq siRNA construct as therapy to compensate for increased or aberrant Oncoseq expression or activity. The Oncoseq ribopolynucleotide is obtained and processed into siRNA fragments, or an Oncoseq siRNA is synthesized, as described above. The Oncoseq siRNA is administered to cells or tissues using known nucleic acid transfection techniques, as described above. An Oncoseq siRNA specific for an Oncoseq gene will decrease or knockdown Oncoseq transcription products, which will lead to reduced Oncoseq polypeptide production, resulting in reduced Oncoseq polypeptide activity in the cells or tissues.

The present invention also encompasses a method of treating a disease or condition associated with the presence of an Oncoseq protein in an individual comprising administering to the individual an RNAi construct that targets the mRNA of the protein (the mRNA that encodes the protein) for degradation. A specific RNAi construct includes a siRNA or a double stranded gene transcript that is processed into siRNAs. Upon treatment, the target protein is not produced or is not produced to the extent it would be in the absence of the treatment.

Where the Oncoseq gene function is not correlated with a known phenotype, a control sample of cells or tissues from healthy individuals provides a reference standard for determining Oncoseq expression levels. Expression levels are detected using the assays described, e.g., RT-PCR, Northern blotting, Western blotting, ELISA, and the like. A subject sample of cells or tissues is taken from a mammal, preferably a human subject, suffering from a disease state. The Oncoseq ribopolynucleotide is used to produce siRNA constructs, that are specific for the Oncoseq gene product. These cells or tissues are treated by administering Oncoseq siRNA's to the cells or tissues by methods described for the transfection of nucleic acids into a cell or tissue, and a change in Oncoseq polypeptide or polynucleotide expression is observed in the subject sample relative to the control sample, using the assays described. This Oncoseq gene knockdown approach provides a rapid method for determination of an Oncoseq minus (Oncoseq⁻) phenotype in the treated subject sample. The Oncoseq⁻ phenotype observed in the treated subject sample thus serves as a marker for monitoring the course of a disease state during treatment.

In specific embodiments, an Oncoseq siRNA is used in therapy. Methods for the generation and use of an Oncoseq siRNA are known to those skilled in the art. Example techniques are provided below.

Production of RNAs

Sense RNA (ssRNA) and antisense RNA (asRNA) of Oncoseq are produced using known methods such as transcription in RNA expression vectors. In the initial experiments, the sense and antisense RNA are about 500 bases in length each. The produced ssRNA and asRNA (0.5 µM) in 10 mM Tris-HCl (pH 7.5) with 20 mM NaCl were heated to 95° C. for 1 min then cooled and annealed at room temperature for 12 to 16 h. The RNAs are precipitated and resuspended in lysis buffer (below). To monitor annealing, RNAs are electrophoresed in a 2% agarose gel in TBE buffer and stained with ethidium bromide. See, e.g., Sambrook et al., Molecular Cloning. Cold Spring Harbor Laboratory Press, Plainview, N.Y. (1989).

Lysate Preparation

Untreated rabbit reticulocyte lysate (Ambion) are assembled according to the manufacturer's directions. dsRNA is incubated in the lysate at 30° C. for 10 min prior to the addition of mRNAs. Then Oncoseq mRNAs are added and the incubation continued for an additional 60 min. The molar ratio of double stranded RNA and mRNA is about 200:1. The Oncoseq mRNA is radiolabeled (using known techniques) and its stability is monitored by gel electrophoresis.

In a parallel experiment made with the same conditions, the double stranded RNA is internally radiolabeled with a $^{32}$P-ATP. Reactions are stopped by the addition of 2x proteinase K buffer and deproteinized as described previously (Tuschl et al. (1999) Genes Dev., 13:3191-3197). Products are analyzed by electrophoresis in 15% or 18% polyacrylamide sequencing gels using appropriated RNA standards. By monitoring the gels for radioactivity, the natural production of 10 to 25 nt RNAs from the double stranded RNA can be determined.

The band of double stranded RNA, about 21-23 bps, is eluted. The efficacy of these 21-23 mers for suppressing Oncoseq transcription is assayed in vitro using the same rabbit reticulocyte assay described above using 50 nanomolar of double stranded 21-23 mer for each assay. The sequence of these 21-23 mers is then determined using standard nucleic acid sequencing techniques.

RNA Preparation 21 nt RNAs, based on the sequence determined above, are chemically synthesized using Expedite RNA phosphoramidites and thymidine phosphoramtidite (Proligo, Germany). Synthetic oligonucleotides are deprotected and gel-purified (Elbashir et al. (2001) Genes & Dev. 15, 188-200), followed by Sep-Pak C18 cartridge (Waters, Milford, Mass., USA) purification (Tuschl et al. (1993) Biochemistry, 32:11658-11668).

These RNAs (20 μM) single strands are incubated in annealing buffer (100 mM potassium acetate, 30 mM HEPES-KOH at pH 7.4, 2 mM magnesium acetate) for 1 min at 90° C. followed by 1 h at 37° C.

Cell Culture

A cell culture known in the art to regularly express Oncoseq is propagated using standard conditions. 24 hours before transfection, at approx. 80% confluency, the cells are trypsinized and diluted 1:5 with fresh medium without antibiotics (1-3×10$^5$ cells/ml) and transferred to 24-well plates (500 ml/well). Transfection is performed using a commercially available lipofection kit and Oncoseq expression is monitored using standard techniques with positive and negative control. A positive control is cells that naturally express Oncoseq while a negative control is cells that do not express Oncoseq. Base-paired 21 and 22 nt siRNAs with overhanging 3' ends mediate efficient sequence-specific mRNA degradation in lysates and in cell culture. Different concentrations of siRNAs are used. An efficient concentration for suppression in vitro in mammalian culture is between 25 nM to 100 nM final concentration. This indicates that siRNAs are effective at concentrations that are several orders of magnitude below the concentrations applied in conventional antisense or ribozyme gene targeting experiments.

The above method provides a way both for the deduction of Oncoseq siRNA sequence and the use of such siRNA for in vitro suppression. In vivo suppression may be performed using the same siRNA using well known in vivo transfection or gene therapy transfection techniques.

Ribozymes and PNA Moieties

Such modifications include, by way of non limiting example, modified bases, and nucleic acids whose sugar phosphate backbones are modified or derivatized. These modifications are carried out at least in part to enhance the chemical stability of the modified nucleic acid, such that they may be used, for example, as antisense binding nucleic acids in therapeutic applications in a subject.

In still another embodiment, an antisense nucleic acid of the invention is a ribozyme. Ribozymes are catalytic RNA molecules with ribonuclease activity that are capable of cleaving a single-stranded nucleic acid, such as an mRNA, to which they have a complementary region. Thus, ribozymes (e.g., hammerhead ribozymes (described in Haselhoff and Gerlach (1988) *Nature* 334:585-591)) can be used to catalytically cleave the Oncoseq protein mRNA transcripts to thereby inhibit translation of the Oncoseq protein mRNA. A ribozyme having specificity for an Oncoseq protein-encoding nucleic acid can be designed based upon the nucleotide sequence of an Oncoseq DNA disclosed herein (i.e., SEQ ID NOS:1 and 3). For example, a derivative of a Tetrahymena L-19 IVS RNA can be constructed in which the nucleotide sequence of the active site is complementary to the nucleotide sequence to he cleaved in an Oncoseq protein-encoding mRNA. See, e.g., Cech et al. U.S. Pat No 4,987,071; and Cech et al. U.S. Pat. No. 5,116,742. Alternatively, an Oncoseq mRNA can be used to select a catalytic RNA having a specific ribonuclease activity from a pool of RNA molecules. See, e.g., Bartel et al., (1993) *Science* 261:1411-1418.

Alternatively, Oncoseq gene expression can be inhibited by targeting nucleotide sequences complementary to the regulatory region of the Oncoseq gene (e.g., the Oncoseq gene promoter and/or enhancers) to form triple helical structures that prevent transcription of the Oncoseq gene in target cells. See generally, Helene (1991) *Anticancer Drug Des.* 6: 569-84; Helene et al. (1992) *Ann. N.Y. Acad. Sci.* 660:27-36; and Maher (1992) *Bioassays* 14: 807-15.

In various embodiments, the Oncoseq nucleic acids can be modified at the base moiety, sugar moiety or phosphate backbone to improve, e.g., the stability, hybridization, or solubility of the molecule. For example, the deoxyribose-phosphate backbone of the nucleic acids can be modified to generate peptide nucleic acids (see Hyrup et al. (1996) *Bioorg Med Chem* 4: 5-23). As used herein, the terms "peptide nucleic acids" or "PNAs" refer to nucleic acid mimics, e.g., DNA mimics, in which the deoxyribosephosphate backbone is replaced by a pseudopeptide backbone and only the four natural nucleobases are retained. The neutral backbone of PNAs has been shown to allow for specific hybridization to DNA and RNA under conditions of low ionic strength. The synthesis of PNA oligomers can be performed using standard solid phase peptide synthesis protocols as described in Hyrup et al. (1996) above; Perry-O'Keefe et al. (1996) *Proc. Natl. Acad. Sci. USA* 93: 14670-675.

PNAs of the Oncoseqs can be used in therapeutic and diagnostic applications. For example, PNAs can be used as antisense or anti-gene agents for sequence-specific modulation of gene expression by, e.g., inducing transcription or translation arrest or inhibiting replication. PNAs of the Oncoseq proteins can also be used, e.g., in the analysis of single base pair mutations in a gene by, e.g., PNA directed PCR clamping; as artificial restriction enzymes when used in combination with other enzymes, e.g., S1 nucleases (Hyrup B. (1996) above); or as probes or primers for DNA sequence and hybridization (Hyrup et al. (1996), above; Perry-O'Keefe (1996), above).

In another embodiment, PNAs of the Oncoseq proteins can be modified, e.g., to enhance their stability or cellular uptake, by attaching lipophilic or other helper groups to PNA, by the formation of PNA-DNA chimeras, or by the use of liposomes or other techniques of drug delivery known in the art. For example, PNA-DNA chimeras of the Oncoseq sequences can be generated that may combine the advantageous properties of PNA and DNA. Such chimeras allow DNA recognition enzymes, e.g., RNase H and DNA polymerases, to interact with the DNA portion while the PNA portion would provide high binding affinity and specificity. PNA-DNA chimeras can be linked using linkers of appropriate lengths selected in terms of base stacking, number of bonds between the nucleobases, and orientation (Hyrup (1996) above). The synthesis of PNA-DNA chimeras can be performed as described in Hyrup (1996) above and Finn et al. (1996) *Nucl Acids Res* 24: 3357-63. For example, a DNA chain can be synthesized on a solid support using standard phosphoramidite coupling chemistry, and modified nucleoside analogs, e.g., 5'-(4-methoxytrityl)amino-5'-deoxy-thymidine phosphoramidite, can be used between the PNA and the 5' end of DNA (Mag et al. (1989) *Nucl Acid Res* 17: 5973-88). PNA monomers are then coupled in a stepwise manner to produce a chimeric molecule with a 5' PNA segment and a 3' DNA segment (Finn et al. (1996) above). Alternatively, chimeric molecules can be synthesized with a 5' DNA segment and a 3' PNA segment. See, Petersen et al. (1975) *Bioorg Med Chem Lett* 5:1119-11124.

In other embodiments, the oligonucleotide may include other appended groups such as peptides (e.g., for targeting host cell receptors in vivo), or agents facilitating transport across the cell membrane (see, e.g., Letsinger et al., 1989, *Proc. Natl. Acad. Sci. U.S.A.*, 86:6553-6556; Lemaitre et al., 1987, *Proc. Natl. Acad. Sci.* 84:648-652; PCT Publication No. WO88/09810) or the blood-brain barrier (see, e.g., PCT Publication No. WO89/10134). In addition, oligonucleotides can be modified with hybridization triggered cleavage agents (See, e.g., Krol et al., 1988, *BioTechniques* 6:958-976) or intercalating agents. (See, e.g., Zon, 1988, *Pharm. Res.* 5: 539-549). To this end, the oligonucleotide may be conjugated to another molecule, e.g., a peptide, a hybridization triggered cross-linking agent, a transport agent, a hybridization-triggered cleavage agent, etc.

Proteins and Polypeptides

The novel protein of the invention includes the Oncoseq protein-like protein whose sequence is provided in any of SEQ ID NOS:2 and 4. The invention also includes a mutant or variant protein any of whose residues may be changed from the corresponding residue shown in FIG. 1 while still encoding a protein that maintains its Oncoseq protein-like activities and physiological functions, or a functional fragment thereof. For example, the invention includes the polypeptides encoded by the variant Oncoseq nucleic acids described above. In the mutant or variant protein, up to 20% or more of the residues may be so changed.

In general, an Oncoseq protein-like variant that preserves Oncoseq protein-like function includes any variant in which residues at a particular position in the sequence have been substituted by other amino acids, and further include the possibility of inserting an additional residue or residues between two residues of the parent protein as well as the possibility of deleting one or more residues from the parent sequence. Any amino acid substitution, insertion, or deletion is encompassed by the invention. In favorable circumstances, the substitution is a conservative substitution as defined above. Furthermore, without limiting the scope of the invention, positions of any of SEQ ID NOS:2 and 4 may be substitute such that a mutant or variant protein may include one or more substitutions.

The invention also includes isolated Oncoseq proteins, and biologically active portions thereof, or derivatives, fragments, analogs or homologs thereof. Also provided are polypeptide fragments suitable for use as immunogens to raise anti-Oncoseq protein antibodies. In one embodiment, native Oncoseq proteins can be isolated from cells or tissue sources by an appropriate purification scheme using standard protein purification techniques. In another embodiment, Oncoseq proteins are produced by recombinant DNA techniques. Alternative to recombinant expression, an Oncoseq protein or polypeptide can be synthesized chemically using standard peptide synthesis techniques. Purification of proteins and polypeptides is described, for example, in texts such as "Protein Purification, 3$^{rd}$ Ed.", R. K. Scopes, Springer-Verlag, New York, 1994; "Protein Methods, 2$^{nd}$ Ed". D. M. Bollag, M. D. Rozycki, and S. J. Edelsterin, Wiley-Liss, New York, 1996; and "Guide to Protein Purification"; M. Deutscher, Academic Press, New York, 2001.

Biologically active portions of an Oncoseq protein include peptides comprising amino acid sequences sufficiently similar to or derived from the amino acid sequence of the Oncoseq protein, e.g., the amino acid sequence shown in SEQ ID NOs:2 and 4 that include fewer amino acids than the fill length Oncoseq proteins, and exhibit at least one activity of an Oncoseq protein. Typically, biologically active portions comprise a domain or motif with at least one activity of the Oncoseq protein. A biologically active portion of an Oncoseq protein can be a polypeptide which is, for example, 10, 25, 50, 100 or more amino acids in length.

A biologically active portion of an Oncoseq protein of the present invention may contain at least one of the above-identified domains conserved among the Oncoseq family of proteins. Moreover, other biologically active portions, in which other regions of the protein are deleted, can be prepared by recombinant techniques and evaluated for one or more of the functional activities of a native Oncoseq protein.

In an embodiment, the Oncoseq protein has an amino acid sequence shown in any of SEQ ID NOS:2 and 4. In other embodiments, the Oncoseq protein is substantially similar to any of SEQ ID NOS:2 and 4 and retains the functional activity of the protein of any of SEQ ID NOS:2 and 4, yet differs in amino acid sequence due to natural allelic variation or mutagenesis, as described in detail below. Accordingly, in another embodiment, the Oncoseq protein is a protein that comprises an amino acid sequence at least about 45% similar, and more preferably about 55, 65, 70, 75, 80, 85, 90, 95, 98 or even 99% similar to the amino acid sequence of any of SEQ ID NOS:2 and 4 and retains the functional activity of the Oncoseq proteins of the corresponding polypeptide having the sequence of SEQ ID NOS:2 and 4. Nonlimiting examples of particular amino acid residues that may changed in a variant polypeptide molecule are identified as the result of an alignment of an OncoseqX polypeptide with a homologous or paralogous polypeptide, examples of which include the polypeptides encoded by the homologs or paralogs presented in the dendrogram of FIG. 1c NP_065691 RP42 homolog [gi: 10190678]; NP_296372 testis derived transcript 3[gi:15826860]; AF003894 upstream stimulatory factor 1a mRNA [gi: 2197096]; and NP_648777. C67427-PA [gi:24664675]; and so forth (see FIG. 1c).

Chimeric and Fusion Proteins

The invention also provides Oncoseq protein chimeric or fusion proteins. As used herein, an Oncoseq protein "chimeric protein" or "fusion protein" includes an Oncoseq polypeptide operatively linked to a non-Oncoseq polypeptide. A "Oncoseq polypeptide" refers to a polypeptide having an amino acid sequence corresponding to the Oncoseq protein, whereas a "non-Oncoseq polypeptide" refers to a polypeptide having an amino acid sequence corresponding to a protein that is not substantially similar to the Oncoseq protein, e.g., a protein that is different from the Oncoseq protein and that is derived from the same or a different organism. Within a fusion protein containing an Oncoseq protein the Oncoseq polypeptide can correspond to all or a portion of an Oncoseq protein. In one embodiment, an Oncoseq protein fusion protein comprises a full length Oncoseq protein or at least one biologically active fragment of an Oncoseq protein. In another embodiment, an Oncoseq protein fusion protein comprises at least two fragments of an Oncoseq protein each of which retains its biological activity. Within the fusion protein, the term "operatively linked" is intended to indicate that the Oncoseq polypeptide and the non-Oncoseq polypeptide are fused in-frame to each other. The non-Oncoseq polypeptide can be fused to the N-terminus or C-terminus of the Oncoseq polypeptide.

For example, in one embodiment an Oncoseq protein fusion protein comprises an Oncoseq polypeptide operably linked to the extracellular domain of a second protein. Such fusion proteins can be further utilized in screening assays for compounds that modulate Oncoseq protein activity (such assays are described in detail below).

In another embodiment, the fusion protein is a GST-Oncoseq protein fusion protein in which the Oncoseq protein sequences are fused to the C-terminus of the GST (i.e., glutathione S-transferase) sequences. Such fusion proteins can facilitate the purification of recombinant Oncoseq protein.

In yet another embodiment the fusion protein is an Oncoseq protein containing a heterologous signal sequence at its N-terminus. For example, the native Oncoseq protein signal sequence can be removed and replaced with a signal sequence from another protein. In certain host cells (e.g., mammalian host cells), expression and/or secretion of the Oncoseq protein can be increased through use of a heterologous signal sequence.

In another embodiment, the fusion protein is an Oncoseq protein-immunoglobulin fusion protein in which the Oncoseq protein sequences comprising one or more domains are fused to sequences derived from a member of the immunoglobulin protein family. The Oncoseq protein-immunoglobulin fusion proteins of the invention can be incorporated into pharmaceutical compositions and administered to a subject to inhibit an interaction between an Oncoseq protein ligand and an Oncoseq protein on the surface of a cell, to thereby suppress Oncoseq protein-mediated signal transduction in vivo. In one nonlimiting example, a contemplated Oncoseq protein ligand of the invention is an Oncoseq protein receptor. The Oncoseq protein-immunoglobulin fusion proteins can be used to modulate the bioavailability of an Oncoseq protein cognate ligand. Inhibition of the Oncoseq protein ligand-Oncoseq protein interaction may be useful therapeutically for both the treatment of proliferative and differentiative disorders, as well as modulating (e.g., promoting or inhibiting) cell survival. Moreover, the Oncoseq protein-immunoglobulin fusion proteins of the invention can be used as immunogens to produce anti-Oncoseq protein antibodies in a subject, to purify Oncoseq protein ligands, and in screening assays to identify molecules that inhibit the interaction of an Oncoseq protein with an Oncoseq protein ligand.

An Oncoseq protein chimeric or fusion protein of the invention can be produced by standard recombinant DNA techniques. For example, DNA fragments coding for the different polypeptide sequences are ligated together in-frame in accordance with conventional techniques, e.g., by employing blunt-ended or stagger-ended termini for ligation, restriction enzyme digestion to provide for appropriate termini, filling-in of cohesive ends as appropriate., alkaline phosphatase treatment to avoid undesirable joining, and enzymatic ligation. In another embodiment, the fusion gene can be synthesized by conventional techniques including automated DNA synthesizers. Alternatively, PCR amplification of gene fragments can be carried out using anchor primers that give rise to complementary overhangs between two consecutive gene fragments that can subsequently be annealed and reamplified to generate a chimeric gene sequence (see, for example, Ausubel et al. (eds.) CURRENT PROTOCOLS IN MOLECULAR BIOLOGY, John Wiley & Sons, 1992). Moreover, many expression vectors are commercially available that already encode a fusion moiety (e.g., a GST polypeptide). An Oncoseq protein-encoding nucleic acid can be cloned into such an expression vector such that the fusion moiety is linked in-frame to the Oncoseq protein.

Oncoseq Agonists and Antagonists

The present invention also pertains to variants of the Oncoseq proteins that function as either Oncoseq protein agonists (mimetics) or as Oncoseq protein antagonists. Variants of the Oncoseq protein can be generated by mutagenesis, e.g., discrete point mutation or truncation of the Oncoseq protein. An agonist of the Oncoseq protein can retain substantially the same, or a subset of, the biological activities of the naturally occurring form of the Oncoseq protein. An antagonist of the Oncoseq protein can inhibit one or more of the activities of the naturally occurring form of the Oncoseq protein by, for example, competitively binding to a downstream or upstream member of a cellular signaling cascade which includes the Oncoseq protein. Thus, specific biological effects can be elicited by treatment with a variant of limited function. In one embodiment, treatment of a subject with a variant having a subset of the biological activities of the naturally occurring form of the protein has fewer side effects in a subject relative to treatment with the naturally occurring form of the Oncoseq proteins.

Variants of the Oncoseq protein that function as either agonists (mimetics) or as antagonists can be identified by screening combinatorial libraries of mutants, e.g., truncation mutants, of the Oncoseq protein for Oncoseq protein agonist or antagonist activity. In one embodiment, a variegated library of Oncoseq variants is generated by combinatorial mutagenesis at the nucleic acid level and is encoded by a variegated gene library. A variegated library of Oncoseq variants can be produced by, for example, enzymatically ligating a mixture of synthetic oligonucleotides into gene sequences such that a degenerate set of potential Oncoseq sequences is expressible as individual polypeptides, or alternatively, as a set of larger fusion proteins (e.g., for phage display) containing the set of Oncoseq sequences therein. There are a variety of methods which can be used to produce libraries of potential Oncoseq variants from a degenerate oligonucleotide sequence. Chemical synthesis of a degenerate gene sequence can be performed in an automatic DNA synthesizer, and the synthetic gene then ligated into an appropriate expression vector. Use of a degenerate set of genes allows for the provision, in one mixture, of all of the sequences encoding the desired set of potential Oncoseq sequences. Methods for synthesizing degenerate oligonucleotides are known in the art (see, e.g., Narang (1983) *Tetrahedron* 39:3; Itakura et al (1984) *Annu Rev Biochem* 53:323; Itakura et al. (1984) *Science* 198:1056; Ike et al. (1983) *Nucl Acid Res* 11:477.

Polypeptide Libraries

In addition, libraries of fragments of the Oncoseq protein coding sequence can be used to generate a variegated population of functional fragments for screening and subsequent selection of variants of an Oncoseq protein. In one embodiment, a library of coding sequence fragments can be generated by treating a double stranded PCR fragment of an Oncoseq coding sequence with a nuclease under conditions wherein nicking occurs only about once per molecule, denaturing the double stranded DNA, renaturing the DNA to form double stranded DNA that can include sense/antisense pairs from different nicked products, removing single stranded portions from reformed duplexes by treatment with S1 nuclease, and ligating the resulting fragment library into an expression vector. By this method, an expression library can be derived which encodes N-terminal and internal fragments of various sizes of the Oncoseq protein.

Several techniques are known in the art for screening gene products of combinatorial libraries made by point mutations or truncation, and for screening cDNA libraries for gene products having a selected property. Such techniques are adaptable for rapid screening of the gene libraries generated by the combinatorial mutagenesis of Oncoseq proteins. The most widely used techniques, which are amenable to high throughput analysis, for screening large gene libraries typically include cloning the gene library into replicable expression vectors, transforming appropriate cells with the resulting library of vectors, and expressing the combinatorial genes under conditions in which detection of a desired activity facilitates isolation of the vector encoding the gene whose product was detected. Recrusive ensemble mutagenesis (REM), a new technique that enhances the frequency of functional mutants in the libraries, can be used in combination with the screening assays to identify Oncoseq variants (Arkin and Yourvan (1992) Proc. Natl. Acad. Sci. USA 89:7811-7815; Delgrave et al. (1993) Protein Engineering 6:327-331).

Anti-Oncoseq Antibodies

The term "antibody" as used herein refers to immunoglobulin molecules and immunologically active portions of immunoglobulin (Ig) molecules, i.e., molecules that contain an antigen binding site that specifically binds (immunoreacts with) an antigen. Such antibodies include, but are not limited to, polyclonal, monoclonal, chimeric, single chain, $F_{ab}$, $F_{ab'}$ and $F_{(ab')2}$ fragments, and an $F_{ab}$ expression library. In general, antibody molecules obtained from humans relates to any of the classes IgG, IgM, IgA, IgE and IgD, which differ from one another by the nature of the heavy chain present in the molecule. Certain classes have subclasses as well, such as $IgG_1$, $IgG_2$, and others. Furthermore, in humans, the light chain may be a kappa chain or a lambda chain. Reference herein to antibodies includes a reference to all such classes, subclasses and types of human antibody species. Any antibody disclosed herein binds "immunospecifically" to its cognate antigen. By immunospecific binding is meant that an antibody raised by challenging a host with a particular immunogen binds to a molecule such as an antigen that includes the immunogenic moiety with a high affinity, and binds with only a weak affinity or not at all to non-immunogen-containing molecules. As used in this definition, high affinity means having a dissociation constant less than about $1 \times 10^{-6}$ M, and weak affinity means having a dissociation constant higher than about $1 \times 10^{-6}$ M.

An isolated protein of the invention intended to serve as an antigen, or a portion or fragment thereof, can be used as an immunogen to generate antibodies that immunospecifically bind the antigen, using standard techniques for polyclonal and monoclonal antibody preparation. The full-length protein can be used or, alternatively, the invention provides antigenic peptide fragments of the antigen for use as immunogens. An antigenic peptide fragment comprises at least 6 amino acid residues of the amino acid sequence of the full length protein, such as an amino acid sequence shown in SEQ ID NOs:2 and 4, and encompasses an epitope thereof such that an antibody raised against the peptide forms a specific immune complex with the full length protein or with any fragment that contains the epitope. Preferably, the antigenic peptide comprises at least 10 amino acid residues, or at least 15 amino acid residues, or at least 20 amino acid residues, or at least 30 amino acid residues. Preferred epitopes encompassed by the antigenic peptide are regions of the protein that are located on its surface; commonly these are hydrophilic regions.

In certain embodiments of the invention, at least one epitope encompassed by the antigenic peptide is a region of the Oncoseq protein that is located on the surface of the protein, e.g., a hydrophilic region. A hydrophobicity analysis of the human Oncoseq protein sequence will indicate which regions of an Oncoseq polypeptide are particularly hydrophilic and, therefore, are likely to encode surface residues useful for targeting antibody production. As a means for targeting antibody production, hydropathy plots showing regions of hydrophilicity and hydrophobicity may be generated by any method well known in the art, including, for example, the Kyte Doolittle or the Hopp Woods methods, either with or without Fourier transformation. See, e g, Hopp and Woods, 1981, *Proc. Nat. Acad. Sci. USA* 78: 3824-3828; Kyte and Doolittle 1982, *J. Mol. Biol.* 157: 105-142, each incorporated herein by reference in their entirety. Antibodies that are specific for one or more domains within an antigenic protein, or derivatives, fragments, analogs or homologs thereof, are also provided herein.

A protein of the invention, or a derivative, fragment, analog, homolog or ortholog thereof, may be utilized as an immunogen in the generation of antibodies that immunospecifically bind these protein components.

Various procedures known within the art may be used for the production of polyclonal or monoclonal antibodies directed against a protein of the invention, or against derivatives, fragments, analogs homologs or orthologs thereof (see, for example, Antibodies: A Laboratory Manual, Harlow E, and Lane D, 1988; Cold Spring Harbor Laboratory Press, Cold Spring Harbor, N.Y., incorporated herein by reference). Some of these antibodies are discussed below.

1. Polyclonal Antibodies

For the production of polyclonal antibodies, various suitable host animals (e.g., rabbit, goat, mouse or other mammal) may be immunized by one or more injections with the native protein, a synthetic variant thereof, or a derivative of the foregoing. An appropriate immunogenic preparation can contain, for example, the naturally occurring immunogenic protein, a chemically synthesized polypeptide representing the immunogenic protein, or a recombinantly expressed immunogenic protein. Furthermore, the protein may be conjugated to a second protein known to be immunogenic in the mammal being immunized. Examples of such immunogenic proteins include but are not limited to keyhole limpet hemocyanin, serum albumin, bovine thyroglobulin, and soybean trypsin inhibitor. The preparation can further include an adjuvant. Various adjuvants used to increase the immunological response include, but are not limited to, Freund's (complete and incomplete), mineral gels (e.g., aluminum hydroxide), surface active substances (e.g., lysolecithin, pluronic polyols, polyanions, peptides, oil emulsions, dinitrophenol, etc.), adjuvants usable in humans such as Bacille Calmette-Guerin and *Corynebacterium parvum*, or similar immunostimulatory agents. Additional examples of adjuvants which can be employed include MPL-TDM adjuvant (monophosphoryl Lipid A, synthetic trehalose dicorynomycolate).

The polyclonal antibody molecules directed against the immunogenic protein can be isolated from the mammal (e.g., from the blood) and further purified by well known techniques, such as affinity chromatography using protein A or protein G, which provide primarily the IgG fraction of immune serum. Subsequently, or alternatively, the specific antigen which is the target of the immunoglobulin sought, or an epitope thereof, may be immobilized on a column to purify the immune specific antibody by immunoaffinity chromatography. Purification of immunoglobulins is dis-

2. Monoclonal Antibodies

The term "monoclonal antibody" (MAb) or "monoclonal antibody composition", as used herein, refers to a population of antibody molecules that contain only one molecular species of antibody molecule consisting of a unique light chain gene product and a unique heavy chain gene product. In particular, the complementarity determining regions (CDRs) of the monoclonal antibody are identical in all the molecules of the population. MAbs thus contain an antigen binding site capable of immunoreacting with a particular epitope of the antigen characterized by a unique binding affinity for it.

Monoclonal antibodies can be prepared using hybridoma methods, such as those described by Kohler and Milstein, *Nature*, 256:495 (1975). In a hybridoma method, a mouse, hamster, or other appropriate host animal, is typically immunized with an immunizing agent to elicit lymphocytes that produce or are capable of producing antibodies that will specifically bind to the immunizing agent. Alternatively, the lymphocytes can be immunized in vitro.

The immunizing agent will typically include the protein antigen, a fragment thereof or a fusion protein thereof. Generally, either peripheral blood lymphocytes are used if cells of human origin are desired, or spleen cells or lymph node cells are used if non-human mammalian sources are desired. The lymphocytes are then fused with an immortalized cell line using a suitable fusing agent, such as polyethylene glycol, to form a hybridoma cell [Goding, *Monoclonal Antibodies: Principles and Practice*, Academic Press, (1986) pp. 59-103]. Immortalized cell lines are usually transformed mammalian cells, particularly myeloma cells of rodent, bovine and human origin. Usually, rat or mouse myeloma cell lines are employed. The hybridoma cells can be cultured in a suitable culture medium that preferably contains one or more substances that inhibit the growth or survival of the unfused, immortalized cells. For example, if the parental cells lack the enzyme hypoxanthine guanine phosphoribosyl transferase (HGPRT or HPRT), the culture medium for the hybridomas typically will include hypoxanthine, aminopterin, and thymidine ("HAT medium"), which substances prevent the growth of HGPRT-deficient cells.

Preferred immortalized cell lines are those that fuse efficiently, support stable high level expression of antibody by the selected antibody-producing cells, and are sensitive to a medium such as HAT medium. More preferred immortalized cell lines are murine myeloma lines, which can be obtained, for instance, from the Salk Institute Cell Distribution Center, San Diego, Calif. and the American Type Culture Collection, Manassas, Va. Human myeloma and mouse-human heteromyeloma cell lines also have been described for the production of human monoclonal antibodies (Kozbor: *J. Immunol.* 133:3001 (1984); Brodeur et al.: *Monoclonal Antibody Production Techniques and Applications*, Marcel Dekker, Inc., New York, (1987) pp. 51-63).

The culture medium in which the hybridoma cells are cultured can then be assayed for the presence of monoclonal antibodies directed against the antigen. Preferably, the binding specificity of monoclonal antibodies produced by the hybridoma cells is determined by immunoprecipitation or by an in vitro binding assay, such as radioimmunoassay (RIA) or enzyme-linked immunoabsorbent assay (ELISA). Such techniques and assays are known in the art. The binding affinity of the monoclonal antibody can, for example, be determined by the Scatchard analysis of Munson and Pollard, *Anal. Biochem.*, 107:220 (1980). It is an objective, especially important in therapeutic applications of monoclonal antibodies, to identify antibodies having a high degree of specificity and a high binding affinity for the target antigen.

After the desired hybridoma cells are identified, the clones can be subcloned by limiting dilution procedures and grown by standard methods (Goding, 1986). Suitable culture media for this purpose include, for example, Dulbecco's Modified Eagle's Medium and RPMI-1640 medium. Alternatively, the hybridoma cells can be grown in vivo as ascites in a mammal.

The monoclonal antibodies secreted by the subclones can be isolated or purified from the culture medium or ascites fluid by conventional immunoglobulin purification procedures such as, for example, protein A-Sepharose, hydroxylapatite chromatography, gel electrophoresis, dialysis, or affinity chromatography.

The monoclonal antibodies can also be made by recombinant DNA methods, such as those described in U.S. Pat. No. 4,816,567. DNA encoding the monoclonal antibodies of the invention can be readily isolated and sequenced using conventional procedures (e.g., by using oligonucleotide probes that are capable of binding specifically to genes encoding the heavy and light chains of murine antibodies). The hybridoma cells of the invention serve as a preferred source of such DNA. Once isolated, the DNA can be placed into expression vectors, which are then transfected into host cells such as simian COS cells, Chinese hamster ovary (CHO) cells, or myeloma cells that do not otherwise produce immunoglobulin protein, to obtain the synthesis of monoclonal antibodies in the recombinant host cells. The DNA also can be modified, for example, by substituting the coding sequence for human heavy and light chain constant domains in place of the homologous murine sequences (U.S. Pat. No. 4,816,567; Morrison (1994) Nature 368, 812-13) or by covalently joining to the immunoglobulin coding sequence all or part of the coding sequence for a non-immunoglobulin polypeptide. Such a non-immunoglobulin polypeptide can be substituted for the constant domains of an antibody of the invention, or can be substituted for the variable domains of one antigen-combining site of an antibody of the invention to create a chimeric bivalent antibody.

3. Humanized Antibodies

The antibodies directed against the protein antigens of the invention can further comprise humanized antibodies or human antibodies. These antibodies are suitable for administration to humans without engendering an immune response by the human against the administered immunoglobulin.

Humanized forms of antibodies are chimeric immunoglobulins, immunoglobulin chains or fragments thereof (such as Fv, Fab, Fab', F(ab')$_2$ or other antigen-binding subsequences of antibodies) that are principally comprised of the sequence of a human immunoglobulin, and contain minimal sequence derived from a non-human immunoglobulin. Humanization can be performed following the method of Winter and co-workers (Jones et al, *Nature* 321:522-525 (1986); Riechmann et al., *Nature*, 332:323-327 (1988); Verhoeyen et al., *Science*, 239:1534-1536 (1988)), by substituting rodent CDRs or CDR sequences for the corresponding sequences of a human antibody. (See also U.S. Pat. No. 5,225,539.) In some instances, Fv framework residues of the human immunoglobulin are replaced by corresponding non-human residues. Humanized antibodies can also comprise residues which are found neither in the recipient antibody nor in the imported CDR or framework sequences. In general the humanized antibody will comprise substantially all of at least one, and typically two, variable domains, in which all or substantially all of the CDR regions correspond to those of a non-human immunoglobulin and all or substantially all of the framework regions are those of a human immunoglobulin consensus sequence. The humanized antibody optimally also will comprise at least a portion of an immunoglobulin constant region (Fe), typically that of a human immunoglobulin (Jones et al., 1986; Riechmann et al., 1988; and Presta (1992) Curr. Op. Struct. Biol., 2:593-596).

4. Human Antibodies

Fully human antibodies essentially relate to antibody molecules in which the entire sequence of both the light chain and the heavy chain, including the CDRs, arise from human genes. Such antibodies are termed "human antibodies", or "fully human antibodies" herein. Human monoclonal antibodies can be prepared by the trioma technique; the human B-cell hybridoma technique (see Kozbor, et al. (1983) Immunol Today 4: 72) and the EBV hybridoma technique to produce human monoclonal antibodies (see Cole, et al. (1985) In: MONOCLONAL ANTIBODIES AND CANCER THERAPY, Alan R. Liss, Inc., pp. 77-96). Human monoclonal antibodies may be utilized in the practice of the present invention and may be produced by using human hybridomas (see Cote, et al. (1983) Proc Natl Acad Sci USA 80: 2026-2030) or by transforming human B-cells with Epstein Barr Virus in vitro (see Cole, et al. (1985) in: MONOCLONAL ANTIBODIES AND CANCER THERAPY, Alan R. Liss, Inc., pp. 77-96).

In addition, human antibodies can also be produced using additional techniques, including phage display libraries (Hoogenboom and Winter (1991) J. Mol. Biol., 227:381; Marks et al. (1991) J. Mol. Biol., 222:581). Similarly, human antibodies can be made by introducing human immunoglobulin loci into transgenic animals e.g., mice in which the endogenous immunoglobulin genes have been partially or completely inactivated. Upon challenge, human antibody production is observed, which closely resembles that seen in humans in all respects, including gene rearrangement, assembly, and antibody repertoire. This approach is described, for example, in U.S. Pat. Nos. 5,545,807; 5,545, 806; 5,569,825; 5,625,126; 5,633,425; 5,661,016, and in Marks et al. (1992) (Bio/Technology 10, 779-783); Lonberg et al. ((1994) Nature 368 856-859); Morrison ((1994) Nature 368, 812-13); Fishwild et al, ((1996) Nature Biotechnology 14, 845-51); Neuberger ((1996) Nature Biotechnology 14, 826); and Lonberg and Huszar ((1995) Intern. Rev. Immunol. 13 65-93).

Human antibodies may additionally be produced using transgenic nonhuman animals which are modified so as to produce fully human antibodies rather than the animal's endogenous antibodies in response to challenge by an antigen. (See publication WO 94/02602). The endogenous genes encoding the heavy and light immunoglobulin chains in the nonhuman host have been incapacitated, and active loci encoding human heavy and light chain immunoglobulins are inserted into the host's genome. The human genes are incorporated, for example, using yeast artificial chromosomes containing the requisite human DNA segments. An animal which provides all the desired modifications is then obtained as progeny by crossbreeding intermediate transgenic animals containing fewer than the full complement of the modifications. The preferred embodiment of such a nonhuman animal is a mouse, and is termed the Xenomouse™ as disclosed in PCT publications WO 96/33735 and WO 96/34096. This animal produces B cells which secrete fully human immunoglobulins. The antibodies can be obtained directly from the animal after immunization with an immunogen of interest, as, for example, a preparation of a polyclonal antibody, or alternatively from immortalized B cells derived from the animal, such as hybridomas producing monoclonal antibodies. Additionally, the genes encoding the immunoglobulins with human variable regions can be recovered and expressed to obtain the antibodies directly, or can be further modified to obtain analogs of antibodies such as, for example, single chain Fv molecules.

An example of a method of producing a nonhuman host, exemplified as a mouse, lacking expression of an endogenous immunoglobulin heavy chain is disclosed in U.S. Pat. No. 5,939,598. It can be obtained by a method including deleting the J segment genes from at least one endogenous heavy chain locus in an embryonic stem cell to prevent rearrangement of the locus and to prevent formation of a transcript of a rearranged immunoglobulin heavy chain locus, the deletion being effected by a targeting vector containing a gene encoding a selectable marker; and producing from the embryonic stem cell a transgenic mouse whose somatic and germ cells contain the gene encoding the selectable marker.

A method for producing an antibody of interest, such as a human antibody, is disclosed in U.S. Pat. No. 5,916,771. It includes introducing an expression vector that contains a nucleotide sequence encoding a heavy chain into one mammalian host cell in culture, introducing an expression vector containing a nucleotide sequence encoding a light chain into another mammalian host cell, and fusing the two cells to form a hybrid cell. The hybrid cell expresses an antibody containing the heavy chain and the light chain.

In a further improvement on this procedure, a method for identifying a clinically relevant epitope on an immunogen, and a correlative method for selecting an antibody that binds immunospecifically to the relevant epitope with high affinity, are disclosed in PCT publication WO 99/53049.

5. $F_{ab}$ Fragments and Single Chain Antibodies

According to the invention, techniques can be adapted for the production of single-chain antibodies specific to an antigenic protein of the invention (see e.g., U.S. Pat. No. 4,946,778). In addition, methods can be adapted for the construction of $F_{ab}$ expression libraries (see e.g., Huse, et al., 1989 Science 246: 1275-1281) to allow rapid and effective identification of monoclonal $F_{ab}$ fragments with the desired specificity for a protein or derivatives, fragments, analogs or homologs thereof. Antibody fragments that contain the idiotypes to a protein antigen may be produced by techniques known in the art including, but not limited to: (i) an $F_{(ab')2}$ fragment produced by pepsin digestion of an antibody molecule; (ii) an $F_{ab}$ fragment generated by reducing the disulfide bridges of an $F_{(ab')2}$ fragment; (iii) an $F_{ab}$ fragment generated by the treatment of the antibody molecule with papain and a reducing agent and (iv) $F_v$ fragments.

6. Bispecific Antibodies

Bispecific antibodies are monoclonal, preferably human or humanized, antibodies that have binding specificities for at least two different antigens. In the present case, one of the binding specificities is for an antigenic protein of the invention. The second binding target is any other antigen, and advantageously is a cell-surface protein or receptor or receptor subunit.

Methods for making bispecific antibodies are known in the art. Traditionally, the recombinant production of bispecific antibodies is based on the co-expression of two immunoglobulin heavy-chain/light-chain pairs, where the two heavy chains have different specificities (Milstein and Cuello, *Nature,* 305:537-539 (1983)). Because of the random assortment of immunoglobulin heavy and light chains, these hybridomas (quadromas) produce a potential mixture of ten different antibody molecules, of which only one has the correct bispecific structure The purification of the correct molecule is usually accomplished by affinity chromatography steps. Similar procedures are disclosed in WO 93/08829, published 13 May 1993, and in Traunecker et al. (1991) EMBO J., 10:3655-3659.

Antibody variable domains with the desired binding specificities (antibody-antigen combining sites) can be fused to immunoglobulin constant domain sequences. The fusion preferably is with an immunoglobulin heavy-chain constant domain, comprising at least part of the hinge, CH2, and CH3 regions. It is preferred to have the first heavy-chain constant region (CH1) containing the site necessary for light-chain binding present in at least one of the fusions. DNAs encoding the immunoglobulin heavy-chain fusions and, if desired, the immunoglobulin light chain, are inserted into separate expression vectors, and are co-transfected into a suitable host organism. For further details of generating bispecific antibodies see, for example, Suresh et al. (1986) Methods in Enzymology, 121:210.

According to another approach described in WO 96/27011, the interface between a pair of antibody molecules can be engineered to maximize the percentage of heterodimers which are recovered from recombinant cell culture. The preferred interface comprises at least a part of the CH3 region of an antibody constant domain. In this method, one or more small amino acid side chains from the interface of the first antibody molecule are replaced with larger side chains (e.g. tyrosine or tryptophan). Compensatory "cavities" of identical or similar size to the large side chain(s) are created on the interface of the second antibody molecule by replacing large amino acid side chains with smaller ones (e.g. alanine or threonine). This provides a mechanism for increasing the yield of the heterodimer over other unwanted end-products such as homodimers.

Bispecific antibodies can be prepared as full length antibodies or antibody fragments (e.g. F(ab')$_2$ bispecific antibodies). Techniques for generating bispecific antibodies from antibody fragments have been described in the literature. For example, bispecific antibodies can be prepared using chemical linkage. Brennan et al., *Science* 229:81 (1985) describe a procedure wherein intact antibodies are proteolytically cleaved to generate F(ab')$_2$ fragments. These fragments are reduced in the presence of the dithiol complexing agent sodium arsenite to stabilize vicinal dithiols and prevent intermolecular disulfide formation. The Fab' fragments generated are then converted to thionitrobenzoate (TNB) derivatives. One of the Fab'-TNB derivatives is then reconverted to the Fab'-thiol by reduction with mercaptoethylamine and is mixed with an equimolar amount of the other Fab'-TNB derivative to form the bispecific antibody. The bispecific antibodies produced can be used as agents for the selective immobilization of enzymes.

Additionally, Fab' fragments can be directly recovered from *E. coli* and chemically coupled to form bispecific antibodies. Shalaby et al. (1992) J. Exp. Med. 175:217-225 describe the production of a fully humanized bispecific antibody F(ab')$_2$ molecule. Each Fab' fragment was separately secreted from *E coli* and subjected to directed chemical coupling in vitro to form the bispecific antibody. The bispecific antibody thus formed was able to bind to cells overexpressing the ErbB2 receptor and normal human T cells, as well as trigger the lytic activity of human cytotoxic lymphocytes against human breast tumor targets.

Various techniques for making and isolating bispecific antibody fragments directly from recombinant cell culture have also been described. For example, bispecific antibodies have been produced using leucine zippers. Kostelny et al. (1992) J. Immunol. 148(5):1547-1553. The leucine zipper peptides from the Fos and Jun proteins were linked to the Fab' portions of two different antibodies by gene fusion. The antibody homodimers were reduced at the hinge region to form monomers and then re-oxidized to form the antibody heterodimers. This method can also be utilized for the production of antibody homodimers. The "diabody" technology described by Hollinger et al., (1993) Proc. Natl. Acad. Sci. USA 90:6444-6448 has provided an alternative mechanism for making bispecific antibody fragments. The fragments comprise a heavy-chain variable domain ($V_H$) connected to a light-chain variable domain ($V_L$) by a linker which is too short to allow pairing between the two domains on the same chain. Accordingly, the $V_H$ and $V_L$ domains of one fragment are forced to pair with the complementary $V_L$ and $V_H$ domains of another fragment, thereby forming two antigen-binding sites. Another strategy for making bispecific antibody fragments by the use of single-chain Fv (sFv) dimers has also been reported. See, Gruber et al. (1994) J. Immunol. 152:5368.

Antibodies with more than two valencies are contemplated. For example, trispecific antibodies can be prepared. Tutt et al. (1991) J. Immunol. 147:60.

Exemplary bispecific antibodies can bind to two different epitopes, at least one of which originates in the protein antigen of the invention. Alternatively, an anti-antigenic arm of an immunoglobulin molecule can be combined with an arm which binds to a triggering molecule on a leukocyte such as a T-cell receptor molecule (e.g. CD2, CD3, CD28, or B7), or Fc receptors for IgG (FcγR), such as FcγRI (CD64), FcγRII (CD32) and FcγRIII (CD16) so as to focus cellular defense mechanisms to the cell expressing the particular antigen. Bispecific antibodies can also be used to direct cytotoxic agents to cells which express a particular antigen. These antibodies possess an antigen-binding arm and an arm which binds a cytotoxic agent or a radionuclide chelator, such as EOTUBE, DPTA, DOTA, or TETA Another bispecific antibody of interest binds the protein antigen described herein and further binds tissue factor (TF).

7. Heteroconjugate Antibodies

Heteroconjugate antibodies are also within the scope of the present invention. Heteroconjugate antibodies are composed of two covalently joined antibodies. Such antibodies have, for example, been proposed to target immune system cells to unwanted cells (U.S. Pat. No. 4,676,980), and for treatment of HIV infection (WO 91/00360; WO 92/200373; EP 03089). It is contemplated that the antibodies can be prepared in vitro using known methods in synthetic protein chemistry, including those involving crosslinking agents. For example, immunotoxins can be constructed using a disulfide exchange reaction or by forming a thioether bond. Examples of suitable reagents for this purpose include iminothiolate and methyl-4-mercaptobutyrimidate and those disclosed, for example, in U.S. Pat. No. 4,676,980.

8. Effector Function Engineering

It can be desirable to modify the antibody of the invention with respect to effector function, so as to enhance, e.g., the effectiveness of the antibody in treating cancer. For example, cysteine residue(s) can be introduced into the Fc region, thereby allowing interchain disulfide bond formation in this region. The homodimeric antibody thus generated can have improved internalization capability and/or increased complement-mediated cell killing and antibody-dependent cellular cytotoxicity (ADCC). See Caron et al., *J. Exp Med.* (1992) 176:1191-1195 and Shopes (1992) *J. Immunol.*, 148: 2918-2922. Homodimeric antibodies with enhanced antitumor activity can also be prepared using heterobifunctional cross-linkers as described in Wolff et al. (1993) *Cancer Research*, 53: 2560-2565. Alternatively, an antibody can be engineered that has dual Fc regions and can thereby have enhanced complement lysis and ADCC capabilities. See Stevenson et al. (1989) *Anti-Cancer Drug Design*, 3: 219-230.

9. Immunoconjugates

The invention also pertains to immunoconjugates comprising an antibody conjugated to a cytotoxic agent such as a chemotherapeutic agent, toxin (e.g., an enzymatically active toxin of bacterial, fungal, plant, or animal origin, or fragments thereof), or a radioactive isotope (i.e., a radioconjugate).

Chemotherapeutic agents useful in the generation of such immunoconjugates have been described above. Enzymatically active toxins and fragments thereof that can be used include diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca americana* proteins (PAPI, PAPII, and PAP-S), momordica charantia inhibitor, curcin, crotin, sapaonaria officinalis inhibitor, gelonin, mitogeltin, restrictocin, phenomycin, enomycin, and the tricothecenes. A variety of radionuclides are available for the production of radioconjugated antibodies. Examples include $^{212}Bi$, $^{131}I$, $^{131}In$, $^{90}Y$, and $^{186}Re$.

Conjugates of the antibody and cytotoxic agent are made using a variety of bifunctional protein-coupling agents such as N-succinimidyl-3-(2-pyridyidithiol) propionate (SPDP), iminothiotane (IT), bifunctional derivatives of imidoesters (such as dimethyl adipimidate HCL), active esters (such as disuccinimidyl suberate), aldehydes (such as glutaraldehyde), bis-azido compounds (such as bis (p-azidobenzoyl) hexanediamine), bis-diazonium derivatives (such as bis-p-diazoniumbenzoyl)-ethylenediamine), diisocyanates (such as tolyene 2,6-diisocyanate), and bis-active fluorine compounds (such as 1,5-difluoro-2,4-dinitrobenzene). For example, a ricin immunotoxin can be prepared as described in Vitetta et al., *Science*, 238: 1098 (1987). Carbon-14-labeled 1-isothiocyanatobenzyl-3-methyldiethylene triaminepentaacetic acid (MX-DTPA) is an exemplary chelating agent for conjugation of radionucleotide to the antibody. See WO94/11026.

In another embodiment, the antibody can be conjugated to a "receptor" (such streptavidin) for utilization in tumor pretargeting wherein the antibody-receptor conjugate is administered to the patient, followed by removal of unbound conjugate from the circulation using a clearing agent and then administration of a "ligand" (e.g., avidin) that is in turn conjugated to a cytotoxic agent.

10. Immunoliposomes

The antibodies disclosed herein can also be formulated as immunoliposomes. Liposomes containing the antibody are prepared by methods known in the art, such as described in Epstein et al., *Proc. Natl Acad. Sci. USA*, 82: 3688 (1985); Hwang et al., *Proc. Natl Acad. Sci USA*, 77: 4030 (1980); and U.S. Pat. Nos. 4,485,045 and 4,544,545. Liposomes with enhanced circulation time are disclosed in U.S. Pat. No. 5,013,556.

Particularly useful liposomes can be generated by the reverse-phase evaporation method with a lipid composition comprising phosphatidylcholine, cholesterol, and PEG-derivatized phosphatidylethanolamine (PEG-PE). Liposomes are extruded through filters of defined pore size to yield liposomes with the desired diameter. Fab' fragments of the antibody of the present invention can be conjugated to the liposomes as described in Martin et al., *J. Biol. Chem.*, 257: 286-288 (1982) via a disulfide interchange reaction. A chemotherapeutic agent (such as Doxorubicin) is optionally contained within the liposome. See Gabizon et al., *J. National Cancer Inst.*, 81(19): 1484 (1989).

11. Diagnostic Applications of Antibodies Directed Against the Proteins of the Invention Antibodies directed against a protein of the invention may be used in methods known within the art relating to the localization and/or quantitation of the protein (e.g., for use in measuring levels of the protein within appropriate physiological samples, for use in diagnostic methods, for use in imaging the protein, and the like). In a given embodiment, antibodies against the proteins, or derivatives, fragments, analogs or homologs thereof, that contain the antigen binding domain, are utilized as pharmacologically-active compounds (see below).

An antibody specific for a protein of the invention can be used to isolate the protein by standard techniques, such as immunoaffinity chromatography or immunoprecipitation. Such an antibody can facilitate the purification of the natural protein antigen from cells and of recombinantly produced antigen expressed in host cells. Moreover, such an antibody can be used to detect the antigenic protein (e.g., in a cellular lysate or cell supernatant) in order to evaluate the abundance and pattern of expression of the antigenic protein. Antibodies directed against the protein can be used diagnostically to monitor protein levels in tissue as part of a clinical testing procedure, e.g., to, for example, determine the efficacy of a given treatment regimen. Detection can be facilitated by coupling (i.e., physically linking) the antibody to a detectable substance. Examples of detectable substances include various enzymes, prosthetic groups, fluorescent materials, luminescent materials, bioluminescent materials, and radioactive materials. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin, and examples of suitable radioactive material include $^{125}I$, $^{131}I$, $^{35}S$ or $^{3}H$.

12. Pharmaceutical Compositions of Antibodies

Antibodies specifically binding a protein of the invention, as well as other molecules identified by the screening assays disclosed herein, can be administered for the treatment of various disorders in the form of pharmaceutical compositions. Principles and considerations involved in preparing such compositions, as well as guidance in the choice of components are provided, for example, in Remington: The Science And Practice Of Pharmacy 19th ed. (Alfonso R. Gennaro, et al., editors) Mack Pub. Co., Easton, Pa.: 1995; Drug Absorption Enhancement: Concepts, Possibilities, Limitations, And Trends, Harwood Academic Publishers, Langhorne, Pa., 1994; and Peptide And Protein Drug Delivery (Advances In Parenteral Sciences, Vol. 4), 1991, M. Dekker, New York.

If the antigenic protein is intracellular and whole antibodies are used as inhibitors, internalizing antibodies are preferred. However, liposomes can also be used to deliver the antibody, or an antibody fragment, into cells. Where antibody fragments are used, the smallest inhibitory fragment that specifically binds to the binding domain of the target protein is preferred. For example, based upon the variable-region sequences of an antibody, peptide molecules can be designed that retain the ability to bind the target protein sequence. Such peptides can be synthesized chemically and/or produced by recombinant DNA technology. See, e.g., Marasco et al. (1993) Proc. Natl. Acad. Sci. USA, 90: 7889-7893. The formulation herein can also contain more than one active compound as necessary for the particular indication being treated, preferably those with complementary activities that do not adversely affect each other. Alternatively, or in addition, the composition can comprise an agent that enhances its function, such as, for example, a cytotoxic agent, cytokine, chemotherapeutic agent, or growth-inhibitory agent. Such molecules are suitably present in combination in amounts that are effective for the purpose intended.

The active ingredients can also be entrapped in microcapsules prepared, for example, by coacervation techniques or by interfacial polymerization, for example, hydroxymethylcellulose or gelatin-microcapsules and poly-(methylmethacrylate) microcapsules, respectively, in colloidal drug delivery systems (for example, liposomes, albumin microspheres, microemulsions, nanoparticies, and nanocapsules) or in macroemulsions.

The formulations to be used for in vivo administration must be sterile. This is readily accomplished by filtration through sterile filtration membranes.

13. Antibody Therapeutics

Antibodies of the invention, including polyclonal, monoclonal, humanized and fully human antibodies, may used as therapeutic agents. Such agents will generally be employed to treat or prevent a disease or pathology in a subject. An antibody preparation, preferably one having high specificity and high affinity for its target antigen, is administered to the subject and will generally have an effect due to its binding with the target. Such an effect may be one of two kinds, depending on the specific nature of the interaction between the given antibody molecule and the target antigen in question. In the first instance, administration of the antibody may abrogate or inhibit the binding of the target with an endogenous ligand to which it naturally binds. In this case, the antibody binds to the target and masks a binding site of the naturally occurring ligand, wherein the ligand serves as an effector molecule. Thus the receptor mediates a signal transduction pathway for which ligand is responsible.

Alternatively, the effect may be one in which the antibody elicits a physiological result by virtue of binding to an effector binding site on the target molecule. In this case the target, a receptor having an endogenous ligand which may be absent or defective in the disease or pathology, binds the antibody as a surrogate effector ligand, initiating a receptor-based signal transduction event by the receptor.

A therapeutically effective amount of an antibody of the invention relates generally to the amount needed to achieve a therapeutic objective. As noted above, this may be a binding interaction between the antibody and its target antigen that, in certain cases, interferes with the functioning of the target, and in other cases, promotes a physiological response. The amount required to be administered will furthermore depend on the binding affinity of the antibody for its specific antigen, and will also depend on the rate at which an administered antibody is depleted from the free volume other subject to which it is administered. Common ranges for therapeutically effective dosing of an antibody or antibody fragment of the invention may be, by way of nonlimiting example, from about 0.1 mg/kg body weight to about 50 mg/kg body weight. Common dosing frequencies may range, for example, from twice daily to once a week.

Oncoseq Recombinant Vectors and Host Cells

Another aspect of the invention pertains to vectors, preferably expression vectors, containing a nucleic acid encoding Oncoseq protein, or derivatives, fragments, analogs or homologs thereof. As used herein, the term "vector" refers to a nucleic acid molecule capable of transporting another nucleic acid to which it has been linked. One type of vector is a "plasmid", which refers to a circular double stranded DNA loop into which additional DNA segments can be ligated. Another type of vector is a viral vector, wherein additional DNA segments can be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors are capable of directing the expression of genes to which they are operatively linked. Such vectors are referred to herein as "expression vectors". In general, expression vectors of utility in recombinant DNA techniques are often in the form of plasmids. In the present specification, "plasmid" and "vector" can be used interchangeably as the plasmid is the most commonly used form of vector. However, the invention is intended to include such other forms of expression vectors, such as viral vectors (e.g., replication defective retroviruses, adenoviruses and adeno-associated viruses), which serve-equivalent functions.

The recombinant expression vectors of the invention comprise a nucleic acid of the invention in a form suitable for expression of the nucleic acid in a host cell, which means that the recombinant expression vectors include one or more regulatory sequences, selected on the basis of the host cells to be used for expression, that is operatively linked to the nucleic acid sequence to be expressed. Within a recombinant expression vector, "operably linked" is intended to mean that the nucleotide sequence of interest is linked to the regulatory sequencers) in a manner that allows for expression of the nucleotide sequence (e.g., in an in vitro transcription/translation system or in a host cell when the vector is introduced into the host cell). The term "regulatory sequence" is intended to includes promoters, enhancers and other expression control elements (e.g., polyadenylation signals). Such regulatory sequences are described, for example, in Goeddel (1990) GENE EXPRESSION TECHNOLOGY: METHODS IN ENZYMOLOGY 185, Academic Press, San Diego, Calif. Regulatory sequences include those that direct constitutive expression of a nucleotide sequence in many types of host cell and those that direct expression of the nucleotide sequence only in certain host cells (e.g., tissue-specific regulatory sequences), It will be appreciated by those skilled in the art that the design of the expression vector can depend on such factors as the choice of the host cell to be transformed, the level of expression of protein desired, etc. The expression vectors of the invention can be introduced into host cells to thereby produce proteins or peptides, including fusion proteins or peptides, encoded by nucleic acids as described herein (e.g., Oncoseq proteins, mutant forms of the Oncoseq protein, fusion proteins, etc.).

The recombinant expression vectors of the invention can be designed for expression of the Oncoseq protein in prokaryotic or eukaryotic cells. For example, the Oncoseq protein can be expressed in bacterial cells such as *E. coli*, insect cells (using baculovirus expression vectors) yeast cells or mammalian cells. Suitable host cells are discussed further in Goeddel (1990). Alternatively, the recombinant expression vector can be transcribed and translated in vitro, for example using T7 promoter regulatory sequences and T7 polymerase.

Expression of proteins in prokaryotes is most often carried out in *E. coli* with vectors containing constitutive or inducible promoters directing the expression of either fusion or non-fusion proteins. Fusion vectors add a number of amino acids to a protein encoded therein, usually to the amino terminus of the recombinant protein. Such fusion vectors typically serve three purposes: (1) to increase expression of recombinant protein; (2) to increase the solubility of the recombinant protein; and (3) to aid in the purification of the recombinant protein by acting as a ligand in affinity purification. Often, in fusion expression vectors, a proteolytic cleavage site is introduced at the junction of the fusion moiety and the recombinant protein to enable separation of the recombinant protein from the fusion moiety subsequent to purification of the fusion protein. Such enzymes, and their cognate recognition sequences, include Factor Xa, thrombin and enterokinase. Typical fusion expression vectors include pGEX (Pharmacia Biotech Inc; Smith and Johnson (1988) *Gene* 67:3140), pMAL (New England Biolabs, Beverly, Mass.) and pRIT5 (Pharmacia, Piscataway, N.J.) that fuse glutathione S-transferase (GST), maltose E binding protein, or protein A, respectively, to the target recombinant protein.

Examples of suitable inducible non-fusion *E. coli* expression vectors include pTrc (Amrann et al., 1998) *Gene* 69:301-315) and pET 11d (Studier et al., (1990) Gene Expression Technology: Methods in Enzymology 115, Academic Press, San Diego, Calif. 60-89).

One strategy to maximize recombinant protein expression in *E. coli* is to express the protein in a host bacteria with an impaired capacity to proteolytically cleave the recombinant protein. See, Gottesman (1990) Gene Expression Technology: Methods in Enzymology 185, Academic Press, San Diego, Calif. 119-128. Another strategy is to alter the nucleic acid sequence of the nucleic acid to be inserted into an expression vector so that the individual codons for each amino acid are those preferentially utilized in *E. coli* (Wada et al., (1992) *Nucleic Acids Res.* 20:2111-2118). Such alteration of nucleic acid sequences of the invention can be carried out by standard DNA synthesis techniques.

In another embodiment, the Oncoseq expression vector is a yeast expression vector. Examples of vectors for expression in yeast *S. cerivisae* include pYepSec1 (Baldari, et al., (1987) *EMBO J* 6:229-234), pMFa Kurjan and Herskowitz, (1982) *Cell* 30:933-943), pJRY88 (Schultz et al., (1987) *Gene* 54:113-123), pYES2 (Invitrogen Corporation, San Diego, Calif.), and picZ (InVitrogen Corp, San Diego, Calif.).

Alternatively, the Oncoseq protein can be expressed in insect cells using baculovirus expression vectors. Baculovirus vectors available for expression of proteins in cultured insect cells (e.g., SF9 cells) include the pAc series (Smith et al. (1983) *Mol Cell Biol* 3:2156-2165) and the pVL series (Lucklow and Summers (1989) *Virology* 170:31-39).

In yet another embodiment, a nucleic acid of the invention is expressed in mammalian cells using a mammalian expression vector. Examples of mammalian expression vectors include pCDM8 (Seed (1987) *Nature* 329:840) and pMT2PC (Kaufman et al. (187) *EMBO J* 6: 187-195). When used in mammalian cells, the expression vector's control functions are often provided by viral regulatory elements. For example, commonly used promoters are derived from polyoma, Adenovirus 2, cytomegalovirus and Simian Virus 40. For other suitable expression systems for both prokaryotic and eukaryotic cells. See, e.g., Chapters 16 and 17 of Sambrook et al., Molecular Cloning: A Laboratory Manual. 2nd ed., Cold Spring Harbor Laboratory, Cold Spring Harbor Laboratory Press, Cold Spring Harbor, N.Y., 1989.

In another embodiment, the recombinant mammalian expression vector is capable of directing expression of the nucleic acid preferentially in a particular cell type (e.g., tissue-specific regulatory elements are used to express the nucleic acid). Tissue-specific regulatory elements are known in the art. Non-limiting examples of suitable tissue-specific promoters include the albumin promoter (liver-specific; Pinkert et al. (1987) *Genes Dev* 11268-277), lymphoid-specific promoters (Calame and Eaton (1988) *Adv Immunol* 43:235-275), in particular promoters of T cell receptors (Winoto and Baltimore (1989) *EMBO J* 8:729-733) and immunoglobulins (Banerji et al. (1983) *Cell* 33:729-740; Queen and Baltimore (1983) *Cell* 33:741-748), neuron-specific promoters (e.g., the neurofilament promoter; Byrne and Ruddle (1989) *Proc. Natl. Acad. Sci. USA* 86:5473-5477), pancreas-specific promoters (Edlund et al. (11985) *Science* 230:912-916), and mammary gland-specific promoters (e.g., milk whey promoter; U.S. Pat. No. 4,873,316 and European Application Publication No. 264,166). Developmentally-regulated promoters are also encompassed, e.g., the murine hox promoters (Kessel and Gruss (1990) *Science* 249:374-379) and the α-fetoprotein promoter (Campes and Tilghman (1989) *Genes Dev* 3:537-546).

The invention further provides a recombinant expression vector comprising a DNA molecule of the invention cloned into the expression vector in an antisense orientation. That is, the DNA molecule is operatively linked to a regulatory sequence in a manner that allows for expression (by transcription of the DNA molecule) of an RNA molecule that is antisense to a Oncoseq mRNA. Regulatory sequences operatively linked to a nucleic acid cloned in the antisense orientation can be chosen that direct the continuous expression of the antisense RNA molecule in a variety of cell types, for instance viral promoters and/or enhancers, or regulatory sequences can be chosen that direct constitutive, tissue specific or cell type specific expression of antisense RNA. The antisense expression vector can be in the form of a recombinant plasmid, phagemid or attenuated virus in which antisense nucleic acids are produced under the control of a high efficiency regulatory region, the activity of which can be determined by the cell type into which the vector is introduced. For a discussion of the regulation of gene expression using antisense genes see Weintraub et al., "Antisense RNA as a molecular tool for genetic analysis," Reviews—Trends in Genetics, Vol. 1(1) 1986.

Another aspect of the invention pertains to host cells into which a recombinant expression vector of the invention has been introduced. The terms "host cell" and "recombinant host cell" are used interchangeably herein. It is understood that such terms refer not only to the particular subject cell but also to the progeny or potential progeny of such a cell. Because certain modifications may occur in succeeding generations due to either mutation or environmental influences, such progeny may not, in fact, be identical to the parent cell, but are still included within the scope of the term as used herein.

A host cell can be any prokaryotic or eukaryotic cell. For example, the Oncoseq protein can be expressed in bacterial cells such as *E. coli*, insect cells, yeast or mammalian cells (such as Chinese hamster ovary cells (CHO) or COS cells). Other suitable host cells are known to those skilled in the art.

Vector DNA can be introduced into prokaryotic or eukaryotic cells via conventional transformation or transfection techniques. As used herein, the terms "transformation" and "transfection" are intended to refer to a variety of art-recognized techniques for introducing foreign nucleic acid (e.g., DNA) into a host cell, including calcium phosphate or calcium chloride co-precipitation, DEAE-dextran-mediated transfection, lipofection, or electroporation. Suitable methods for transforming or transfecting host cells can be found in Sambrook, et al. (2001), Ausubel et al. (2002), and other laboratory manuals.

For stable transfection of mammalian cells, it is known that, depending upon the expression vector and transfection technique used, only a small fraction of cells may integrate the foreign DNA into their genome. In order to identify and select these integrants, a gene that encodes a selectable marker (e.g., resistance to antibiotics) is generally introduced into the host cells along with the gene of interest. Various selectable markers include those that confer resistance to drugs, such as G418, hygromycin and methotrexate. Nucleic acid encoding a selectable marker can be introduced into a host cell on the same vector as that encoding the Oncoseq polypeptide or can be introduced on a separate vector. Cells stably transfected with the introduced nucleic acid can be identified by drug selection (e.g., cells that have incorporated the selectable marker gene will survive, while the other cells die).

A host cell of the invention, such as a prokaryotic or eukaryotic host cell in culture, can be used to produce (i.e., express) the Oncoseq protein. Accordingly, the invention further provides methods for producing the Oncoseq protein using the host cells of the invention. In one embodiment, the method comprises culturing the host cell of invention (into which a recombinant expression vector encoding the Oncoseq protein has been introduced) in a suitable medium such that the Oncoseq protein is produced. In another embodiment, the method further comprises isolating the Oncoseq protein from the medium or the host cell.

Transgenic Animals

The host cells of the invention can also be used to produce nonhuman transgenic animals. For example, in one embodiment, a host cell of the invention is a fertilized oocyte or an embryonic stem cell into which Oncoseq protein-coding sequences have been introduced. Such host cells can then be used to create non-human transgenic animals in which exogenous Oncoseq protein sequences have been introduced into their genome or homologous recombinant animals in which endogenous Oncoseq protein sequences have been altered. Such animals are useful for studying the function and/or activity of the Oncoseq proteins and for identifying and/or evaluating modulators of Oncoseq protein activity. As used herein, a "transgenic animal" is a non-human animal, preferably a mammal, more preferably a rodent such as a rat or mouse, in which one or more of the cells of the animal includes a transgene. Other examples of transgenic animals include non-human primates, sheep, dogs, cows, goats, chickens, amphibians, etc. A transgene is exogenous DNA that is integrated into the genome of a cell from which a transgenic animal develops and that remains in the genome of the mature animal, thereby directing the expression of an encoded gene product in one or more cell types or tissues of the transgenic animal. As used herein, a "homologous recombinant animal" is a non-human animal, preferably a mammal, more preferably a mouse, in which an endogenous Oncoseq gene has been altered by homologous recombination between the endogenous gene and an exogenous DNA molecule introduced into a cell of the animal, e.g., an embryonic cell of the animal, prior to development of the animal.

A transgenic animal of the invention can be created by introducing Oncoseq protein-encoding nucleic acid into the male pronuclei of a fertilized oocyte, e.g., by microinjection, retroviral infection, and allowing the oocyte to develop in a pseudopregnant female foster animal. The human Oncoseq DNA sequence of SEQ ID NOS:1 and 3 can be introduced as a transgene into the genome of a non-human animal. Alternatively, a nonhuman homologue of the human Oncoseq gene, such as a mouse Oncoseq gene, can be isolated based on hybridization to the human Oncoseq cDNA (described further above) and used as a transgene. Intronic sequences and polyadenylation signals can also be included in the transgene to increase the efficiency of expression of the transgene. A tissue-specific regulatory sequence(s) can be operably linked to the Oncoseq transgene to direct expression of Oncoseq protein to particular cells.

Methods for generating transgenic animals via embryo manipulation and microinjection, particularly animals such as mice, have become conventional in the art and are described, for example, in U.S. Pat. Nos. 4,736,866; 4,870,009; and 4,873,191; and Hogan 1986, In: MANIPULATING THE MOUSE EMBRYO, Cold Spring Harbor Laboratory Press, Cold Spring Harbor, N.Y. Similar methods are used for production of other transgenic animals. A transgenic founder animal can be identified based upon the presence of the Oncoseq transgene in its genome and/or expression of Oncoseq mRNA in tissues or cells of the animals. A transgenic founder animal can then be used to breed additional animals carrying the transgene. Moreover, transgenic animals carrying a transgene encoding an Oncoseq protein can further be bred to other transgenic animals carrying other transgenes.

To create a homologous recombinant animal, a vector is prepared which contains at least a portion of an Oncoseq gene into which a deletion, addition or substitution has been introduced to thereby alter, e.g., functionally disrupt, the Oncoseq gene. The Oncoseq gene can be a human gene (e.g., SEQ ID NOS:1 and 3), but more preferably, is a non-human homologue of a human Oncoseq gene. For example, a mouse homologue of human Oncoseq gene of SEQ ID NOS:1 and 3 can be used to construct a homologous recombination vector suitable for altering an endogenous Oncoseq gene in the mouse genome. In one embodiment, the vector is designed such that, upon homologous recombination, the endogenous Oncoseq gene is functionally disrupted (i.e., no longer encodes a functional protein; also referred to as a "knock out" vector).

Alternatively, the vector can be designed such that, upon homologous recombination, the endogenous Oncoseq gene is mutated or otherwise altered but still encodes functional protein (e.g., the upstream regulatory region can be altered to thereby alter the expression of the endogenous Oncoseq protein). In the homologous recombination vector, the altered portion of the Oncoseq gene is flanked at its 5' and 3' ends by additional nucleic acid of the Oncoseq gene to allow for homologous recombination to occur between the exogenous Oncoseq protein gene carried by the vector and an endogenous Oncoseq protein gene in an embryonic stem cell. The additional flanking Oncoseq protein nucleic acid is of sufficient length for successful homologous recombination with the endogenous gene. Typically, several kilobases of flanking DNA (both at the 5' and 3' ends) are included in the vector. See e.g., Thomas et al. (1987) *Cell* 51:503 for a description of homologous recombination vectors. The vector is introduced into an embryonic stem cell line (e.g., by electroporation) and cells in which the introduced Oncoseq protein gene has homologously recombined with the endogenous Oncoseq protein gene are selected (see e.g., Li et al. (1992) *Cell* 69:915).

The selected cells are then injected into a blastocyst of an animal (e.g., a mouse) to form aggregation chimeras. See e.g., Bradley 1987, In: TERATOCARCINOMAS AND EMBRYONIC STEM CELLS: A PRACTICAL APPROACH, Robertson, ed. IRL, Oxford, pp. 113-152. A chimeric embryo can then be implanted into a suitable pseudopregnant female foster animal and the embryo brought to term. Progeny harboring the homologously recombined DNA in their germ cells can be used to breed animals in which all cells of the animal contain the homologously recombined DNA by germline transmission of the transgene. Methods for constructing homologous recombination vectors and homologous recombinant animals are described further in Bradley (1991) *Curr Opin Biotechnol* 2:823-829; PCT International Publication Nos.: WO 90/1184; WO 91/01140; WO 92/0968; and WO 93/04169.

In another embodiment, transgenic non-humans animals can be produced that contain selected systems that allow for regulated expression of the transgene. One example of such a system is the cre/loxP recombinase system of bacteriophage P1. For a description of the cre/loxP recombinase system, see, e.g., Lakso el al. (1992) *Proc. Natl. Acad. Sci. USA* 89:6232-6236. Another example of a recombinase system is the FLP recombinase system of *Saccharomyces cerevisiae* (O'Gorman et al. 1991) *Science* 251:181-185. If a cre/loxP recombinase system is used to regulate expression of the transgene, animals containing transgenes encoding both the Cre recombinase and a selected protein are required. Such animals can be provided through the construction of "double" transgenic animals, e.g., by mating two transgenic animals, one containing a transgene encoding a selected protein and the other containing a transgene encoding a recombinase.

Clones of the non-human transgenic animals described herein can also be produced according to the methods described in Wilmut et al. (1997) *Nature* 385:810-813. In brief, a cell, e.g., a somatic cell, from the transgenic animal can be isolated and induced to exit the growth cycle and enter $G_0$ phase. The quiescent cell can then be fused, e.g., through the use of electrical pulses, to an enucleated oocyte from an animal of the same species from which the quiescent cell is isolated. The reconstructed oocyte is then cultured such that it develops to morula or blastocyte and then transferred to pseudopregnant female foster animal. The offspring borne of this female foster animal will be a clone of the animal from which the cell, e.g., the somatic cell, is isolated.

Pharmaceutical Compositions

The Oncoseq nucleic acid molecules, Oncoseq proteins, and anti-Oncoseq protein antibodies of the invention, and derivatives, fragments, analogs and homologs thereof are designated "active compounds" or "Therapeutics" herein. Additionally, low molecular weight compounds which have the property that they either bind to the Oncoseq nucleic acid molecules, the Oncoseq proteins, and the anti-Oncoseq protein antibodies of the invention, and derivatives, fragments, analogs and homologs thereof, or induce pharmacological agonist or antagonist responses commonly ascribed to an Oncoseq nucleic acid molecule, an Oncoseq protein, and derivatives, fragments, analogs and homologs thereof, are also termed "active compounds" or "Therapeutics" herein. These Therapeutics can be incorporated into pharmaceutical compositions suitable for administration to a subject. Such compositions typically comprise the nucleic acid molecule, protein, or antibody and a pharmaceutically acceptable carrier.

As used herein, "pharmaceutically acceptable carrier" is intended to include any and all solvents, dispersion media, coatings, antibacterial and antifungal agents, isotonic and absorption delaying agents, and the like, compatible with pharmaceutical administration. Suitable carriers are described in textbooks such as Remington's Pharmaceutical Sciences, Gennaro AR (Ed.) $20^{th}$ edition (2000) Williams & Wilkins PA, USA, and Wilson and Gisvold's Textbook of Organic Medicinal and Pharmaceutical Chemistry, by Delgado and Remers, Lippincott-Raven., which are incorporated herein by reference. Preferred examples of components that may be used in such carriers or diluents include, but are not limited to, water, saline, phosphate salts, carboxylate salts, amino acid solutions, Ringer's solutions, dextrose solution, and 5% human serum albumin. Liposomes and non-aqueous vehicles such as fixed oils may also be used. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

A pharmaceutical composition of the invention is formulated to be compatible with its intended route of administration. Examples of routes of administration include parenteral, e.g., intravenous, intradermal, subcutaneous, oral (e.g., inhalation), transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite, chelating agents such as ethylenediaminetetraacetic acid; buffers such as acetates, citrates or phosphates, and agents for the adjustment of tonicity such as sodium chloride or dextrose. The pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringeability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound (e.g., an Oncoseq protein or anti-Oncoseq protein antibody) in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile powders for the preparation of sterile injectable solutions, methods of preparation are vacuum drying and freeze-drying that yields a powder of the active ingredient plus any additional desired ingredient from a previously sterile-filtered solution thereof.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from pressured container or dispenser which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The compounds can also be prepared in the form of suppositories (e.g., with conventional suppository bases such as cocoa butter and other glycerides) or retention enemas for rectal delivery.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

Sustained-release preparations can be prepared. Suitable examples of sustained-release preparations include semipermeable matrices of solid hydrophobic polymers containing the antibody, which matrices are in the form of shaped articles, e.g., films, or microcapsules. Examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and γ ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), and poly-D-(−)-3-hydroxybutyric acid. While polymers such as ethylene-vinyl acetate and lactic acid-glycolic acid enable release of molecules for over 100 days, certain hydrogels release pharmaceutical active agents over shorter time periods.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved.

The nucleic acid molecules of the invention can be inserted into vectors and used as gene therapy vectors. As described herein, gene therapy vectors also comprehend the use of antisense polynucleotides and inhibitory polynucleotides including microRNA (mRNA), modified mRNA, small inhibitory RNA (si RNA), and modified siRNA, wherein modifications are introduced as described in this invention at least to confer stability on the molecules. Gene therapy vectors can be delivered to a subject by any of a number of routes, e.g., as described in U.S. Pat. No. 5,703,055. Delivery can thus also include, e.g., intravenous injection, local administration (see U.S. Pat. No. 5,328,470) or stereotactic injection (see e.g., Chen et al. (1994) *Proc. Natl. Acad. Sci. USA* 91:3054-3057). The pharmaceutical preparation of the gene therapy vector can include the gene therapy vector in an acceptable diluent, or can comprise a slow release matrix in which the gene delivery vehicle is imbedded. Alternatively, where the complete gene delivery vector can be produced intact from recombinant cells, e.g., retroviral vectors, the pharmaceutical preparation can include one or more cells that produce the gene delivery system.

The pharmaceutical compositions can be included in a kit, e.g., in a container, pack, or dispenser together with instructions for administration.

Also within the invention is the use of a therapeutic in the manufacture of a medicament for treating a syndrome associated with a human disease, the disease selected from an Oncoseq-associated disorder, wherein said therapeutic is selected from the group consisting of an Oncoseq polypeptide, an Oncoseq nucleic acid, and an anti-Oncoseq protein antibody.

Additional Uses and Methods of the Invention

The nucleic acid molecules, proteins, protein homologues, and antibodies described herein can be used in one or more of the following methods: (a) screening assays; (b) predictive medicine (e.g., diagnostic assays, prognostic assays, monitoring clinical trials, and pharmacogenomics); and (c) methods of treatment (e.g., therapeutic and prophylactic).

The isolated nucleic acid molecules of the invention can be used to express an Oncoseq protein (e.g., via a recombinant expression vector in a host cell in gene therapy applications), to detect an Oncoseq mRNA (e.g., in a biological sample) or a genetic lesion in an Oncoseq gene, and to modulate Oncoseq protein activity, as described further below. In addition, the Oncoseq proteins can be used to screen drugs or compounds that modulate the Oncoseq protein activity or expression as well as to treat disorders characterized by insufficient or excessive production of the Oncoseq protein, for example proliferative or differentiative disorders, or production of the Oncoseq protein forms that have decreased or aberrant activity compared to the Oncoseq wild type protein. In addition, the anti-Oncoseq protein antibodies of the invention can be used to detect and isolate Oncoseq proteins and modulate Oncoseq protein activity.

This invention further pertains to novel agents identified by the above described screening assays and uses thereof for treatments as described herein.

Screening Assays

The invention provides methods (also referred to herein as "screening assays") for identifying modulators, i.e., candidate or test compounds or agents (e.g., proteins, polypeptides, nucleic acids or polynucleotides, peptides, peptidomimetics, small molecules including agonists or antagonists, or other drugs) that bind to Oncoseq proteins or have a stimulatory or inhibitory effect on, for example, Oncoseq protein expression or Oncoseq protein activity. Details of functional assays are provided herein further below Any of the assays described, as well as additional assays known to practitioners in the fields of pharmacology, hematology, internal medicine, oncology and the like, may be employed in order to screen candidate substance for their properties as therapeutic agents. As noted, the therapeutic agents of the invention encompass proteins, polypeptides, nucleic acids or polynucleotides, peptides, peptidomimetics, small molecules including agonists or antagonists, or other drugs described herein.

In one embodiment, the invention provides assays for screening candidate or test compounds which bind to or modulate the activity of an Oncoseq protein or polypeptide or biologically active portion thereof. The test compounds of the present invention can be obtained using any of the numerous approaches in combinatorial library methods known in the art, including: biological libraries; spatially addressable parallel solid phase or solution phase libraries; synthetic library methods requiring deconvolution; the "one-bead one-compound" library method; and synthetic library methods using affinity chromatography selection. The biological library approach is limited to peptide libraries, while the other four approaches are applicable to peptide, non-peptide oligomer or small molecule libraries of compounds (Lam (1997) *Anticancer Drug Des* 12:145).

Examples of methods for the synthesis of molecular libraries can be found in the art, for example in: DeWitt et al. (1993) *Proc Natl Acad Sci U.S.A.* 90:6909; Erb et al. (1994) *Proc Natl Acad Sci U.S.A.* 91:11422; Zuckermann et al. (1994) *J Med Chem* 37:2678; Cho et al. (I 993) *Science* 261:1303; Carrell et al. (1994) *Angew Chem Int Ed Engl* 33:2059; Carell et al. (1994) *Angew Chem Int Ed Engl* 33:2061; and Gallop et al. (1994) *J Med Chem* 37:1233.

Libraries of compounds may be presented in solution (e.g., Houghten (1992) *Biotechniques* 13:412-421), or on beads (Lam (1991) *Nature* 354:82-84), on chips (Fodor (1993) *Nature* 364:555-556), bacteria (Ladner U.S. Pat. No. 5,223,409), spores (Ladner U.S. Pat. No. '409), plasmids (Cull et al. (1992) *Proc Natl Acad Sci USA* 89:1865-1869) or on phage (Scott and Smith (1990) *Science* 249:386-390; Devlin (1990) *Science* 249:404-406; Cwirla et al. (1990) *Proc Natl Acad Sci U.S.A.* 87:6378-6382; Felici (1991) *J Mol Biol* 222:301-310; Ladner above.).

In one embodiment, an assay is a cell-based assay in which a cell which expresses a membrane-bound form of an Oncoseq protein, or a biologically active portion thereof, on the cell surface is contacted with a test compound and the ability of the test compound to bind to an Oncoseq protein determined. The cell, for example, can of mammalian origin or a yeast cell. Determining the ability of the test compound to bind to the Oncoseq protein can be accomplished, for example, by coupling the test compound with a radioisotope or enzymatic label such that binding of the test compound to the Oncoseq protein or biologically active portion thereof can be determined by detecting the labeled compound in a complex. For example, test compounds can be labeled with $^{125}I$, $^{35}S$, $^{14}C$, or $^{3}H$, either directly or indirectly, and the radioisotope detected by direct counting of radioemission or by scintillation counting.

Alternatively, test compounds can be enzymatically labeled with, for example, horseradish peroxidase, alkaline phosphatase, or luciferase, and the enzymatic label detected by determination of conversion of an appropriate substrate to product. In one embodiment, the assay comprises contacting a cell which expresses a membrane-bound form of an Oncoseq protein, or a biologically active portion thereof, on the cell surface with a known compound which binds an Oncoseq protein to form an assay mixture, contacting the assay mixture with a test compound, and determining the ability of the test compound to interact with an Oncoseq protein, wherein determining the ability of the test compound to interact with an Oncoseq protein comprises determining the ability of the test compound to preferentially bind to an Oncoseq protein or a biologically active portion thereof as compared to the known compound.

In another embodiment, an assay is a cell-based assay comprising contacting a cell expressing a membrane-bound form of an Oncoseq protein, or a biologically active portion thereof on the cell surface with a test compound and determining the ability of the test compound to modulate (e.g., stimulate or inhibit) the activity of the Oncoseq protein or biologically active portion thereof. Determining the ability of the test compound to modulate the activity of an Oncoseq protein or a biologically active portion thereof can be accomplished, for example, by determining the ability of the Oncoseq protein to bind to or interact with an Oncoseq protein target molecule. As used herein, a "target molecule"

is a molecule with which an Oncoseq protein binds or interacts in nature, for example, a molecule on the surface of a cell which expresses an Oncoseq protein interacting protein, a molecule on the surface of a second cell, a molecule in the extracellular milieu, a molecule associated with the internal surface of a cell membrane or a cytoplasmic molecule. An Oncoseq protein target molecule can be a non-Oncoseq protein molecule or an Oncoseq protein or polypeptide of the present invention. In one embodiment, an Oncoseq protein target molecule is a component of a signal transduction pathway that facilitates transduction of an extracellular signal (e.g., a signal generated by binding of a compound to a membrane-bound Oncoseq protein molecule) through the cell membrane and into the cell. The target, for example, can be a second intercellular protein that has catalytic activity or a protein that facilitates the association of signaling molecules with the Oncoseq protein.

Determining the ability of the Oncoseq protein to bind to or interact with an Oncoseq protein target molecule can be accomplished by one of the methods described above for determining direct binding. In one embodiment, determining the ability of the Oncoseq protein to bind to or interact with an Oncoseq protein target molecule can be accomplished by determining the activity of the target molecule. For example, the activity of the target molecule can be determined by detecting induction of a cellular second messenger of the target (i.e. intracellular $Ca^{2+}$, diacylglycerol $IP_3$, etc.), detecting catalytic/enzymatic activity of the target an appropriate substrate, detecting the induction of a reporter gene (comprising an Oncoseq-responsive regulatory element operatively linked to a nucleic acid encoding a detectable marker, e.g., luciferase), or detecting a cellular response, for example, cell survival, cellular differentiation, or cell proliferation.

In yet another embodiment, an assay of the present invention is a cell-free assay comprising contacting an Oncoseq protein or biologically active portion thereof with a test compound and determining the ability of the test compound to bind to the Oncoseq protein or biologically active portion thereof. Binding of the test compound to the Oncoseq protein can be determined either directly or indirectly as described above. In one embodiment, the assay comprises contacting the Oncoseq protein or biologically active portion thereof with a known compound which binds Oncoseq protein to form an assay mixture, contacting the assay mixture with a test compound, and determining the ability of the test compound to interact with an Oncoseq protein, wherein determining the ability of the test compound to interact with an Oncoseq protein comprises determining the ability of the test compound to preferentially bind to an Oncoseq protein or biologically active portion thereof as compared to the known compound.

In another embodiment, an assay is a cell-free assay comprising contacting an Oncoseq protein or biologically active portion thereof with a test compound and determining the ability of the test compound to modulate (e.g., stimulate or inhibit) the activity of the Oncoseq protein or biologically active portion thereof. Determining the ability of the test compound to modulate the activity of an Oncoseq protein can be accomplished, for example, by determining the ability of the Oncoseq protein to bind to an Oncoseq protein target molecule by one of the methods described above for determining direct binding. In an alternative embodiment, determining the ability of the test compound to modulate the activity of an Oncoseq protein can be accomplished by determining the ability of the Oncoseq protein to further modulate an Oncoseq protein target molecule. For example, the catalytic/enzymatic activity of the target molecule on an appropriate substrate can be determined as previously described.

In yet another embodiment, the cell-free assay comprises contacting the Oncoseq protein or biologically active portion thereof with a known compound which binds an Oncoseq protein to form an assay mixture, contacting the assay mixture with a test compound, and determining the ability of the test compound to interact with an Oncoseq protein, wherein determining the ability of the test compound to interact with an Oncoseq protein comprises determining the ability of the Oncoseq protein to preferentially bind to or modulate the activity of an Oncoseq protein target molecule.

The cell-free assays of the present invention are amenable to use of both the soluble form or the membrane-bound form of an Oncoseq protein. In the case of cell-free assays comprising the membrane-bound form of an Oncoseq protein, it may be desirable to utilize a solubilizing agent such that the membrane-bound form of an Oncoseq protein is maintained in solution. Examples of such solubilizing agents include non-ionic detergents such as n-octylglucoside, n-dodecylglucoside, n-dodecylmaltoside, octanoyl-N-methylglucamide, decanoyl-N-methylglucamide, Triton® X-100, Triton® X-114, Thesit®, Isotridecypoly(ethylene glycol ether)$_n$, N-dodecyl-N,N-dimethyl-3-ammonio-1-propane sulfonate, 3-(3-cholamidopropyl)dimethylamminiol-1-propane sulfonate (CHAPS), or 3-(3-cholamidopropyl)dimethylamminiol-2-hydroxy-1-propane sulfonate (CHAPSO).

In more than one embodiment of the above assay methods of the present invention, it may be desirable to immobilize either an Oncoseq protein or its target molecule to facilitate separation of complexed from uncomplexed forms of one or both of the proteins, as well as to accommodate automation of the assay. Binding of a test compound to an Oncoseq protein, or interaction of an Oncoseq protein with a target molecule in the presence and absence of a candidate compound, can be accomplished in any vessel suitable for containing the reactants. Examples of such vessels include microtiter plates, test tubes, and micro-centrifuge tubes. In one embodiment, a fusion protein can be provided that adds a domain that allows one or both of the proteins to be bound to a matrix. For example, GST-Oncoseq protein fusion proteins or GST-target fusion proteins can be adsorbed onto glutathione sepharose beads (Sigma Chemical, St. Louis, Mo.) or glutathione derivatized microtiter plates, that are then combined with the test compound or the test compound and either the non-adsorbed target protein or an Oncoseq protein, and the mixture is incubated under conditions conducive to complex formation (e.g., at physiological conditions for salt and pH). Following incubation, the beads or microtiter plate wells are washed to remove any unbound components, the matrix immobilized in the case of beads, complex determined either directly or indirectly, for example, as described above. Alternatively, the complexes can be dissociated from the matrix, and the level of Oncoseq protein binding or activity determined using standard techniques.

Other techniques for immobilizing proteins on matrices can also be used in the screening assays of the invention. For example, either the Oncoseq protein or its target molecule can be immobilized utilizing conjugation of biotin and streptavidin. Biotinylated Oncoseq protein or target molecules can be prepared from biotin-NHS (N-hydroxy-succinimide) using techniques well known in the art (e.g., biotinylation kit, Pierce Chemicals, Rockford, ILL.), and immobilized in the wells of streptavidin-coated 96 well plates (Pierce Chemical). Alternatively, antibodies reactive with Oncoseq protein or target molecules, but which do not interfere with binding of the Oncoseq protein to its target molecule, can be derivatized to the wells of the plate, and unbound target or Oncoseq protein trapped in the wells by antibody conjugation. Methods for detecting such complexes, in addition to those described above for the GST-immobilized complexes, include immunodetection of complexes using antibodies reactive with the Oncoseq protein or target molecule, as well as enzyme-linked assays that rely on detecting an enzymatic activity associated with the Oncoseq protein or target molecule.

In another embodiment, modulators of Oncoseq expression are identified in a method wherein a cell is contacted with a candidate compound and the expression of an Oncoseq mRNA or protein in the cell is determined. The level of expression of an Oncoseq mRNA or protein in the presence of the candidate compound is compared to the level of expression of an Oncoseq mRNA or protein in the absence of the candidate compound. The candidate compound can then be identified as a modulator of Oncoseq expression based on this comparison. For example, when expression of an Oncoseq mRNA or protein is greater (statistically significantly greater) in the presence of the candidate compound than in its absence, the candidate compound is identified as a stimulator of an Oncoseq mRNA or protein expression. Alternatively, when expression of an Oncoseq mRNA or protein is less (statistically significantly less) in the presence of the candidate compound than in its absence, the candidate compound is identified as an inhibitor of an Oncoseq mRNA or protein expression. The level of an Oncoseq mRNA or protein expression in the cells can be determined by methods described herein for detecting Oncoseq mRNA or protein.

In yet another aspect of the invention, the Oncoseq proteins can be used as "bait proteins" in a two-hybrid assay or three hybrid assay (see, e.g., U.S. Pat. No. 5,283,317; Zervos et al. (1993) Cell 72:223-232, Madura et al. (1993) J Biol Chem 268:12046-12054; Bartel el al. (1993) Biotechniques 14:920-924; Iwabuchi et al. (1993) Oncogene 8:1693-1696; and Brent WO94/10300), to identify other proteins that bind to or interact with the Oncoseq protein ("Oncoseq protein-binding proteins" or "Oncoseq protein-bp") and modulate Oncoseq protein activity. Such Oncoseq protein-binding proteins are also likely to be involved in the propagation of signals by the Oncoseq proteins as, for example, upstream or downstream elements of the Oncoseq protein pathway.

The two-hybrid system is based on the modular nature of most transcription factors, which consist of separable DNA-binding and activation domains. Briefly, the assay utilizes two different DNA constructs. In one construct, the gene that codes for an Oncoseq protein is fused to a gene encoding the DNA binding domain of a known transcription factor (e.g., GAL-4). In the other construct, a DNA sequence, from a library of DNA sequences, that encodes an unidentified protein ("prey" or "sample") is fused to a gene that codes for the activation domain of the known transcription factor. If the "bait" and the "prey" proteins are able to interact, in vivo, forming an Oncoseq protein-dependent complex, the DNA-binding and activation domains of the transcription factor are brought into close proximity. This proximity allows transcription of a reporter gene (e.g., LacZ) that is operably linked to a transcriptional regulatory site responsive to the transcription factor. Expression of the reporter gene can be detected and cell colonies containing the functional transcription factor can be isolated and used to obtain the cloned gene that encodes the protein which interacts with the Oncoseq protein.

Screening can also be performed in vivo. For example, in one embodiment, the invention includes a method for screening for a modulator of activity or of latency or predisposition to an Oncoseq protein-associated disorder by administering a test compound or to a test animal at increased risk for an Oncoseq-associated disorder. In some embodiments, the test animal recombinantly expresses an Oncoseq polypeptide. Activity of the polypeptide in the test animal after administering the compound is measured, and the activity of the protein in the test animal is compared to the activity of the polypeptide in a control animal not administered said polypeptide. A change in the activity of said polypeptide in said test animal relative to the control animal indicates the test compound is a modulator of latency of or predisposition to an Oncoseq-associated disorder.

In some embodiments, the test animal is a recombinant test animal that expresses a test protein transgene or expresses the transgene under the control of a promoter at an increased level relative to a wild-type test animal. Preferably, the promoter is not the native gene promoter of the transgene.

This invention further pertains to novel agents identified by the above-described screening assays and uses thereof for treatments as described herein.

Predictive Medicine

The present invention also pertains to the field of predictive medicine in which diagnostic assays, prognostic assays, pharmacogenomics, and monitoring clinical trials are used for prognostic (predictive) purposes to thereby treat an individual prophylactically. Accordingly, one aspect of the present invention relates to diagnostic assays for determining an Oncoseq protein and/or nucleic acid expression as well as Oncoseq protein activity, in the context of a biological sample (e.g., blood, serum, cells, tissue) to thereby determine whether an individual is afflicted with a disease or disorder, or is at risk of developing a disorder, associated with aberrant Oncoseq expression or activity. The invention also provides for prognostic (or predictive) assays for determining whether an individual is at risk of developing a disorder associated with an Oncoseq protein, nucleic acid expression or activity. For example, mutations in an Oncoseq gene can be assayed in a biological sample. Such assays can be used for prognostic or predictive purpose to thereby prophylactically treat an individual prior to the onset of a disorder characterized by or associated with Oncoseq protein, nucleic acid expression or activity.

Another aspect of the invention provides methods for determining Oncoseq protein, nucleic acid expression or Oncoseq protein activity in an individual to thereby select appropriate therapeutic or prophylactic agents for that individual (referred to herein as "pharmacogenomics"). Pharmacogenomics allows for the selection of agents (e.g., drugs) for therapeutic or prophylactic treatment of an individual based on the genotype of the individual (e.g., the genotype of the individual examined to determine the ability of the individual to respond to a particular agent.)

Yet another aspect of the invention pertains to monitoring the influence of agents (e.g., drugs, compounds) on the expression or activity of an Oncoseq protein in clinical trials.

These and other agents are described in further detail in the following sections.

Diagnostic Assays

Other conditions in which proliferation of cells plays a role include tumors, restenosis, psoriasis, Dupuytren's contracture, diabetic complications, Kaposi's sarcoma and rheumatoid arthritis.

An Oncoseq polypeptide may be used to identify an interacting polypeptide a sample or tissue. The method comprises contacting the sample or tissue with the Oncoseq protein, allowing formation of a complex between the Oncoseq polypeptide and the interacting polypeptide, and detecting the complex, if present.

The proteins of the invention may be used to stimulate production of antibodies specifically binding the proteins. Such antibodies may be used in immunodiagnostic procedures to detect the occurrence of the protein in a sample. The proteins of the invention may be used to stimulate cell growth and cell proliferation in conditions in which such growth would be favorable. An example would be to counteract toxic side effects of chemotherapeutic agents on, for example, hematopoiesis and platelet formation, linings of the gastrointestinal tract, and hair follicles. They may also be used to stimulate new cell growth in neurological disorders including, for example, Alzheimer's disease. Alternatively, antagonistic treatments may be administered in which an antibody specifically binding the Oncoseq protein-like proteins of the invention would abrogate the specific growth-inducing effects of the proteins. Such antibodies may be useful, for example, in the treatment of proliferative disorders including various tumors and benign hyperplasias.

Polynucleotides or oligonucleotides corresponding to any one portion of the Oncoseq nucleic acids of SEQ ID NOS:1 and 3 may be used to detect DNA containing a corresponding ORF gene, or detect tile expression of a corresponding Oncoseq gene, or Oncoseq protein-like gene. For example, an Oncoseq nucleic acid expressed in a particular cell or tissue can be used to identify the presence of that particular cell type.

An exemplary method for detecting the presence or absence of an Oncoseq in a biological sample involves obtaining a biological sample from a test subject and contacting the biological sample with a compound or an agent capable of detecting an Oncoseq protein or nucleic acid (e.g., mRNA, genomic DNA) that encodes an Oncoseq protein such that the presence of an Oncoseq is detected in the biological sample. An agent for detecting an Oncoseq mRNA or genomic DNA is a labeled nucleic acid probe capable of hybridizing to an Oncoseq mRNA or genomic DNA. The nucleic acid probe can be, for example, a full-length Oncoseq nucleic acid, such as the nucleic acid of SEQ ID NOS:1 and 3, or a portion thereof, such as an oligonucleotide of at least 15, 30, 50, 100, 250 or 500 nucleotides in length and sufficient to specifically hybridize under stringent conditions to an Oncoseq mRNA or genomic DNA, as described above. Other suitable probes-for use in the diagnostic assays of the invention are described herein.

An agent for detecting an Oncoseq protein is an antibody capable of binding to an Oncoseq protein, preferably an antibody with a detectable label. Antibodies can be polyclonal, or more preferably, monoclonal. An intact antibody, or a fragment thereof (e.g., Fab or F(ab')$_2$) can be used. The term "labeled", with regard to the probe or antibody, is intended to encompass direct labeling of the probe or antibody by coupling (i.e., physically linking) a detectable substance to the probe or antibody, as well as indirect labeling of the probe or antibody by reactivity with another reagent that is directly labeled. Examples of indirect labeling include detection of a primary antibody using a fluorescently labeled secondary antibody and end-labeling of a DNA probe with biotin such that it can be detected with fluorescently labeled streptavidin. The term "biological sample" is intended to include tissues, cells and biological fluids isolated from a subject, as well as tissues, cells and fluids present within a subject. That is, the detection method of the invention can be used to detect an Oncoseq mRNA, protein, or genomic DNA in a biological sample in vitro as well as in vivo. For example, in vitro techniques for detection of an Oncoseq mRNA include Northern hybridizations and in situ hybridizations. In vitro techniques for detection of an Oncoseq protein include enzyme linked immunosorbent assays (ELISAs), Western blots, immunoprecipitations and immunofluorescence. In vitro techniques for detection of an Oncoseq genomic DNA include Southern hybridizations. Furthermore, in vivo techniques for detection of an Oncoseq protein include introducing into a subject a labeled anti-Oncoseq protein antibody. For example, the antibody can be labeled with a radioactive marker whose presence and location in a subject can be detected by standard imaging techniques.

In one embodiment, the biological sample contains protein molecules from the test subject. Alternatively, the biological sample can contain mRNA molecules from the test subject or genomic DNA molecules from the test subject. A preferred biological sample is a peripheral blood leukocyte sample isolated by conventional means from a subject.

In another embodiment, the methods further involve obtaining a control biological sample from a control subject, contacting the control sample with a compound or agent capable of detecting an Oncoseq protein, mRNA, or genomic DNA, such that the presence of an Oncoseq protein, mRNA or genomic DNA is detected in the biological sample, and comparing the presence of an Oncoseq protein, mRNA or genomic DNA in the control sample with the presence of an Oncoseq protein, mRNA or genomic DNA in the test sample.

The invention also encompasses kits for detecting the presence of an Oncoseq in a biological sample. For example, the kit can comprise: a labeled compound or agent capable of detecting an Oncoseq protein or mRNA in a biological sample; means for determining the amount of an Oncoseq in the sample; and means for comparing the amount of an Oncoseq in the sample with a standard. The compound or agent can be packaged in a suitable container. The kit can further comprise instructions for using the kit to detect an Oncoseq protein or nucleic acid.

Prognostic Assays

The diagnostic methods described herein can furthermore be utilized to identify subjects having or at risk of developing a disease or disorder associated with aberrant Oncoseq expression or activity. For example, the assays described herein, such as the preceding diagnostic assays or the following assays, can be utilized to identify a subject having or at risk of developing a disorder associated with an Oncoseq protein, nucleic acid expression or activity in, e.g., proliferative or differentiative disorders such as hyperplasias, tumors, restenosis, psoriasis, Dupuytren's contracture, diabetic complications, or rheumatoid arthritis, etc.; and glia-associated disorders such as cerebral lesions, diabetic neuropathies, cerebral edema, senile dementia, Alzheimer's disease, etc. Alternatively, the prognostic assays can be utilized to identify a subject having or at risk for developing a disease or disorder. Thus, the present invention provides a method for identifying a disease or disorder associated with aberrant Oncoseq expression or activity in which a test sample is obtained from a subject and an Oncoseq protein or nucleic acid (e.g., mRNA, genomic DNA) is detected, wherein the presence of an Oncoseq protein or nucleic acid is, diagnostic for a subject having or at risk of developing a disease or disorder associated with aberrant Oncoseq expression or activity. As used herein, a "test sample" refers to a biological sample obtained from a subject of interest. For example, a test sample can be a biological fluid (e.g., serum), cell sample, or tissue.

Furthermore, the prognostic assays described herein can be used to determine whether a subject can be administered an agent (e.g., an agonist, antagonist, peptidomimetic, protein, peptide, nucleic acid, small molecule, or other drug candidate) to treat a disease or disorder associated with aberrant Oncoseq expression or activity. For example, such methods can be used to determine whether a subject can be effectively treated with an agent for a disorder, such as a proliferative disorder, differentiative disorder, glia-associated disorders, etc. Thus, the present invention provides methods for determining whether a subject can be effectively treated with an agent for a disorder associated with aberrant Oncoseq expression or activity in which a test sample is obtained and an Oncoseq protein or nucleic acid is detected (e.g., wherein the presence of an Oncoseq protein or nucleic acid is diagnostic for a subject that can be administered the agent to treat a disorder associated with aberrant Oncoseq expression or activity.)

The methods of the invention can also be used to detect genetic lesions in an Oncoseq gene, thereby determining if a subject with the lesioned gene is at risk for, or suffers from, a proliferative disorder, differentiative disorder, glia-associated disorder, etc. In various embodiments, the methods include detecting, in a sample of cells from the subject, the presence or absence of a genetic lesion characterized by at least one of an alteration affecting the integrity of a gene encoding an Oncoseq protein, or the mis-expression of the Oncoseq gene. For example, such genetic lesions can be detected by ascertaining the existence of at least one of (1) a deletion of one or more nucleotides from an Oncoseq gene; (2) an addition of one or more nucleotides to an Oncoseq gene; (3) a substitution of one or more nucleotides of an Oncoseq gene, (4) a chromosomal rearrangement of an Oncoseq gene; (5) an alteration in the level of a messenger RNA transcript of an Oncoseq gene, (6) aberrant modification of an Oncoseq gene, such as of the methylation pattern of the genomic DNA, (7) the presence of a non-wild type splicing pattern of a messenger RNA transcript of an Oncoseq gene, (8) a non-wild type level of a protein, (9) allelic loss of an Oncoseq gene, and (10) inappropriate post-translational modification of an Oncoseq protein. As described herein, there are a large number of assay techniques known in the art which can be used for detecting lesions in an Oncoseq gene. A preferred biological sample is a peripheral blood leukocyte sample isolated by conventional means from a subject. However, any biological sample containing nucleated cells may be used, including, for example, buccal mucosal cells.

In certain embodiments, detection of the lesion involves the use of a probe/primer in a polymerase chain reaction (PCR) (see, e.g., U.S. Pat. Nos. 4,683,195 and 4,683,202), such as anchor PCR or RACE PCR, or, alternatively, in a ligation chain reaction (LCR) (see, e.g., Landegran el al. (1988) *Science* 241:1077-1080; and Nakazawa et al. (1994) *Proc. Natl. Acad. Sci. USA* 91:360-364), the latter of which can be particularly useful for detecting point mutations in the Oncoseq gene (see Abravaya et al. (1995) *Nucl Acids Res* 23:675-682). This method can include the steps of collecting a sample of cells from a patient, isolating nucleic acid (e.g., genomic, mRNA or both) from the cells of the sample, contacting the nucleic acid sample with one or more primers that specifically hybridize to an Oncoseq gene under conditions such that hybridization and expansion of the Oncoseq gene (if present) occurs, and detecting the presence or absence of an expansion product, or detecting the size of the expansion product and comparing the length to a control sample. It is anticipated that PCR and/or LCR may be desirable to use as a preliminary amplification step in conjunction with any of the techniques used for detecting mutations described herein.

Alternative expansion methods include: self sustained sequence replication (Guatelli et al., 1990, *Proc Natl Acad Sci USA* 87:1874-1878), transcriptional amplification system Kwoh, et al., 1989, *Proc Natl Acad Sci USA* 86:1173-1177), Q-Beta Replicase (Lizardi et al, 1988, *BioTechnology* 6:1197), or any other nucleic acid amplification method, followed by the detection of the amplified molecules using techniques well known to those of skill in the art. These detection schemes are especially useful for the detection of nucleic acid molecules if such molecules are present in very low numbers.

In an alternative embodiment, mutations in an Oncoseq gene from a sample cell can be identified by alterations in restriction enzyme cleavage patterns. For example, sample and control DNA is isolated, amplified (optionally), digested with one or more restriction endonucleases, and fragment length sizes are determined by gel electrophoresis and compared. Differences in fragment length sizes between sample and control DNA indicates mutations in the sample DNA. Moreover, the use of sequence specific ribozymes (see, for example, U.S. Pat. No. 5,493,531) can be used to score for the presence of specific mutations by development or loss of a ribozyme cleavage site.

In other embodiments, genetic mutations in an Oncoseq sequence of the invention can be identified by hybridizing a sample and control nucleic acids, e.g., DNA or RNA, to high density arrays containing hundreds or thousands of oligonucleotides probes (Cronin et al. (1996) *Human Mutation* 7: 244-255; Kozal et al. (1996) *Nature Medicine* 2: 753-759). For example, genetic mutations in an Oncoseq sequence of the invention can be identified in two dimensional arrays containing light-generated DNA probes as described in Cronin et al. above. Briefly, a first hybridization array of probes can be used to scan through long stretches of DNA in a sample and control to identify base changes between the sequences by making linear arrays of sequential overlapping probes. This step allows the identification of point mutations. This step is followed by a second hybridization array that allows the characterization of specific mutations by using smaller, specialized probe arrays complementary to all variants or mutations detected. Each mutation array is composed of parallel probe sets, one complementary to the wild-type gene and the other complementary to the mutant gene.

In yet another embodiment, any of a variety of sequencing reactions known in the art can be used to directly sequence the Oncoseq gene and detect mutations by comparing the sequence of the sample Oncoseq sequence with the corresponding wild-type (control) sequence. Examples of sequencing reactions include those based on techniques developed by Maxim and Gilbert (1977) *Proc. Natl. Acad Sci. USA* 74:560 or Sanger (1977) *Proc. Natl. Acad. Sci USA* 74:5463. It is also contemplated that any of a variety of automated sequencing procedures can be utilized when performing the diagnostic assays (Naeve et al., (1995) *Biotechniques* 19:448), including sequencing by mass spectrometry (see, e.g., PCT International Publ. No. WO 94/16101; Cohen et al. (1996) *Adv Chromatogr* 36:127-162; and Griffin et al. (1993) *Appl Biochem Biotechnol* 38:147-159).

Other methods for detecting mutations in the Oncoseq gene include methods in which protection from cleavage agents is used to detect mismatched bases in RNA/RNA or RNA/DNA heteroduplexes (Myers et al. (1985) *Science* 230:1242). In general, the art technique of "mismatch cleavage" starts by providing heteroduplexes of formed by hybridizing (labeled) RNA or DNA containing the wild-type Oncoseq sequence sequence with potentially mutant RNA or DNA obtained from a tissue sample. The double-stranded duplexes are treated with an agent that cleaves single-stranded regions of the duplex such as which will exist due to basepair mismatches between the control and sample strands. For instance, RNA/DNA duplexes can be treated with RNase and DNA/DNA hybrids treated with S1 nuclease to enzymatically digesting the mismatched regions. In other embodiments, either DNA/DNA or RNA/DNA duplexes can be treated with hydroxylamine or osmium tetroxide and with piperidine in order to digest mismatched regions. After digestion of the mismatched regions, the resulting material is then separated by size on denaturing polyacrylamide gels to determine the site of mutation. See, for example, Cotton et al (1988) *Proc Natl Acad Sci USA* 85:4397; Saleeba et al (1992) *Methods Enzymol* 217:286-295. In an embodiment, the control DNA or RNA can be labeled for detection.

In still another embodiment, the mismatch cleavage reaction employs one or more proteins that recognize mismatched base pairs in double-stranded DNA (so called "DNA mismatch repair" enzymes) in defined systems for detecting and mapping point mutations in Oncoseq cDNAs obtained from samples of cells. For example, the mutY enzyme of *E. coli* cleaves A at G/A mismatches and the thymidine DNA glycosylase from HeLa cells cleaves T at G/T mismatches (Hsu et al. (1994) *Carcinogenesis* 15:1657-1662). According to an exemplary embodiment, a probe based on an Oncoseq sequence, e.g., a wild-type Oncoseq sequence, is hybridized to a cDNA or other DNA product from a test cell(s). The duplex is treated with a DNA mismatch repair enzyme, and the cleavage products, if any, can be detected from electrophoresis protocols or the like. See, for example, U.S. Pat. No. 5,459,039.

In other embodiments, alterations in electrophoretic mobility will be used to identify mutations in Oncoseq genes. For example, single strand conformation polymorphism (SSCP) may be used to detect differences in electrophoretic mobility between mutant and wild type nucleic acids (Orita et al. (1989) *Proc Natl Acad Sci USA:* 86:2766, see also Cotton (1993) *Mutat Res* 285:125-144; Hayashi (1992) *Genet Anal Tech Appl* 9:73-79). Single-stranded DNA fragments of sample and control an Oncoseq nucleic acids will be denatured and allowed to renature. The secondary structure of single-stranded nucleic acids varies according to sequence, the resulting alteration in electrophoretic mobility enables the detection of even a single base change. The DNA fragments may be labeled or detected with labeled probes. The sensitivity of the assay may be enhanced by using RNA, rather than DNA, in which the secondary structure is more sensitive to a change in sequence. In one embodiment, the subject method utilizes heteroduplex analysis to separate double stranded heteroduplex molecules on the basis of changes in electrophoretic mobility. See, e.g., Keen et al. (1991) *Trends Genet* 7:5.

In yet another embodiment the movement of mutant or wild-type fragments in polyacrylamide gels containing a gradient of denaturant is assayed using denaturing gradient gel electrophoresis (DGGE). See, e.g., Myers et al (1985) *Nature* 313:495. When DGGE is used as the method of analysis, DNA will be modified to insure that it does not completely denature, for example by adding a GC clamp of approximately 40 bp of high-melting GC-rich DNA by PCR. In a further embodiment, a temperature gradient is used in place of a denaturing gradient to identify differences in the mobility of control and sample DNA. See, e.g., Rosenbaum and Reissner (1987) *Biophys Chem* 265:12753.

Examples of other techniques for detecting point mutations include, but are not limited to, selective oligonucleotide hybridization, selective amplification, or selective primer extension. For example, oligonucleotide primers may be prepared in which the known mutation is placed centrally and then hybridized to target DNA under conditions that permit hybridization only if a perfect match is found. See, e.g., Saiki et al. (1986) *Nature* 324:163); Saiki et al. (1989) *Proc Natl Acad. Sci USA* 86:6230. Such allele specific oligonucleotides are hybridized to PCR amplified target DNA or a number of different mutations when the oligonucleotides are attached to the hybridizing membrane and hybridized with labeled target DNA.

Alternatively, allele specific amplification technology that depends on selective PCR expansion may be used in conjunction with the instant invention. Oligonucleotides used as primers for specific amplification may carry the mutation of interest in the center of the molecule (so that amplification depends on differential hybridization) (Gibbs et al. (1989) *Nucleic Acids Res* 17:2437-2448) or at the extreme 3' end of one primer where, under appropriate conditions, mismatch can prevent, or reduce polymerase extension (Prossner (1993) *Tibtech* 11:238). In addition it may be desirable to introduce a novel restriction site in the region of the mutation to create cleavage-based detection. See, e.g., Gasparini et al (1992) *Mol Cell Probes* 6:1. It is anticipated that in certain embodiments amplification may also be performed using Taq ligase for amplification. See, e.g., Barany (1991) *Proc Natl Acad Sci USA* 88:189. In such cases, ligation will occur only if there is a perfect match at the 3' end of the 5' sequence, making it possible to detect the presence of a known mutation at a specific site by looking for the presence or absence of amplification.

The methods described herein may be performed, for example, by utilizing pre-packaged diagnostic kits comprising at least one probe nucleic acid or antibody reagent described herein, which may be conveniently used, e.g., in clinical settings to diagnose patients exhibiting symptoms or family history of a disease or illness involving an Oncoseq gene.

Furthermore, any cell type or tissue, preferably peripheral blood leukocytes, in which an Oncoseq of the invention is expressed may be utilized in the prognostic assays described herein. However, any biological sample containing nucleated cells may be used, including, for example, buccal mucosal cells.

Pharmacogenomics

Agents, or modulators that have a stimulatory or inhibitory effect on Oncoseq activity (e.g., Oncoseq gene expression), as identified by a screening assay described herein can be administered to individuals to treat (prophylactically or therapeutically) disorders (e.g., neurological, cancer-related or gestational disorders) associated with aberrant Oncoseq activity. In conjunction with such treatment, the pharmacogenomics (i.e., the study of the relationship between an individual's genotype and that individual's response to a foreign compound or drug) of the individual may be considered. Differences in metabolism of therapeutics can lead to severe toxicity or therapeutic failure by altering the relation between dose and blood concentration of the pharmacologically active drug. Thus, the pharmacogenomics of the individual permits the selection of effective agents (e.g., drugs) for prophylactic or therapeutic treatments based on a consideration of the individual's genotype. Such pharmacogenomics can further be used to determine appropriate dosages and therapeutic regimens. Accordingly, the activity of an Oncoseq protein, expression of an Oncoseq nucleic acid, or mutation content of an Oncoseq genes in an individual can be determined to thereby select appropriate agent(s) for therapeutic or prophylactic treatment of the individual.

Pharmacogenomics deals with clinically significant hereditary variations in the response to drugs due to altered drug disposition and abnormal action in affected persons. See e.g., Eichelbaum (1996) Clin Exp Pharmacol Physiol, 23:983-985 and Linder (1997) Clin Chem, 43:254-266. In general, two types of pharmacogenetic conditions can be differentiated. Genetic conditions transmitted as a single factor altering the way drugs act on the body (altered drug action) or genetic conditions transmitted as single factors altering the way the body acts on drugs (altered drug metabolism). These pharmacogenetic conditions can occur either as rare defects or as polymorphisms. For example, glucose-6-phosphate dehydrogenase (G6PD) deficiency is a common inherited enzymopathy in which the main clinical complication is haemolysis after ingestion of oxidant drugs (anti-malarials, sulfonamides, analgesics, nitrofurans) and consumption of fava beans.

As an illustrative embodiment, the activity of drug metabolizing enzymes is a major determinant of both the intensity and duration of drug action. The discovery of genetic polymorphisms of drug metabolizing enzymes (e.g., N-acetyltransferase 2 (NAT 2) and cytochrome P450 enzymes CYP2D6 and CYP2C19) has provided an explanation as to why some patients do not obtain the expected drug effects or show exaggerated drug response and serious toxicity after taking the standard and safe dose of a drug. These polymorphisms are expressed in two phenotypes in the population, the extensive metabolizer (EM) and poor metabolizer (PM). The prevalence of PM is different among different populations. For example, the gene coding for CYP2D6 is highly polymorphic and several mutations have been identified in PM, which all lead to the absence of functional CYP2D6. Poor metabolizers of CYP2D6 and CYP2C19 quite frequently experience exaggerated drug response and side effects when they receive standard doses. If a metabolite is the active therapeutic moiety, PM show no therapeutic response, as demonstrated for the analgesic effect of codeine mediated by its CYP2D6-formed metabolite morphine. The other extreme are the so called ultra-rapid metabolizers who do not respond to standard doses.

Recently, the molecular basis of ultra-rapid metabolism has been identified to be due to CYP2D6 gene amplification.

Thus, the activity of an Oncoseq protein, expression of an Oncoseq nucleic acid, or mutation content of an Oncoseq genes in an individual can be determined to thereby select appropriate agent(s) for therapeutic or prophylactic treatment of the individual. In addition, pharmacogenetic studies can be used to apply genotyping of polymorphic alleles encoding drug-metabolizing enzymes to the identification of an individual's drug responsiveness phenotype. This knowledge, when applied to dosing or drug selection, can avoid adverse reactions or therapeutic failure and thus enhance therapeutic or prophylactic efficiency when treating a subject with an Oncoseq modulator, such as a modulator identified by one of the exemplary screening assays described herein.

Monitoring Clinical Efficacy

Monitoring the influence of agents (e.g., drugs, compounds) on the expression or activity of an Oncoseq (e.g., the ability to modulate aberrant cell proliferation and/or differentiation) can be applied in basic drug screening and in clinical trials. For example, the effectiveness of an agent determined by a screening assay as described herein to increase Oncoseq gene expression, protein levels, or upregulate Oncoseq activity, can be monitored in clinical trials of subjects exhibiting decreased Oncoseq gene expression, protein levels, or downregulated Oncoseq activity. Alternatively, the effectiveness of an agent determined by a screening assay to decrease Oncoseq gene expression, protein levels, or downregulate Oncoseq activity, can be monitored in clinical trials of subjects exhibiting increased Oncoseq gene expression, protein levels, or upregulated Oncoseq activity. In such clinical trials, the expression or activity of an Oncoseq and, preferably, other genes that have been implicated in, for example, a proliferative or neurological disorder, can be used as a "read out" or marker of the responsiveness of a particular cell.

For example, genes, including genes encoding an Oncoseq protein of the invention, that are modulated in cells by treatment with an agent (e.g., compound, drug or small molecule) that modulates an Oncoseq activity (e.g., identified in a screening assay as described herein) can be identified. Thus, to study the effect of agents on cellular proliferation disorders, for example, in a clinical trial, cells can be isolated and RNA prepared and analyzed for the levels of expression of an Oncoseq and other genes implicated in the disorder. The levels of gene expression (i.e., a gene expression pattern) can be quantified by Northern blot analysis or RT-PCR, as described herein, or alternatively by measuring the amount of protein produced, by one of the methods as described herein, or by measuring the levels of activity of an Oncoseq or other genes. In this way, the gene expression pattern can serve as a marker, indicative of the physiological response of the cells to the agent. Accordingly, this response state may be determined before, and at various points during, treatment of the individual with the agent.

In one embodiment, the invention provides a method for monitoring the effectiveness of treatment of a subject with an agent (e.g., an agonist, antagonist, protein, peptide, nucleic acid, peptidomimetic, small molecule, or other drug candidate identified by the screening assays described herein) comprising the steps of (i) obtaining a pre-administration sample from a subject prior to administration of the agent; (ii) detecting the level of expression of an Oncoseq protein, mRNA, or genomic DNA in the preadministration sample; (iii) obtaining one or more post-administration samples from the subject; (iv) detecting the level of expression or activity of the Oncoseq protein, mRNA, or genomic DNA in the post-administration samples; (v) comparing the level of expression or activity of the Oncoseq protein, mRNA, or genomic DNA in the pre-administration sample with the Oncoseq protein, mRNA, or genomic DNA in the post administration sample or samples; and (vi) altering the administration of the agent to the subject accordingly. For example, increased administration of the agent may be desirable to increase the expression or activity of an Oncoseq to higher levels than detected, i.e., to increase the effectiveness of the agent. Alternatively, decreased administration of the agent may be desirable to decrease expression or activity of an Oncoseq to lower levels than detected, i.e., to decrease the effectiveness of the agent.

Methods of Treatment

The present invention provides for both prophylactic and therapeutic methods of treating a subject at risk of (or susceptible to) a disorder or having a disorder associated with aberrant Oncoseq expression or activity.

Diseases and disorders that are characterized by increased (relative to a subject not suffering from the disease or disorder) levels or biological activity may be treated with Therapeutics that antagonize (i.e., reduce or inhibit) activity. Therapeutics that antagonize activity may be administered in a therapeutic or prophylactic manner. Therapeutics that may be utilized include, but are not limited to, (i) an Oncoseq polypeptide, or analogs, derivatives, fragments or homologs thereof; (ii) antibodies to an Oncoseq peptide; (iii) nucleic acids encoding an Oncoseq peptide; (iv) administration of antisense nucleic acid and nucleic acids that are "dysfunctional" (i.e., due to a heterologous insertion within the coding sequences of coding sequences to an Oncoseq peptide) that are utilized to "knockout" endogenous function of an Oncoseq peptide by homologous recombination (see, e.g., Capecchi, 1989, *Science* 244: 1288-1292); or (v) modulators (i.e., inhibitors, agonists and antagonists, including additional peptide mimetic of the invention or antibodies specific to a peptide of the invention) that alter the interaction between an Oncoseq peptide and its binding partner.

Diseases and disorders that are characterized by decreased (relative to a subject not suffering from the disease or disorder) levels or biological activity may be treated with Therapeutics that increase (i.e., are agonists to) activity. Therapeutics that upregulate activity may be administered in a therapeutic or prophylactic manner. Therapeutics that may be utilized include, but are not limited to, an Oncoseq peptide, or analogs, derivatives, fragments or homologs thereof; or an agonist that increases bioavailability.

Increased or decreased levels can be readily detected by quantifying peptide and/or RNA, by obtaining a patient tissue sample (e.g., from biopsy tissue) and assaying it in vitro for RNA or peptide levels, structure and/or activity of the expressed peptides (or mRNAs of an Oncoseq peptide). Methods that are well-known within the art include, but are not limited to, immunoassays (e.g. by Western blot analysis, immunoprecipitation followed by sodium dodecyl sulfate (SDS) polyacrylamide gel electrophoresis, immunocytochemistry, etc.) and/or hybridization assays to detect expression of mRNAs (e.g., Northern assays, dot blots, in situ hybridization, etc.).

In one aspect, the invention provides a method for preventing, in a subject, a disease or condition associated with aberrant Oncoseq expression or activity, by administering to the subject an agent that modulates Oncoseq expression or at least one Oncoseq activity. Subjects at risk for a disease that is caused or contributed to by aberrant Oncoseq expression or activity can be identified by, for example, any or a combination of diagnostic or prognostic assays as described herein. Administration of a prophylactic agent can occur prior to the manifestation of symptoms characteristic of the Oncoseq aberrancy, such that a disease or disorder is prevented or, alternatively, delayed in its progression. Depending on the type of an Oncoseq aberrancy, for example, an Oncoseq agonist or Oncoseq antagonist agent can be used for treating the subject. The appropriate agent can be determined based on screening assays described herein.

Another aspect of the invention pertains to methods of modulating Oncoseq expression or activity for therapeutic purposes. The modulatory method of the invention involves contacting a cell with an agent that modulates one or more of the activities of an Oncoseq protein activity associated with the cell. An agent that modulates an Oncoseq protein activity can be an agent as described herein, such as a nucleic acid or a protein, a naturally-occurring cognate ligand of an Oncoseq protein, a peptide, an Oncoseq peptidomimetic, or other small molecule. In one embodiment, the agent stimulates one or more an Oncoseq protein activity. Examples of such stimulatory agents include active an Oncoseq protein and a nucleic acid molecule encoding an Oncoseq protein that has been introduced into the cell. In another embodiment, the agent inhibits one or more an Oncoseq protein activity. Examples of such inhibitory agents include antisense an Oncoseq nucleic acid molecules and anti-Oncoseq protein antibodies. These modulatory methods can be performed in vitro (e.g., by culturing the cell with the agent) or, alternatively, in vivo (e.g., by administering the agent to a subject). As such, the present invention provides methods of treating an individual afflicted with a disease or disorder characterized by aberrant expression or activity of an Oncoseq protein or nucleic acid molecule. In one embodiment, the method involves administering an agent (e.g., an agent identified by a screening assay described herein), or combination of agents that modulates (e.g., upregulates or downregulates) Oncoseq expression or activity. In another embodiment, the method involves administering an Oncoseq protein or nucleic acid molecule as therapy to compensate for reduced or aberrant Oncoseq expression or activity.

Determination of the Biological Effect of a Therapeutic

In various embodiments of the present invention, suitable in vitro or in vivo assays are utilized to determine the effect of a specific Therapeutic and whether its administration is indicated for treatment of the affected tissue.

In various specific embodiments, in vitro assays may be performed with representative cells of the type(s) involved in the patient's disorder, to determine if a given Therapeutic exerts the desired effect upon the cell type(s). Compounds for use in therapy may be tested in suitable animal model systems including, but not limited to rats, mice, chicken, cows, monkeys, rabbits, and the like, prior to testing in human subjects. Similarly, for in vivo testing, any of the animal model system known in the art may be used prior to administration to human subjects.

Malignancies

Some Oncoseq polypeptides are expressed in cancerous cells. Accordingly, the corresponding Oncoseq protein is involved in the regulation of cell proliferation. Accordingly, Therapeutics of the present invention may be useful in the therapeutic or prophylactic treatment of diseases or disorders that are associated with cell hyperproliferation and/or loss of control of cell proliferation (e.g., cancers, malignancies and tumors). For a review of such hyperproliferation disorders, see e.g., Fishman, et al., 1985. MEDICINE, 2nd ed., J. B. Lippincott Co., Philadelphia, Pa.

Therapeutics of the present invention may be assayed by any method known within the art for efficacy in treating or preventing malignancies and related disorders. Such assays include, but are not limited to, in vitro assays utilizing transformed cells or cells derived from the patient's tumor, as well as in vivo assays using animal models of cancer or malignancies. Potentially effective Therapeutics are those that, for example, inhibit the proliferation of tumor-derived or transformed cells in culture or cause a regression of tumors in animal models, in comparison to the controls.

In the practice of the present invention, once a malignancy or cancer has been shown to be amenable to treatment by modulating (i.e., inhibiting, antagonizing or agonizing) activity, that cancer or malignancy may subsequently be treated or prevented by the administration of a Therapeutic that serves to modulate protein function.

Premalignant Conditions

The Therapeutics of the present invention that are effective in the therapeutic or prophylactic treatment of cancer or malignancies may also be administered for the treatment of pre-malignant conditions and/or to prevent the progression of a pre-malignancy to a neoplastic or malignant state. Such prophylactic or therapeutic use is indicated in conditions known or suspected of preceding progression to neoplasia or cancer, in particular, where non-neoplastic cell growth consisting of hyperplasia, metaplasia or, most particularly, dysplasia has occurred. For a review of such abnormal cell growth see e.g., Robbins & Angell, 1976. BASIC PATHOLOGY, 2nd ed., W. B. Saunders Co., Philadelphia, Pa.

Hyperplasia is a form of controlled cell proliferation involving an increase in cell number in a tissue or organ, without significant alteration in its structure or function. For example, it has been demonstrated that endometrial hyperplasia often precedes endometrial cancer. Metaplasia is a form of controlled cell growth in which one type of mature or fully differentiated cell substitutes for another type of mature cell. Metaplasia may occur in epithelial or connective tissue cells. Dysplasia is generally considered a precursor of cancer, and is found mainly in the epithelia. Dysplasia is the most disorderly form of non-neoplastic cell growth, and involves a loss in individual cell uniformity and in the architectural orientation of cells. Dysplasia characteristically occurs where there exists chronic irritation or inflammation, and is often found in the cervix, respiratory passages, oral cavity, and gall bladder.

Alternatively, or in addition to the presence of abnormal cell growth characterized as hyperplasia, metaplasia, or dysplasia, the presence of one or more characteristics of a transformed or malignant phenotype displayed either in vivo or in vitro within a cell sample derived from a patient, is indicative of the desirability of prophylactic/therapeutic administration of a Therapeutic that possesses the ability to modulate activity of An aforementioned protein. Characteristics of a transformed phenotype include, but are not limited to: (i) morphological changes; (ii) looser substratum attachment; (iii) loss of cell-to-cell contact inhibition; (iv) loss of anchorage dependence; (v) protease release; (vi) increased sugar transport; (vii) decreased serum requirement; (viii) expression of fetal antigens, (ix) disappearance of the 250 kDa cell-surface protein, and the like. See e.g., Richards, el al., 1986. MOLECULAR PATHOLOGY, W.B. Saunders Co., Philadelphia, Pa.

In a specific embodiment of the present invention, a patient that exhibits one or more of the following predisposing factors for malignancy is treated by administration of an effective amount of a Therapeutic: (i) a chromosomal translocation associated with a malignancy (e.g., the Philadelphia chromosome (bcr/abl) for chronic myelogenous leukemia and t(14;20) for follicular lymphoma, etc.); (ii) familial polyposis or Gardner's syndrome (possible forerunners of colon cancer); (iii) monoclonal gammopathy of undetermined significance (a possible precursor of multiple myeloma) and (iv) a first degree kinship with persons having a cancer or pre-cancerous disease showing a Mendelian (genetic) inheritance pattern (e.g., familial polyposis of the colon, Gardner's syndrome, hereditary exostosis, polyendocrine adenomatosis, Peutz-Jeghers syndrome, neurofibromatosis of Von Recklinghausen, medullary thyroid carcinoma with amyloid production and pheochromocytoma, retinoblastoma, carotid body tumor, cutaneous melanocarcinoma, intraocular melanocarcinoma, xeroderma pigmentosum, ataxia telangiectasia, Chediak-Higashi syndrome, albinism, Fanconi's aplastic anemia and Bloom's syndrome).

In another embodiment, a Therapeutic of the present invention is administered to a human patient to prevent the progression to breast, colon, lung, pancreatic, or uterine cancer, or melanoma or sarcoma.

Hyperproliferative and Dysproliferative Disorders

In one embodiment of the present invention, a Therapeutic is administered in the therapeutic or prophylactic treatment of hyperproliferative or benign dysproliferative disorders. The efficacy in treating or preventing hyperproliferative diseases or disorders of a Therapeutic of the present invention may be assayed by any method known within the art. Such assays include in vitro cell proliferation assays, in vitro or in vivo assays using animal models of hyperproliferative diseases or disorders, or the like. Potentially effective Therapeutics may, for example, promote cell proliferation in culture or cause growth or cell proliferation in animal models in comparison to controls.

Specific embodiments of the present invention are directed to the treatment or prevention of cirrhosis of the liver (a condition in which scarring has overtaken normal liver regeneration processes); treatment of keloid (hypertrophic scar) formation causing disfiguring of the skin in which the scarring process interferes with normal renewal; psoriasis (a common skin condition characterized by excessive proliferation of the skin and delay in proper cell fate determination); benign tumors; fibrocystic conditions and tissue hypertrophy (e.g., benign prostatic hypertrophy).

EXAMPLES

A. Methods and Materials Employed in the Examples

Cell lines and tumor tissues. Eleven human cell lines derived from head and neck squamous cell carcinomas (584, MDA686, MDA886, MSK921, MSK922, MDA1186, MDA1386, 1483, MDA1586, MDA1986, and MSKQLL2) and one cell line derived from premalignant oral epithelium (MSK Leuk1) were used in the present study. Of these cell lines, MSK921, MSK922, MSKQLL2, and MSK Leuk1 were established at Memorial Sloan-Kettering Cancer Center; MDA686, MDA886, MDA1186, MDA1386, MDA1586, and MDA1986 were established at The University of Texas M. D. Anderson Cancer Center (Houston, Tex.); and 584 and 1483 were established at Wadsworth Laboratories, New York State Department of Health (Albany, N.Y.). (See Singh, B. et al. (2001) *Cancer Res* 61, 4506-13).

Cell lines derived from lung carcinomas, 3T3 cells, and HeLa cells were purchased from the American Type Culture Collection. Primary tumors from head and neck and lung cancers were collected from patients undergoing surgical resection of their tumor, after obtaining informed consent and following institutional guidelines. Human adult multi-tissue Northern blot (Clontech, Palo Alto, Calif.) and fetal and adult cDNA were obtained from a commercial source (Promega Corp., Madison, Wis.)

cDNA cloning, expression construct and transfection. The human Oncoseq cDNA was generated by reverse transcription (RT)-PCR of total RNA isolated from head and neck cancer cell line MDA886 using sequential 5' primers

```
P1:  5'-TGGGGGAAAGAATGGATGAAC-3',     (SEQ ID NO:5)

P2:  5'-CTTGGTACAGCGCTGGGCGCT-3,      (SEQ ID NO:6)

and

P3:  5'-CTGGAGGACACCAACATGAA-3'       (SEQ ID NO:7)
at
the
5'
end;
and

P4:  5'-CCAGCCAGCAGAAATTGACT-3'       (SEQ ID NO:8)
at
the
3'
end
to
iden-
tify
the
full
length
cDNA.
```

PCR using primers P3 and P4 resulted in a product of 876 bp. The PCR products were isolated and sequenced using the ABI PRISM dye terminator cycle sequencing ready reaction kit (PerkinElmer Life Sciences, Inc. Boston, Mass.) on an Applied Biosystems Model 377 (Applied Biosystems, Foster City, Calif.) automated DNA sequencer, according to the manufacturers' protocols. The full length Oncoseq cDNA was cloned into pGEM-T vector (Promega) according to the manufacturer's protocol. Oncoseq expression constructs were developed by ligation of the cDNA (876 bp) into the NotI sites of the mammalian expression vector pUSEamp (Upstate Group, Inc., Waltham, Mass.) or pIRES-FHneo (a gift from Dr. Brian Chait). An antisense nucleic acid to Oncoseq was generated by ligation of the full length Oncoseq in the 3' to 5' orientation (designated pUSEamp-asOncoseq). Stable transfection of Oncoseq in the Tet-Off™ NIH-3T3 Cell Line (now replaced by MEF/3T3 Tet-Off; BD Biosciences Clontech) system was established according to the manufacturer's protocols, allowing Oncoseq expression to be under the control of a tetracycline repressible promoter. Restriction mapping and direct sequencing were used to confirm sense-oriented and antisense-oriented constructs prior to use in transfection experiments. pUSEamp-Oncoseq, pUSEamp-asOncoseq, pIRES-FHneo-Oncoseq or vector alone were transfected by lipofection using the LipofectAMINE PLUS™ Reagents (Invitrogen Corp., Carlsbad, Calif.) according to manufacturer's protocol. For stable transfection, clones were isolated under geneticin (G-418 Sulfate; 600 µg/ml; Invitrogen) selection.

5' Rapid amplification of cDNA ends (RACE). The sequence of the 5'-end of cDNA was derived using the SMART RACE cDNA Amplification kit (Clontech) according to the manufacturer's protocols. cDNAs were generated by RT-PCR from human squamous cell carcinoma (MDA886) total RNA. The oligonucleotide primers used for 5' RACE, which were designed based on the sequence of Oncoseq (AF 456425 SEQ ID NO:1), included R-1: 5'-CATGCAATAATCAACACACTAATGCTG (SEQ ID NO:9) for the first PCR amplification, NR-1: 5'-ATCGAGTGCCAGGTCATCACAGA (SEQ ID NO:10) for nested PCR, and R-2: 5'-TAC ACT CTC TCG TAT ATA AAG TTC AGG (SEQ ID NO:11) for sequencing the nested PCR product.

In vitro transcription and translation. Oncoseq cDNA cloned into the plasmid pGEM-T (Promega) was transcribed in vitro, and the transcripts were translated using the TnT T7 Quick Coupled Transcription/Translation System (Promega) in the presence of $^{35}$S-methionine. The translation products were separated using 4-15% SDS-PAGE, and visualized by autoradiography.

Cell growth and colony formation assays. The 3-(4,5-dimethylthiazol-2-yl)-2,5-diphenyl-tetrazolium bromide (MTT)-based calorimetric assay (Sigma Chemical Co., St. Louis, Mo.) was performed as described by Singh et al. ((2002) Genes Dev 16:984-93).

For anchorage-independent proliferation, 4 ml agar (1%) in DMEM was supplemented with 10% fetal calf serum (FCS) and poured into a 60-mm dish to form bottom agar. 1 ml Agar mix (0.7%) was layered with 2,000 cells on top, and the dishes were incubated at 37° C. in a 5% $CO_2$ atmosphere. 0.3 ml Fresh top agar was added each week. After 3 weeks, the plates were stained with crystal violet (Sigma Chemical Co.) for one hour, destained and the colonies were counted under a dissecting microscope.

Soft agar forced suspension culture assay was performed on HaCaT cells, an immortal human skin keratinocyte cell line (Boukamp P. et al. (1988). *J. Cell Biol.* 106, 761-771). The cells were transiently transfected with either pUSEamp-Oncoseq or pUSEamp vector without any insert (Upstate Group, Inc). They were plated on 0.9% agarose coated plates and incubated in DMEM medium with 250 µg/ml neomycin for 1 week (see Mahoney, M G et al. (2002) Oncogene 21, 2161-70). The cells were fixed with 70% ethanol, stained with crystal violet and counted under microscope magnification.

Flow cytometry and FACS analysis. NIH 3T3 cells transfected with either pUSEamp or pUSEamp-Oncoseq plasmids, were synchronized by serum starvation, collected by trypsinization, and re-suspended in PBS and 2 mM EDTA. The cells were then fixed in 70% ethanol, digested with RNase A (0.02 µg/µl), stained with 50 µg/ml ethidium bromide, and analyzed using Becton-Dickinson FacsScan flow cytometer (Becton Dickinson, San José, Calif., USA) and CellQuest™ software.

Assessment of apoptosis. The effect of an antisense sequence to Oncoseq on cells was determined as follows. $1 \times 10^4$ Cells were grown in a 1 well slide chamber (Lab-Tek, Nalge Nunc) and treated with 2 µg of pUSEamp-as-Oncoseq or empty pUSEamp vector. Cells were collected and spotted onto a slide 24 hours post transfection. The slides were air-dried and fixed in 4% paraformaldehyde for 12 minutes. After two PBS washes, the cells were stained with 10 ug/ml of Hoechst 33342 for 10 minutes. The slides were washed twice in PBS and mounted. The slides were assessed for changes in nuclear morphology typical of apoptosis (nuclear shrinkage, condensation, and fragmentation) under a Zeiss fluorescence microscope with appropriate filter combination (DAPI filter). The extent of apoptosis was quantified by the Cellular DNA Fragmentation ELISA (Roche Diagnostics Corp., Indianapolis, Ind.) according to manufacturer's protocols.

In vitro migration and invasion. The migratory potential and invasive capacity of cultured cells was assayed by a modified Boyden chamber method. (see O-charoenrat, P. et at. (2000) *Cancer Res* 60, 1121-8). A growth factor-reduced Matrigel matrix (Becton Dickinson, Bedford, Mass.) is diluted 1:25 with ice-cold PBS. Matrigel is dispensed into 24-well cell culture inserts containing PET membranes (6.4 mm in diameter with 8-um pore; FALCON, BD Biosciences, Bedford Mass.), incubated at 37° C. for 3 h and left to dry at room temperature overnight. The Matrigel is re-hydrated with 250 ml of pre-warmed DMEM/0.1% BSA for 2 hours at room temperature with occasional agitation. Cells to be applied to the upper chamber are harvested in exponential growth with PBS containing 1 mM EDTA, washed with serum-free DMEM and re-suspended in DMEM/0.1% BSA at $4\times10^5$ cells/ml. The lower chamber was filled with 750 ul of DMEM/O. 1% BSA containing 25 g/ml of fibronectin or DMEM/5% FCS as a chemo-attractant, and 250 ul ($1\times10^5$ cells) of cell suspension were added to each insert. The plates of inserts were incubated for 36 h at 37° C. Non-coated membrane inserts were seeded to serve as migration controls in the invasion assay. Following incubation, non-invasive cells were removed from the upper surface of the membrane by gentle scrubbing with a cotton tipped swab. The membranes were fixed with 0.25% (v/v) glutaraldehyde in PBS for 30 min and stained with hematoxylin. The cells that had migrated to the lower surface were counted under a microscope at 100× magnification in 10 fields.

Athymic mouse tumorigenicity. $5\times10^5$ NIH 3T3 cells transfected with either pUSEamp-Oncoseq or pUSEamp plasmids, in log phase growth, were injected subcutaneously into each flank of BALB/C athymic nude mice (National Cancer Institute, Bethesda, Md.); four animals were used per subclone. The health of the animals and the size of tumors was monitored daily and tumor latency (time of appearance) and size ($mm^3$) was recorded. The mice were sacrificed eight weeks after injection, and the expression of Oncoseq was confirmed in all tumors that developed by real time PCR. Autopsy studies were performed on all animals including whole organ evaluation of liver, spleen, lung and axillary and inguinal lymph nodal tissues. All animal experiments were performed following institutional guidelines.

Fluorescent in situ hybridization (FISH). Dual color FISH was performed as described using DNA from BAC clone 202B22 and chromosome 3 centromeric probes. (Singh et al. (2001)).

Southern and Northern blot analysis Probes for southern and northern blot analysis were prepared by PCR expansion using the following primers:

```
Onco-    5'-CTGGAGGACACCAACATGAA-3'    (SEQ ID NO:12)
seq1:

and

Onco-    5'-CCAGCCAGCAGAAATTGACT-3';   (SEQ ID NO:13)
seq2:

β-       5'-TGGGACGACATGGAGAAAATC-3'   (SEQ ID NO:14)
actin1:

and

β-       5'-AGGGAGGAGCTGGAAGCAGC.      (SEQ ID NO:15)
actin2:
```

Southern blot analysis was performed according to standard protocol (Singh, B. et al. (2002)).

Western Blot analysis. A novel rabbit polyclonal antibody against Oncoseq protein (Antibody 1B-D125/I140-DDM-SNYDEEGAWPVLI) was developed and affinity purified by Bethyl Laboratories (Montgomery, Tex.). The peptide given by the sequence DDMSNYDEEGAWPVLI occurs from residue 225 to residue 240 of SEQ ID NO:2 or SEQ ID NO:4. The targeted amino acid sequence is identical in human and mouse genes and is unique to Oncoseq. Western blots were performed using anti-Oncoseq antibody at a concentration of 1:5000. Protein extract from $4\times10^5$ cells per sample is separated by 12% SDS/PAGE and transferred to a nitrocellulose membrane. The membrane is blocked with 5% dry milk and probed with desired antibodies. The filter is subsequently incubated with horseradish peroxide-conjugated secondary antibody, developed with enhanced chemiluminescence PLUS (ECL PLUS; Amersham Biosciences Corp., Piscataway, N.J.) and exposed to x-ray film. To standardize the amount of protein in each lane, the filter was stripped, probed with a polyclonal antibody against actin (Santa Cruz Biotechnology, Inc., Santa Cruz, Calif.), and developed with ECL Plus. Antibodies against Gli1 were obtained form a commercial source and utilized following manufacturer's protocols (Chemicon International, Temecula, Calif.).

Quantification of mRNA levels using real-time PCR analysis. Two µg of total RNA was reverse transcribed with MultiScribe™ Reverse Transcriptase (Applied Biosystems) according to the manufacturer's protocol. Conditions for all PCRs were optimized with regard to primers and various annealing temperatures (55-60° C.). Specificity of the RT-PCR amplification products were documented with a 4% high resolution NuSieve agarose gel electrophoresis and resulted in a single product with the desired length. Optimized results were transferred on the following ICycler Detection System (Bio-Rad Laboratories, Hercules, Calif.) using SYBR® green detection. For ICycler real-time PCR reaction, the 2× SYBR® Green PCR Master Mix (Applied Biosystems) was mixed with primers and cDNA template (80 ng). The following ICycler run protocol was used: denaturation program (95° C. for 10 min), amplification and quantification program depending on the primers and probe repeated 30-50 cycles (95° C. for 30 s, specified annealing temperature for 30 s, 72° C. for 30 s, and specified acquisition temperature for 15 s). Melting curve analysis was performed following amplification. (Morrison, T. B. et al. (1998) *Biotechniques* 24, 954-8, 960, 962) The acquisition temperature was set 1 to 2° C. below the $T_m$ of the specific PCR product. The relative quantification of a target gene in comparison to a reference gene (18S rRNA) was performed as described.(Pfaffl, M. W. (2001) A new mathematical model for relative quantification in real-time RT-PCR. *Nucleic Acids Res* 29, E45-E45; Schmittgen, T. D. & Zakrajsek, B. A. (2000) *J Biochem Biophys Methods* 46, 69-81).

PCR primer and conditions are detailed in Table 3.

TABLE 3

PCR primers and PCR conditions of the genes differentially regulated by Oncoseq.

| Sequence identity/Accession | Annealing temp (° C.) | PCR product size (bp) | Primers for kinetic RT-PCR (SEQ ID NO:) | Location of putative E-Box (from ATG) |
|---|---|---|---|---|
| Gli1/AB025922 | 55 | 102 | 5' primer: TGTTGTGGGAGGGAAGAAAC-3' (16)<br>3' primer: 5'-TGGCAGGGCTCTGACTAACT-3' (17) | −229 bp |

TABLE 3-continued

PCR primers and PCR conditions of the genes differentially regulated by Oncoseq.

| Sequence identity/Accession | Annealing temp (° C.) | PCR product size (bp) | Primers for kinetic RT-PCR (SEQ ID NO:) | Location of putative E-Box (from ATG) |
|---|---|---|---|---|
| Hormone receptor/X16995 | 55 | 86 | 5' primer: TGCGTATCACAGGGTATGGA-3' (18)<br>3' primer: 5'-TTTAAGTGGAAATGGGAGCG-3' (19) | −100 bp, −404 bp |
| 11β-hydroxysteroid dehydrogenase/X83202 | 55 | 61 | 5' primer: AGGAGCCGCACTTATCTGAA-3' (20)<br>3' primer: 5'-AACTGCCATCAAACAGGGAC-3' (21) | −1.5 Kb |
| TGF-β1/AJ009862/ X83202 | 60 | 93 | 5' primer: CCTGTCCAAACTAAGGCTCG-3' (22)<br>3' primer: 5'-TGTTGTACAAAGCGAGCACC-3' (23) | −70 bp |
| Insulin-like growth factor 2/ X71922 | 60 | 75 | 5' primer: TCCTCTTGAGCAGGGACAGT-3' (24)<br>3' primer: 5'-GAGAAACCTGGGAAGGGAAG-3' (25) | −1.4 kb, −1.6 kb |
| NOV/Y09257 | 55 | 108 | 5' primer: GTAACAGCCCTAGCAGGCAG-3' (26)<br>3' primer: 5'-CGCAGAGATGCAGAGACTTG-3' (27) | −170 bp, −390 bp, −594 bp* |
| latent TGF-β binding protein (LTBP-)/AF022889 | 55 | 148 | 5' primer: CACCATCACCTCTGCTCTCA-3' (28)<br>3' primer: 5'-CAGACACTGCTGTCCTCCAA-3' (29) | −115 bp |

*The promoter sequence for NOV was not available for *Homo sapiens* or *Mus musculus*. Therefore, the analysis for the presence of putative E-boxes was performed on the *Xenopus laevis* promoter sequence.

Immunofluorescence. Immunofluorescence staining using fluorescein isothiocyanate (FITC)-conjugated anti-Oncoseq antibody was performed according to Studer, L. et al. (Enhanced proliferation, survival, and dopaminergic differentiation of CNS precursors in lowered oxygen. *J Neurosci* 20, 7377-83. (2000).)

Immunohistochemistry—Five micrometer sections from cells were deparaffinized, rehydrated in graded alcohols and processed using the avidin-biotin immunoperoxidase method. Cancer cell lines showing Oncoseq protein expression and primary human lung squamous cell carcinomas displaying and not displaying Oncoseq protein expression by Western blotting were used. Briefly, sections were submitted to antigen retrieval by microwave treatment for 15 minutes in 0.01 M citrate buffer at pH 6.0. Slides were incubated in 10% normal goat serum for 30 minutes and then overnight at 4° C. in the polyclonal rabbit anti-human Oncoseq antibody (Antibody 1B-D125/1140) at a concentration of 0.18 micrograms/ml (1:5000 dilution of a 900 microgram/ml stock solution). Samples were then incubated with biotinylated anti-rabbit immunoglobulin at a 1:1000 dilution (Vector Laboratories, Inc, Burlingame, Calif.) for 30 minutes followed by binding an avidin-peroxidase conjugate (1:25, Vector Laboratories, Inc., Burlingame, Calif.) for 30 minutes. Diaminobenzidine was used as the chromogen and hematoxylin as the nuclear counterstain. As a control, parallel sections of the tumor were subjected to the same immunoperoxidase procedure except that the primary antibody was pre-incubated with the synthetic blocking peptide against which the antibody was raised. The ratio of blocking peptide to primary antibody was peptide 0.72 microgram/ml: 0.18 microgram/ml primary antibody.

Promoter assay. $2 \times 10^5$ NIH 3T3 cells transfected with pUSEamp-Oncoseq or with pUSEamp were placed on six-well plates in triplicate and transiently co-transfected with the reporter constructs, phRL-Gli1 promoter (ligated at the Sma I site; a kind gift from Dr. Shunsuke Ishii) and pSV-β-galactosidase (Promega), using lipofectin (Life Technologies). The cells were collected 48 hours post-transfection and luciferase activities measured using a TR717™ microplate luminometer (Applied Biosystems) and normalized to β-galactosidase activities. Luciferase and β-galactosidase activities were measured using a Dual-Light® System (Applied Biosystems). Each experiment was performed in triplicate and repeated three times.

Analysis of gene expression using oligonucleotide arrays. Gene expression profiling was performed on mouse gene probe arrays (Murine Genome U74 version 2, Affymetrix, Inc., Santa Clara, Calif.) with the capacity to display greater than 36,000 mRNA transcript levels of mouse genes and ESTs. Sample labeling and processing were performed according to the manufacturer's protocols. (Lockhart, D. J. et al. (1996) *Nat Biotechnol* 14, 1675-80). Data were collected by laser scanning and pixel levels analyzed with commercially available software (Affymetrix GeneChip software).

Statistical analysis—All analyses were performed using JMP4 statistical software (SAS Institute Inc., Cary, N.C.). Statistical significance was defined as a two tailed p-value less than or equal to 0.05. Qualitative and quantitative non-parametric comparisons were performed using Fisher's exact test and Mann-Whitney U-test respectively. Multivariable comparisons were made using the Kruskal-Wallis analysis of variance. Correlation analyses were performed using Spearman's Rho method. Survival curves were generated using the Kaplan Meier method and compared using the log-rank test.

B. Experimental Examples

Example 1

Gene identification and sequence analysis. Using a positional cloning approach, the duplication region at 3q26-27 was refined to within three highly amplified and overlapping YAC clones (803E3, 940H11, 923E6) at chromosomal band 3q26.3. The size of the genomic segment contained within these YAC clones was determined by pulse field gel electrophoresis (PFGE) and spanned ≈2 Mb. A bacterial artificial chromosome (BAC) contig was then constructed covering the 2 Mb genomic segment. Dual color fluorescence in situ hybridization (FISH) was utilized to further refine the minimal region of duplication. FISH analysis of several BACs prepared from 5 head and neck squamous cell carcinoma cell lines containing 3q26-37 duplication revealed two recurrent peaks of duplication in all cell lines contained within BAC clones 202B22 and 386M7, with mean copy numbers of 10.6 and 10.3, respectively. (See Singh et al., 2002.) Sequence analysis of the genomic insert in BAC 202B22, representing the amplified region in the 3q26.3 locus, failed to reveal the presence of any known genes. Sequence annotation using the GENSCAN and Genie prediction programs identified 11 potential genes, one of which gave an RNA product in RT-PCR analysis of cell lines derived from upper aerodigestive tract cancers. The full-length cDNA for this RNA was cloned and sequenced using RT-PCR on cell lines MDA886 and MDA 1186. The nucleotide sequence obtained from the cloned cDNA (918 bp; Oncoseq; FIG. 1a) contains an open reading frame encoding a 259 amino acid residue protein with a predicted molecular weight of 30.1 kDa (FIG. 1a, shown with the conventional one-letter amino acid code). The predicted start codon has the required Kozak consensus sequence (ANNATG). The 5' UTR sequence has a high G+C content (70%), and no additional ATG's upstream were identified by 5' RACE. Thus the ascribed start codon likely represents a genuine start site for translation. A polyadenylation signal (AATAAA) is located at 833-838 bp.

Only one domain was identified using the National Center for Biotechnology Information Conserved Domain Search, DUF298, which is a basic region-helix-loop-helix-leucine zipper motif.

gnl|CDD|15599, pfam03556, DUF298, Domain of unknown function (DUF298). Members of this family contain a basic helix-loop-helix leucine zipper (b-HLH/Zip) motif beginning at residue 134 and ending at residue 248 (FIG. 1a, bold font).

```
           CD-Length = 117 residues, 100.0% aligned
           Score =  146 bits (371), Expect = 2e-36
Query:  134 TEKLKAQIPKMEQELK-EPGRFKDFYQFTFNFAKNPGQKGLDLEMAIAYWNLVLNG-RFR  191

Sbjct:    1 IQKLQARLPCLESELEGDPEKFKDIYRFAFNEAKDPDQKNLDLETAIACWDLVFGSCRWP   60

Query:  192 LLDLWNKFLLEHBKRSIPKDTWNLLLDFSTMIADDMSNYDEEGAWPVLIDDFVEFAR     248

Sbjct:   61 LLEHWKDFLEPHHNRAIPKDTWNLLLEFSRTIDPDLSNYDEEGAWPVLIDEFVEWLQ     117
```

The Oncoseq gene spans ≈43.6 Kb, comprising 7 exons (FIG. 1b). A homologous pseudogene was also identified on chromosome 6 (RP42), which does not contain an open reading frame sufficient to support transcription. BLAST analysis of the gene sequence to different species showed 56-99% identity with homologs identified in *M. musculus, A. thaliana, D. melanogaster* and *C. elegans*, indicating significant evolutionary conservation, as seen in the dendrogram of FIG. 1c The b-HLH/Zip motif was highly conserved amongst the orthologous genes. The presence of the bHLH/Zip motif suggests Oncoseq may function as a transcription factor. This possibility is supported by the effect of Oncoseq expression on Gli1 expression presented in Examples 8-10.

Example 2

Tissue Expression of Oncoseq Nucleic Acids

Figure 2B:
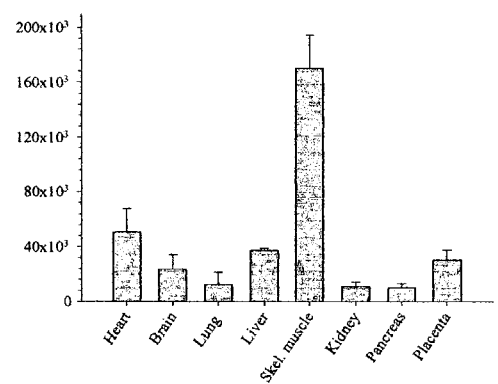
Figure 2C:
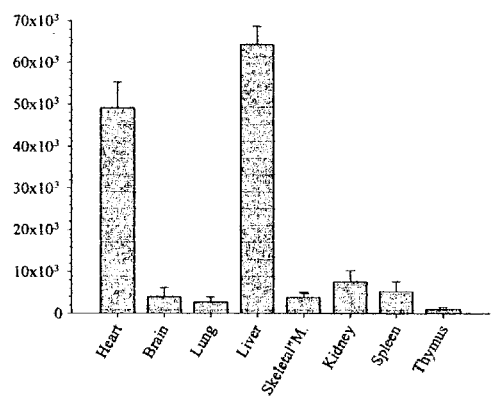

Hybridization of a full-length probe of the Oncoseq sequence to a multi-tissue northern blot revealed high-level gene expression in heart and skeletal muscle, with three predominant transcripts (FIG. 2a). Low level expression was seen in brain, kidney, small intestine, placenta and lung. The expression level and relative ratios of these apparent splice forms varied from tissue to tissue. Gene expression was confirmed by real-time RT-PCR in adult and fetal tissues. The highest expression in adults was seen in skeletal muscle and heart, similar to findings by northern blot. In fetal tissues, the expression was highest in liver and heart, with lower level expression present in other tissues (FIG. 2b). Expression of Oncoseq cDNA by in vitro transcription and translation yielded a protein having the predicted size, approximately 30 kDa. In addition, Western blot analysis confirmed the presence of an Oncoseq protein product of predicted size in primary tumor and cell lines derived form upper aerodigestive tract carcinomas (data not shown)

Example 3

Oncoseq Drives Selection for 3q Duplication

Figure 3:
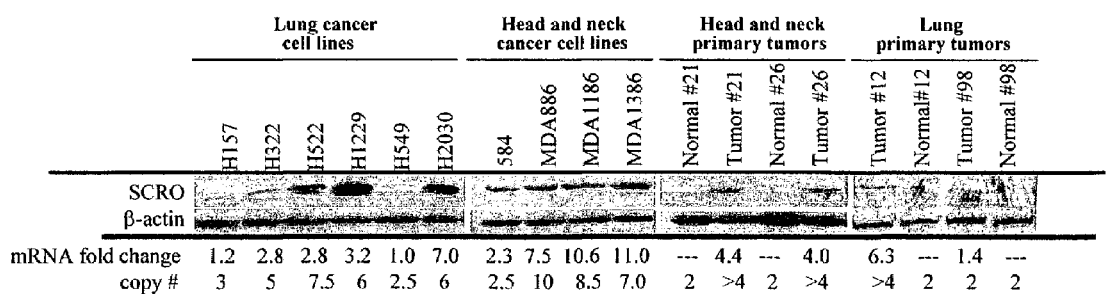
FIG. 3. Fold change in Oncoseq (identified as SCRO) mRNA in several tumor cell lines and primary tumor samples.
Figure 4:
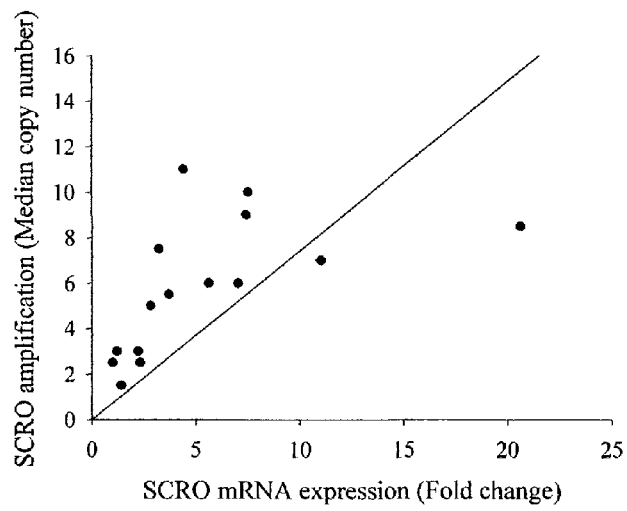
FIG. 4. Correlation of Oncoseq (identified as SCRO) copy number by FISH using BAC 202B22 as a probe and Oncoseq mRNA expression by real time PCR in 15 cell lines derived from upper aerodigestive tract carcinomas.

To validate Oncoseq as a target that drives selection for 3q duplication, a genetic link was established by correlating gene duplication with over expression and determined its clinical significance by analyzing the presence, incidence and clinical significance of gene over expression in primary tumors. Duplication was found to be linked to Oncoseq expression by screening representative cell lines and primary tumors derived from lung and head and neck cancer. FIG. 3 shows the fold-change in mRNA level in several cancer cell lines and primary tumors; the primary tumors are compared with normal tissues taken from the same patient. The gene copy number evaluated for the same sample is also shown. It is seen that high copy number correlates with large increases in mRNA expression. This result is corroborated in FIG. 4, in which it seen that significant correlation was found in 15 cell lines derived from upper aerodigestive tract carcinomas between Oncoseq duplication and corresponding RNA expression (r=0.81; p<0.001)). These results were verified by Southern and Northern blot analyses in selected cell lines (data not shown).

The prevalence of Oncoseq over expression in primary tissues was assessed by real-time RT-PCR. Over expression of Oncoseq mRNA relative to matched normal controls was identified in 21/44 (48%) primary lung, 16/45 (36%) head and neck, 4/9 (44%) cervical, and 4/15 (27%) ovarian carcinomas (data not shown). Western blot analysis of protein expression in selected primary tumors samples corroborated the real-time PCR findings. The median level of Oncoseq mRNA expression was higher in squamous cell carcinomas (704.0 pg) than normal lung tissue (104.0 pg) or adenocarcinomas (57.3 pg) (FIG. 5a), consistent with CGH data showing that 3q amplification is an event specific to this histology. This analysis of non-small cell lung cancers showed expression of Oncoseq mRNA was increased in squamous cell carcinomas (61%) but not in adenocarcinomas (9%; P=0.004). These results provide indicia of values that do, and do not, represent pathological amounts of Oncoseq mRNA in a sample. The present results extend earlier findings observed at a chromosomal level (Bjorkqvist, A. M. et al. (1998) *Genes Chromosomes Cancer* 22, 79-82).

Survival analysis among human patients showed a negative correlation between high-level Oncoseq expression and outcome in lung carcinomas, for patients with elevated Oncoseq expression had poorer survival outcomes (P=0.05), indicating Oncoseq gene duplication imparts a more aggressive phenotype (FIG. 5b).

Example 4

Oncoseq Induces Transformation in Vitro

In vitro transformation assays were performed using NIH-3T3 cells and HaCaT (benign transformed epithelial cells), stably or transiently transfected with the full length open reading frame for Oncoseq. NIH3T3 cells represent an established transformation assay system. Stable transfection of NIH-3T3 was performed under neomycin selection and two clones (clones 14 and 28) were selected for further analysis based on up-regulation of Oncoseq protein to levels present in cancer cell lines with 3q duplication. FIG. 6 shows a 4 fold increase in expression of Oncoseq protein over empty vector controls in NIH 3T3 cells. When compared to the empty vector transfected cells (FIG. 7 left panes), morphological changes suggestive of malignant transformation were observed in both pUSEamp-Oncoseq clones 14 and 28, including a dedifferentiated morphology, globular cell structure, increased nuclear size, and an increased nuclear to cytoplasmic ratio (FIG. 7, middle panel). In addition, Oncoseq-transfected cells showed formation of cellular nests (FIG. 7 right panel), indicating loss of contact inhibitory signals. Oncoseq transfection, using clone 28, imparted growth advantages to NIH-3T3 cells, including a 2-3 fold increase in growth rate (FIG. 8a) in conjunction with a significantly increased S phase fraction in pUSEamp-Oncoseq-3T3 (27.3%) compared with pUSEamp-3T3 cells (3.8%) by FACS analysis (data not shown). Moreover, Oncoseq transfected NIH 3T3 cells retained growth activity in serum deficient conditions (FIG. 8c), whereas cells transfected with empty vector became depleted under these conditions. Thus Oncoseq-transfected cells showed resistance to serum deficient conditions indicating a growth advantage.

Soft agar assay showed a significantly higher rate of colony formation in NIH-3T3 stably transfected with pUSEamp-Oncoseq (clones 14 and 28) compared with those transfected with pUSEamp (p<0.001; FIG. 9a), confirming the acquisition of anchorage independent growth. Increased in vitro invasive potential was also conferred to both NIH-3T3 clones (69.5%±8.7% invasive fraction) compared with control cells (18.50%±6.7% invasive fraction) as shown by the modified Boyden chamber invasion assay (p<0.001; data not shown). Oncoseq is felt to play an oncogenic role in vivo in HaCaT cells, which are of epithelial lineage. The Oncoseq gene transforms HaCaT cells, since it was found that 352±97 colonies per 12 well plate were formed on the soft agar forced suspension culture assay using cells transiently transfected with Oncoseq, compared with no colonies formed by wild type and cells transfected with empty vector.

Example 5

In Vivo Tumorigenicity of Oncoseq

In vivo tumorigenicity assay in NIH-BALB/c nude mice injected with NIH 3T3 cells transfected with pUSEamp-Oncoseq (clone 14) showed that tumors formed in 6 of 6 mice within 8 weeks. In contrast, no tumors developed up to 12 weeks in 6 mice injected with NIH 3T3 cells transfected with pUSEamp-313 cells ((P=002) see FIG. 9b). Autopsy and histopathological analyses revealed the presence of tumor metastasis to pelvic lymph nodes in 3 of 6 pUSEamp-Oncoseq-3T3 associated tumors. Histologically, tumors derived from NIH-3T3-Oncoseq (clone 28) cells showed a poorly differentiated architecture and a heterogeneous cellular morphology with abundant mitotic activity. The results in this Example show that Oncoseq is directly implicated in formation of ectopic tumors in an animal model.

Example 6

Role of Oncoseq in Maintaining Malignant Phenotype

Figure 11A:
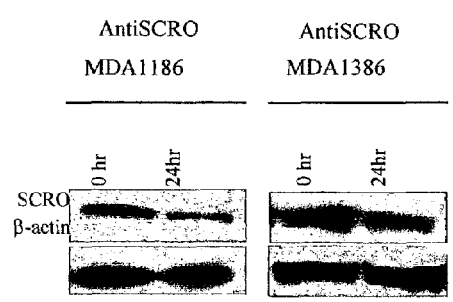
FIG. 11. Panel a. Western blot of Oncoseq expression after transfection of Oncoseq antisense (identified as AntiSCRO) into MDA1186 and MDA1386 cells. Panel b. Dose titration of Oncoseq antisense plasmid in cell lines with (MDA1186 and MDA1386) and without (584 and H157) high-level gene duplication and expression of Oncoseq. The MTT cell viability assay was carried out 48 hours after transient transfection with plasmid. Panel c. Hoechst staining of Oncoseq antisense transfected MDA1186 cells (left) and cells transfected with empty vector (right). Panel d Cellular DNA Fragmentation ELISA in MDA1186 cells and 584 cells, transfected with antisense against Oncoseq or with control vector.
Figure 11B:
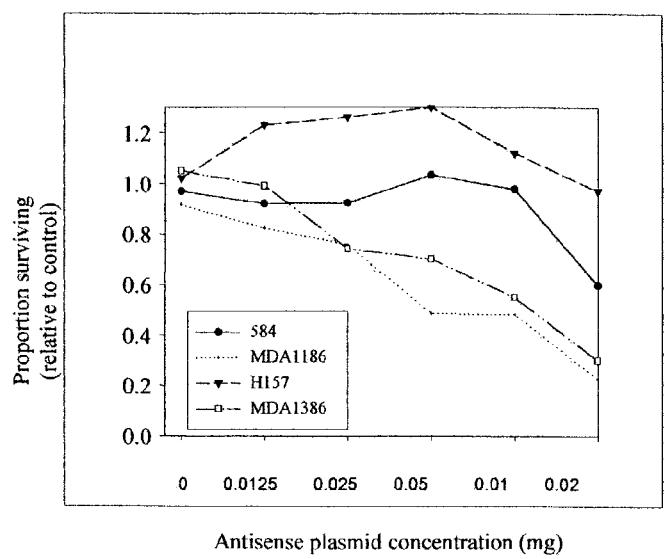
Figure 11C:
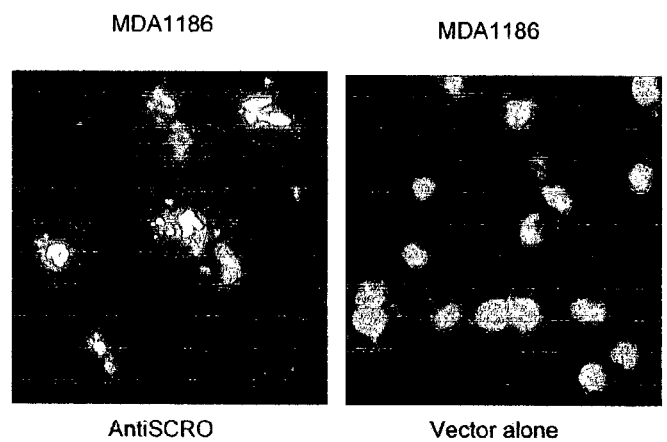
Figure 11D:
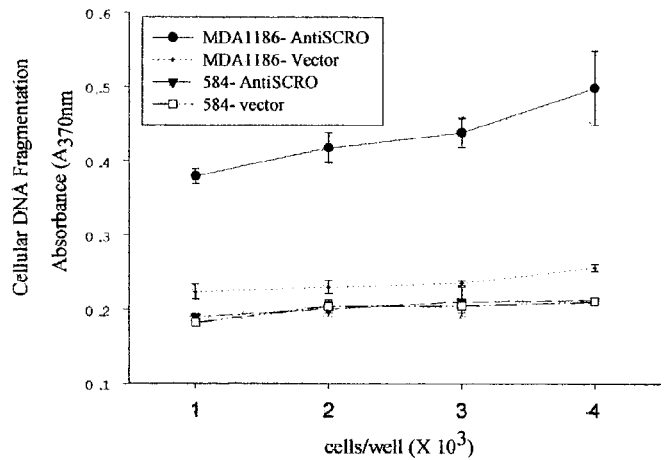

The effect of transfection with a vector harboring antisense to Oncoseq was assessed in several cell lines derived from squamous cell carcinomas. The efficacy of transfection with a vector containing full length antisense, pUSEamp-asOncoseq was examined. A 3-5 fold transfection-related suppression in Oncoseq protein levels was found in MDA1186 and MDA1386 cells (FIG. 11a). A dose titration assessing the transfection of pUSEamp-asOncoseq into cell lines with high levels of Oncoseq duplication and over expression of protein (MDA1186 and MDA1386) resulted in significant cell death. In contrast, minimal effects by antisense transfection were seen on cell lines with normal endogenous amounts of Oncoseq mRNA (H157 and 584; P<0.05). Survival is shown relative to matched cells transfected with empty vector. (See FIG. 11b). FACS analysis indicated a significant increase in the GO fraction (data not shown). Hoechst staining showed nuclear condensation in the case of transfection with pUSEamp-asOncoseq (FIG. 11c), and Cellular DNA Fragmentation ELISA assay showed increased nucleosome accumulation in the cytoplasmic fraction in MDA1186 cells treated with pUSEamp-asOncoseq, but not with MDA1186 cells transfected with control vector, nor with 584 cells transfected with either vector (FIG. 11d). This result demonstrates that antisense transfection in cells having high copy numbers of Oncoseq results in cell death consequent to apoptosis.

The results of this Example show that Oncoseq plays a critical role in maintaining the malignant phenotype in cells carrying high gene duplication, and that antisense to Oncoseq can reverse this malignancy.

Example 7

Subcellular Localization of Oncoseq Protein

Figure 10:
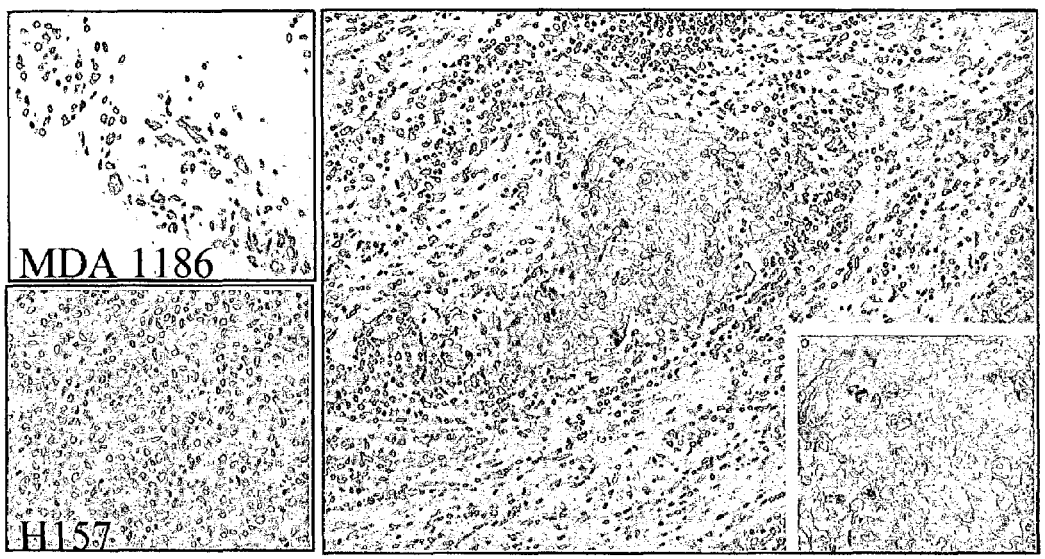
FIG. 10. Immunohistochemical analysis using anti-Oncoseq antibody in MDA1186 and H157 cells, and in a primary lung squamous cell carcinoma (100×, right panel; 400×, inset to right panel).

To examine the subcellular location of human Oncoseq, immunohistochemical and fluorescence immunolocalization experiments were conducted. FIG. 10 shows immunohistochemical analysis using anti-Oncoseq antibody, which indicates both nuclear and cytoplasmic localization of Oncoseq protein in a squamous carcinoma cell line exhibiting Oncoseq protein expression as determined by western blot (MDA1186), but absence of antibody staining in a normal cell line (H157). Analysis of a primary lung small cell carcinoma (FIG. 10, right) shows expression of Oncoseq in the primary tumor, but not surrounding stromal cells (100×). High power view (400×; inset) shows both nuclear and cytoplasmic Oncoseq protein expression.

Figure 12:
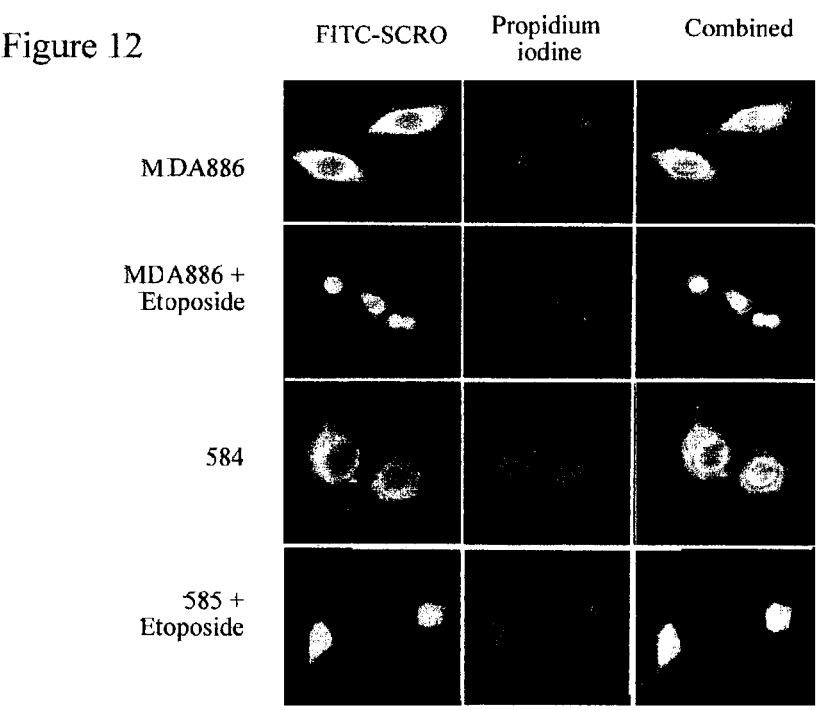
FIG. 12. Fluorescence microscopy images of cells under normal and stressed conditions. First column, staining with fluorescent tagged anti-Oncoseq antibody. Second column, staining with propidium iodide, which binds to DNA. Third column, superposition of images obtained in the first and second columns. First row, MDA886 cells. Second row, MDA886 cells with etoposide added. Third row, 584 cells. Fourth row, 584 cells with etoposide added.

In cell lines derived from head and neck primary carcinomas (MDA886 and 584 cells) (FIG. 12, first and third rows), Oncoseq protein was detected, by fluorescence immunolocalization, in the cytoplasm, perinuclear region and nucleus (FIG. 12). Under stress conditions resulting from exposure to etoposide, the Oncoseq protein was observed only in the nucleus (FIG. 12, second and fourth rows; also observed in NIH-3T3 cells (not shown)), suggesting that Oncoseq protein is translocated into the nucleus under these conditions.

Example 8

Detection of Altered Gene Expression Due to Oncoseq

Gene expression analysis was performed using Affymetrix arrays (Affymetrix, Inc., Santa Clara, Calif.) on pUSE-amp-Oncoseq stably transfected NIH 3T3 clones 14 and 28, with NIH 3T3 cells transfected with empty vector serving as the control. The transcription of several genes was altered in both clones, including many genes linked to malignant transformation (Table 4).

TABLE 4

Differentially expressed genes identified by gene expression profiling.

| Sequence identity (GenBank/EMBL) of differential regulation | Accession | Level (S14/S28)** |
|---|---|---|
| Nuclear proteins (transcription factors, DNA processing enzymes) | | |
| Gli1* | AB025922 | 18.5/24.1 |
| hormone receptor (HMR)* | X16995 | 13.9/16.1 |
| DNA ligase I | U19604 | 9.3/14.9 |
| early growth response 2 (EGR2) | M24377 | 9.4/8.0 |
| mCDC46 protein | D26090 | 3.3/5.2 |
| nuclear P1 protein | X62154 | 2.8/5.4 |
| nuclear protein np95 | D87908 | 2.4/3.0 |
| zinc finger protein | X95504 | −2.1/−5.1 |
| Id4 dominant negative helix-loop-helix | AJ001972 | −2.5/−3.7 |
| Cytokines, growth factors and receptors | | |
| transforming growth factor-β1* | AJ009862 | 12.1/14.9 |
| insulin-like growth factor 1* | X04480 | 7.0/9.6 |
| 204 interferon-activatable protein | M31419 | 2.2/3.7 |
| brain-derived neurotrophic factor | X55573 | 2.2/3.6 |
| platelet-derived growth factor-inducible protein (JE) | M19681 | 2.2/3.4 |
| insulin-like growth factor binding protein-6 | X81584 | 2.0/3.3 |
| keratinocyte growth factor receptor | M63503 | −3.1/−3.7 |
| latent TGF beta binding protein (LTBP-1)* | AF022889 | −4.8/−36.6 |
| nephroblastoma overexpressed gene (NOV)* | Y09257 | −10.3/−12.5 |
| insulin-like growth factor 2* | X71922 | −100.3/−101.7 |
| Signaling molecules | | |
| secreted frizzled related protein sFRP-1 (SFRP1) | U88566 | −2.6/−9.8 |
| secreted frizzled related protein sFRP-2 (SFRP2) | U88567 | −5.8/−14.7 |
| Metabolic enzymes, transporters, ion channels | | |
| 11beta-hydroxysteroid dehydrogenase/carbonyl reductase | X83202 | 11.8/24.3 |
| ceruloplasmin | U49430 | 3.7/4.1 |
| RNA1 homolog (FUG1) | U20857 | 2.1/3.1 |
| hyaluronan synthase 2 (HAS2) | U52524 | 2.0/3.0 |
| glutathione S-transferase (GSTT1) | X98055 | −2.4/−4.2 |
| Cytoskeletal components, adhesion molecules | | |
| entactin-2 | AB017202 | −2.0/−6.6 |
| Extracellular proteins | | |
| adrenomedullin precursor | U77630 | −2.1/−3.2 |
| osteoglycin | D31951 | −2.2/−6.0 |
| dickkopf-2 (dkk-2) | AJ243963 | −2.4/−9.4 |
| thymosin B4 (TMSB4X) | U38967 | −2.2/−4.2 |

TABLE 4-continued

Differentially expressed genes identified by gene expression profiling.

| Sequence identity (GenBank/EMBL) of differential regulation | Accession | Level (S14/S28)** |
|---|---|---|
| Others | | |
| interferon-induced 15-KDa protein | X56602 | 7.9/9.6 |
| double LIM protein-1 | D88792 | 2.2/3.7 |
| sex-limited protein Slp (w7) alpha-gamma chain | X06454 | −2.7/−3.7 |
| H19 | X58196 | −2.9/−3.9 |
| semaphorin IV isoform β | AF080090 | −3.7/−14.9 |

*Genes that contained E-box and were verified by kinetic RT-PCR.
**Gene expression is given for pUSEamp-Oncoseq-3T3 Clone 14/pUSEamp-Oncoseq-3T3 Clone 28 relative to that of pUSEamp-3T3.

Eight of the genes with altered expression in Oncoseq transfected cells contain E boxes (5'-CANNTG-3') in the promoter region, a characteristic binding site for bHLHZip proteins (Weiner, J. A., et al. (1998) *J Biol Chem* 273, 15913-9) such as Oncoseq (Table 3). Real time PCR in all 8 genes containing E-box, induced by Oncoseq transfection, confirmed increased or decreased expression levels in Oncoseq transfected cells compared to the control (Table 4).

Example 9

Induction of Gli1 Expression by Oncoseq

Figure 13:
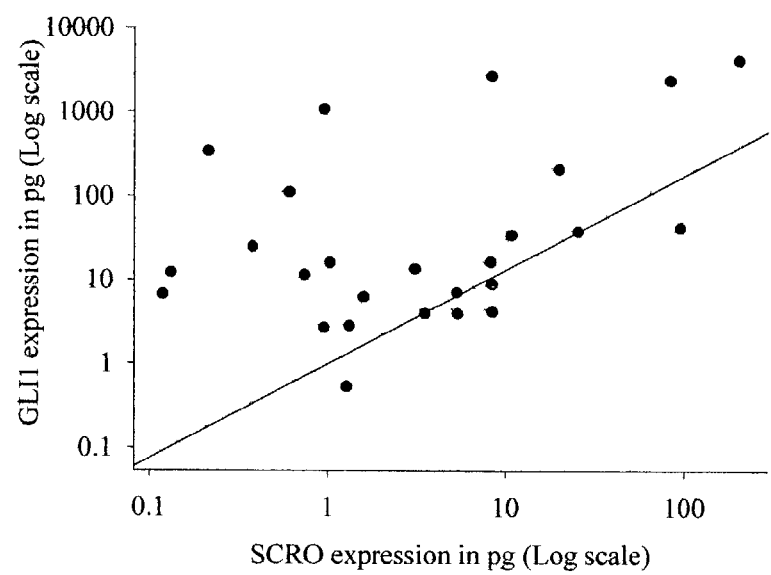
FIG. 13. Expression of Gli1 plotted using logarithmic ordinate scales against the expression of Oncoseq (identified as SCRO) in 26 non-small cell carcinomas of lung origin, matched to histologically normal lung tissue showed a significant correlation between Oncoseq and Gli1 expression, relative to matched normal controls, expressed using logarithmic scales on the ordinates (r=0.75; p<0.001).

One of the genes over-expressed in the presence of Oncoseq is Gli1. This finding is of particular interest, as Gli1 plays an essential role in the development of lung, trachea and esophagus (Park, H. L. et al. (2000) *Development* 127, 1593-605; Motoyama, J. et al. (1998) *Nat Genet* 20, 54-7), the same tissue structures in which the present invention has shown that Oncoseq has oncogenic activity. Further supporting this association, real-time RT-PCR and western blot analyses showed a significant correlation between Oncoseq and Gli1 expression at both the nucleic acid and protein levels in cancer cell lines and primary carcinomas in 26 non-small cell carcinomas of lung origin, referenced to histologically normal lung tissue (FIG. 13; r=0.75; p<0.001). Further analysis of the oligonucleotide array data showed the dysregulation of several genes whose activities are downstream of Gli1 activation, including Gli2, cyclin D, fibroblast growth factor receptor FGFR, insulin-like growth factor (IGF), IGF receptor, and ceruloplasmin.

Example 10

Gli1 Promoter Activity Induced by Transfection with Oncoseq

Figure 14:
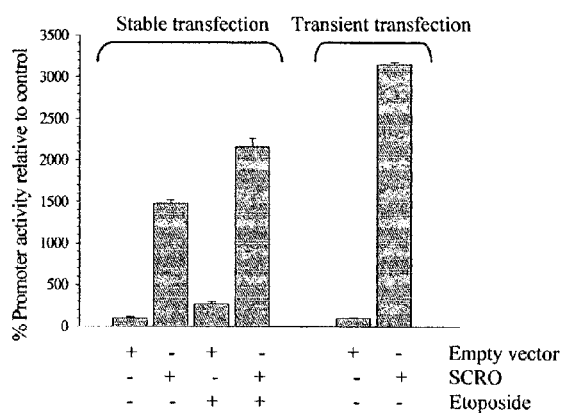
FIG. 14. Gli1 promoter activity in NIH-3T3 cells stably transfected or transiently transfected with pUSEamp-Oncoseq. These experiments were done without or with co-treatment with etoposide.

To confirm a transcriptional relationship between of Oncoseq and Gli1 the impact of Oncoseq expression on Gli1 promoter activity was assessed. A significant increase in phRL-Gli1 promoter activity and Gli1 protein levels was observed in NIH-3T3 cells both stably and transiently transfected with pUSEamp-Oncoseq plasmid compared to control cells (FIG. 14). The effect of Oncoseq expression on the Gli1 promoter was augmented by addition of etoposide (FIG. 14), resulting in an increase in Gli1 protein levels 12-24 hours after treatment.

Figure 15A:
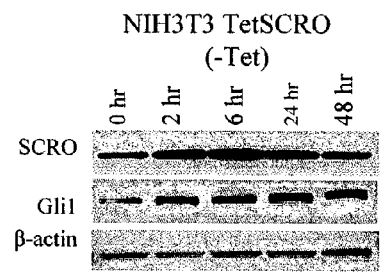
FIG. 15. Western blot analysis of protein expression in NIH-3T3 cells transfected with Oncoseq in a vector allowing induction upon removal from a tetracycline-containing medium. Panel a. Expression of Oncoseq protein and Gli1 protein at various times after removal of tetracycline. Panel b. Expression of Gli1 protein in the presence of etoposide at various times after removal of tetracycline.
Figure 15B:
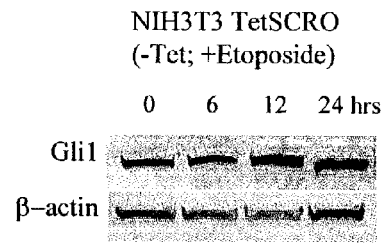

This observation was corroborated in an Oncoseq expression system inducible by removal from tetracycline stably transfected into 3T3 cells. Western blots show an increase in Oncoseq protein levels upon the removal of tetracycline and resultant increase in Gli1 protein levels (FIG. 15a). The effect of tetracycline removal on Gli1 protein levels was not seen in 3T3 cells transfected with empty vector (data not shown). In addition, co-treatment with etoposide, which results in nuclear localization of the Oncoseq protein (Example 7, FIG. 12) and a significant increase in Gli1 promoter activity (FIG. 14) also results in increased Gli1 protein levels (FIG. 15b).

Figure 16A:
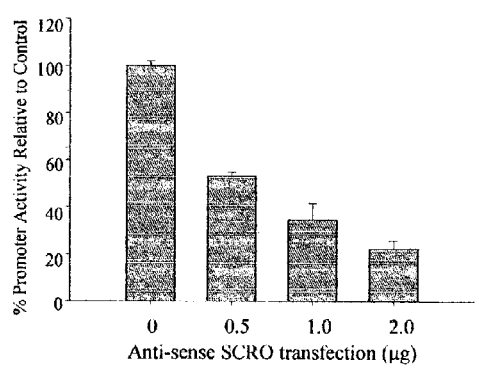
FIG. 16. Effect of Oncoseq antisense transfection into A431 cells on Gli1 expression. Panel a. Dose response of Gli1 promoter activity as a function of the amount of Oncoseq antisense plasmid transfected. Panel b. Western blot analysis of Oncoseq and Gli1 protein expression as a function of the amount of Oncoseq antisense plasmid transfected.
Figure 16B:
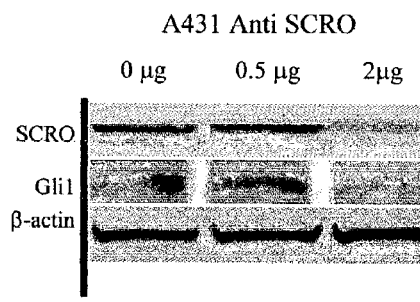

The transfection of Oncoseq antisense in A431 cells resulted in a significant reduction in Gli1 promoter activity (FIG. 16a) and a corresponding decrease in both Oncoseq and Gli1 protein levels (FIG. 16b). These results indicate that Oncoseq regulates the transcription and translation of Gli1.

Example 11

Expression of Oncoseq mRNA in Tongue Carcinomas and Normal Tongue Tissues

To determine the status of gene expression in primary tongue SCC, 49 matched pairs of primary tumor tissues and histologically normal adjacent mucosae were examined for mRNA levels of Oncoseq. The mRNA expression of Oncoseq was significantly greater in malignant tissues in comparison with the mRNA levels in histologically normal mucosa (13640±1090 pg. vs 6277±652.1 pg., P<0.0001). If the cut-off value for distinguishing between normal expression and over-expression of Oncoseq mRNA is set as two-fold or greater increase in tumor mRNA expression relative to matched normal tongue controls, then 24.5% of patients ($^{12}/_{49}$) expressed high levels of Oncoseq.

Example 12

Correlation of Oncoseq Expression with Clinicopathological Characteristics

Expression of Oncoseq in 49 primary tumors was correlated to clinicopathological variables in order to determine their interrelationship. Statistically significant correlations were identified between Oncoseq over-expression and several established prognostic variables including a tumor thickness of greater than 10 mm (P=0.05; Odds Ratio=4.167), the presence of nodal metastasis (P=0.05, Odds Ratio=4.40), and advanced pathological stages (P=0.02, Odds Ratio=6.25).

The observed association between Oncoseq and tumor thickness, a marker for invasiveness, suggests that Oncoseq may play a role in tumor invasion. Since the presence of neck nodal metastasis is by far the most decisive influence on prognosis in patients with head and neck se, its relationship with Oncoseq is of interest. Among various biological and clinicopathological parameters examined (data not shown), Oncoseq was the only factor that demonstrated a significant correlation with nodal metastasis.

Example 13

Predictive Values of Clinicopathological Characteristics and Oncoseq Expression on Nodal Metastasis The presence of nodal metastasis is the single most important predictor of outcome in head and neck SCC. Oncoseq over-expression was significantly correlated with cervical nodal metastases (p=0.05; Odds Ratio=4.40), whereas there was no correlation of cervical metastasis with age, gender, smoking, alcohol, grade, tumor thickness, perineural or perivascular invasion and T classification. Parameters that had P values less than 0.2 were selected for multivariate regression analysis. Oncoseq over-expression was the only characteristic to retain independent prognostic influence on nodal metastasis.

Example 14

Relationships with Survival

Poorly differentiated histological grade, a tumor thickness of greater than 10 mm, a T stage value of III and IV, positive nodal status, advanced pathological stage, and Oncoseq over-expression were all significantly associated with a poorer overall survival on univariate analysis (P=0.02, 0.02, 0.002, 0.002, 0.002, and 0.02 respectively). Furthermore, tumor thickness, T stage, nodal status, overall stage, and Oncoseq status demonstrated statistically significant correlation with worse disease-specific survival and relapse-free survival. (Multivariate analysis was not possible due to the small number of events.) These results demonstrate that there is a prognostic value of Oncoseq in oral tongue cancers.

Example 15

Detection or Quantitation of an Oncoseq Nucleic Acid, and Assessment of Copy Number Thereof A biological sample is obtained from a patient suspected of suffering from squamous cell carcinoma. The sample is obtained in such a way that both the tissue suspected of being cancerous and the neighboring tissue presumed to be normal are removed. The presumed normal tissue serves as a control or reference. The suspect tissue and the normal tissue are separately homogenized in the presence of nuclease inhibitors. The chromatin is isolated from the cell lysate, and optionally the DNA is liberated from its chromosomal nucleoprotein in each sample. The resulting purified DNA preparations are separately subjected to PCR using Oncoseq-specific primers to provide an Oncoseq amplicon. In addition, the purified DNA preparations are subjected to PCR using primers specific for a reference gene such as beta actin or glyceralde-3-phosphate dehydrogenase. The amount of amplicon for Oncoseq is normalized to the amount of amplicon for the reference gene, in the presumed cancer sample and in the normal sample, and the normalized amounts of amplicon are compared to each other. This accomplishes detection and quantitation of the Oncoseq gene in both the presumed cancer sample and the normal sample. In addition, any fold-enhancement of the normalized Oncoseq level in the suspected cancer sample over the normalized amount of Oncoseq in the presumed normal sample represents an increase in copy number of the Oncoseq gene in the suspected cancer sample.

Example 16

Detection or Quantification of Transcriptional Expression of an Oncoseq Nucleic Acid Suspect and presumed normal tissues are prepared and homogenized as described in Example 11. If necessary, the RNA-containing fractions are purified in each. Each sample is subjected to RT-PCR to prepare amplified cDNA using Oncoseq-specific primers to provide an Oncoseq amplicon. In addition, the purified RNA preparations are subjected to RT-PCR using primers specific for a reference gene such as beta actin or glyceralde-3-phosphate dehydrogenase. Alternatively, a DNA fraction may be directly expanded by PCR of the reference gene. The amount of amplicon for Oncoseq is normalized to the amount of amplicon for the reference gene, in the presumed cancer sample and in the normal sample, and the normalized amounts of amplicon are compared to each other. This accomplishes detection and quantitation of the expressed Oncoseq gene in both the presumed cancer sample and the normal sample. In addition, any fold-enhancement of the normalized Oncoseq level in the suspected cancer sample over the normalized amount of Oncoseq in the presumed normal sample may be related to an increase in copy number of the Oncoseq gene in the suspected cancer sample.

Example 17

Evaluation of an Average Amount of Oncoseq DNA Sequence in Various Samples a. Normal Samples. A large number of surgical samples of normal squamous cell tissue in the anatomical vicinity of a suspected SCC is obtained. The DNA is purified and amplicons for Oncoseq and for a reference gene are expanded by PCR as described in Example 11. The ratios of the amount of Oncoseq amplicon to the amount of reference gene amplicon are calculated for each sample and the average value for normal samples is obtained.

b. Primary Tumor Samples. The same process is followed as for part a, except that the surgical samples used are samples of demonstrated primary SCCs. The ratios are calculated and the average value for primary tumor samples is obtained.

c. Metastatic Tumor Samples. The same process is followed as for part a, except that the surgical samples used are samples of metastasized SCCs. The ratios are calculated and the average value for metastasized carcinoma samples is obtained.

Example 18

Evaluation of an Average Amount of Oncoseq Transcriptionally Expressed Sequence in Various Samples a. Normal Samples. A large number of surgical samples of normal squamous cell tissue in the anatomical vicinity of a suspected squamous cell carcinoma. The RNA is purified and amplicons for Oncoseq and for a reference gene are expanded by RT-PCR as described in Example 12. The ratios of the amount of Oncoseq amplicon to the amount of reference gene amplicon are calculated for each sample and the average value of transcriptionally expressed Oncoseq nucleic acid for normal samples is obtained.

b. Primary Tumor Samples. The same process is followed as for part a, except that the surgical samples are samples of demonstrated primary SCCs. The ratios are calculated and the average value of transcriptionally expressed Oncoseq nucleic acid for primary tumor samples is obtained.

c. Metastatic Tumor Samples. The same process is followed as for part a, except that the surgical samples are samples of metastasized SCCs. The ratios are calculated and the average value of transcriptionally expressed Oncoseq nucleic acid for metastasized carcinoma samples is obtained.

Example 19

Diagnosis of, Prognosis of, and Therapeutic Strategy for, Squamous Cell Carcinoma Patients A surgical sample of a suspected squamous cell carcinoma and of adjacent normal squamous cell tissue is obtained from a patient suspected of suffering from the carcinoma. The samples are separately expanded either to evaluate amounts of Oncoseq DNA as described in Example 11 or transcriptionally expressed Oncoseq amounts as described in Example 12. The adjacent normal sample serves as a control, and should reproduce the average normal values found in Examples 13 or 14, respectively, within expected statistical variation. The suspected carcinoma sample is evaluated, and the resulting value is compared to the normal average value, the primary tumor average value and the metastatic tumor value obtained using the procedures described in Examples 13 or 14, respectively, using statistical analysis such as that described in the Examples, Section A, Methods and Materials, to establish statistical significance. The value found for the surgical sample is assigned to being either a normal value, a value characteristic of a primary tumor, or a value characteristic of a metastatic tumor, within an acceptable statistical level of significance. Based on the result, a contribution has been made to the diagnosis of the cancer, and to the prognosis of the cancer in the patient. Additionally, the result can contribute to establishing a course of therapy to pursue among a choice of such therapies. For example, in addition to surgical resection, choices may include radiation therapy or chemotherapy, and, within chemotherapy, a choice among various chemotherapeutic agents.

Example 20

Detection or Quantification of an Oncoseq Protein

A biological sample is obtained from a patient suspected of having SCC. The sample is obtained via biopsy in such a way that both tissue suspected of being cancerous and neighboring tissue presumed to be normal are removed. The presumed normal tissue serves as a control or reference. The suspect tissue and the normal tissue are separately homogenized in the presence of protease inhibitors. Protein-containing fractions are isolated. The cytoplasmic, microsomal, membrane-bound, and nuclear fractions are probed for the presence of an Oncoseq protein. Protein detection is carried out by use of an Oncoseq-specific antibody in an ELISA format. For example, a sample fraction is layered on a plate so that proteins present in the sample adhere to the plate. An Oncoseq-specific antibody that is conjugated to a secondary probe or label is then applied to the plate after minimizing nonspecific binding, and the amount of anti-Oncoseq antibody is assessed via the secondary probe or label. Alternatively, a first anti-Oncoseq antibody is applied to a plate, the sample is applied and a second anti-Oncoseq antibody that does not compete with the first antibody is applied. The amount of the second anti-Oncoseq antibody is detected with a suitable probe or label. The amount of anti-Oncoseq antibody (first alternative) or second anti-Oncoseq antibody (second alternative) that is detected correlates linearly with the amount of Oncoseq protein in the sample. The amount of a reference protein such as beta actin or glyceraldehyde-3-phosphate dehydrogenase in the sample is obtained in similar fashion.

The amount of Oncoseq protein is normalized to the amount of the reference protein, in each of the presumed cancer sample and the normal sample, and the normalized amounts of protein are compared to each other. This accomplishes detection and quantitation of the Oncoseq protein in both the presumed cancer sample and the normal sample. In addition, any fold-enhancement of the normalized Oncoseq protein level in the suspected cancer sample over the normalized amount of Oncoseq protein in the presumed normal sample represents an increase in copy number, transcriptional expression, and/or translational expression, of the Oncoseq gene in the suspected cancer sample.

Example 21

Evaluation of an Average Amount of Oncoseq Protein in Various Samples a. Normal Samples. A large number of surgical samples of normal squamous cell tissue in the anatomical vicinity of a suspected SCC. The protein containing fractions are purified and the amount of Oncoseq protein present in each is obtained as described in Example 16. The ratios of the amount of Oncoseq protein to the amount of reference protein are calculated for each sample and the average value for normal samples is obtained.

b. Primary Tumor Samples. The same process is followed as for part a, except that the surgical samples are samples of demonstrated primary SCCs. The ratios are calculated and the average value for primary tumor samples is obtained.

c. Metastatic Tumor Samples. The same process is followed as for part a, except that the surgical samples are samples of metastasized SCCs. The ratios are calculated and the average value for metastasized carcinoma samples is obtained.

Example 22

Diagnosis of, Prognosis of, and Therapeutic Strategy for, Squamous Cell Carcinoma Patients A surgical sample of a suspected squamous cell carcinoma and of adjacent normal squamous cell tissue is obtained from a patient suspected of suffering from the carcinoma. The samples are separately treated to determine the normalized amount Oncoseq protein in each sample, as described in Example 16. The adjacent normal sample serves as a control, and should reproduce the average normal values found in Example 17, within expected statistical variation. The suspected carcinoma sample is evaluated, and the resulting value is compared to the normal average value, the primary tumor average value and the metastatic tumor value obtained using the procedures described in Example 17. The value found for the surgical sample is ascribed to being either a normal value, a value characteristic of a primary tumor, or a value characteristic of a metastatic tumor, within an acceptable statistical level of significance. Based on the result, a contribution has been made to the diagnosis of the cancer, and to the prognosis of the cancer in the patient. Additionally, the result can contribute to establishing a course of therapy to pursue among a choice of such therapies. For example, in addition to surgical resection, choices may include radiation therapy or chemotherapy, and, within chemotherapy, a choice among various chemotherapeutic agents.

Example 23

Clinical significance of 3q Amplification

A FISH probe was developed for the analysis of paraffin embedded section from the three YAC clones representing the apex of duplication in chromosome 3q. After confirming the efficacy of the probe, the analysis was applied to 29 paraffin embedded samples from normal mucosa, 20 samples of dysplasia/carcinoma in situ, and 50 samples from invasive cancers. Overall, duplication at 3q was encountered in 1 of 29 cases (3%) of normal mucosa, 5 of 20 dysplasia/carcinoma in situ (25%), and 28 of 50 invasive carcinomas (56%) ($p<0.001$). Duplication at 3q26.3 was exclusively seen in tissues derived from the peritumoral milieu. The increasing prevalence of 3q duplication in progressing from normal mucosa to premalignant tissue, and then to invasive cancer is consistent with the findings of Heselmeyer and colleagues (Heselmeyer K, et al. (997) Genes Chromosomes Cancer; 19:233-40; Heselmeyer K, et al. (1996) Proc Natl Acad Sci USA; 93:479-84)1 that 3q duplication is a transition event in the progression to invasive SCC.

Samples from the same patient for each differentiation category were present in 18 cases. Among these samples, duplication at 3q was found in 6% of normal mucosa, 26% of dysplasia/in situ carcinoma, and 67% of invasive cancers ($p=0.04$). Local recurrences developed in four patients in this group, all occurring in cases with 3q duplication identified in non-cancerous mucosal margins ($p=0.002$). The higher rates of local recurrence in 5 cases (80%) with 3q duplication in non-cancerous tissues from surgical margins was striking, lending further support to the role of 3q duplication as a marker for cancer progression.

The samples of invasive cancer were derived from a population with a median age (64 years) and gender distribution (66% males) representative of that seen in the general patient population with head and neck SCC. The majority of cases originated in the oral cavity (84%), with all but 1 of these being oral tongue lesions. Overall, 27 patients (54%) had early stage (I or II) lesions. The pathological differentiation of the tumors were well, moderate, and poor in 8%, 86% and 6%, respectively. Treatment consisted of surgery alone in 64%, radiation therapy alone in 10%, and surgery followed by adjuvant radiation in 26% of cases. N1 or N2 nodal metastasis was present in 19 patients (38%), of which 6 (32%) had pathological evidence for extracapsular extension. In cases of invasive carcinoma, low-level (3-4 copies) and high-level duplication (>4 copies) occurred in 18 and 10 patients, respectively. The median age, gender distribution, anatomical location, TNM stage, and treatment utilized did not vary by the 3q copy number status. Similarly, the tumor differentiation, presence of extra-nodal spread, and primary treatment modality also did not vary by the 3q copy number status.

The median follow-up for the entire population was 82.5 months. The presence of locoregional recurrence increased with increasing 3q copy number, from 32% for patients with normal copy number, to 72% for low-level duplication, and 90% for high-level duplication ($p=0.003$). The number of patients dying of cancer was also correlated with the 3q copy number, increasing from 14% for normal copy number, to 44% for low-level duplication, and to 70% for high-level duplication, respectively ($p=0.006$). The three-year disease-free and cause-specific survivals negatively correlated with 3q copy number status. Multivariate analysis including factors found to be significant predictors of outcome on univariate analysis (3q status, TNM stage, and type of treatment) showed that only the presence of high level duplication at 3q was a significant predictor of disease-free survival (Model $X^2$=10.15; df=3; p=0.02) with a relative risk of 5.1 (95% CI=1.87-13.89; p=0.001) and low level duplication had a relative risk of 2.2 (95% CI=0.87-5.55; p=0.1). Similarly, multivariate analysis revealed only high-level duplication to be a significant predictor of cause-specific survival (Model $X^2$ 10.03; df=3; p=0.02) with a relative risk of 7.6 (95% CI=1.94-29.62; p=0.004), while low-level duplication had a relative risk of 3.0 (95% CI=0.80-11.32; p=0.1).

Example 24

Immunogenic Peptides Using a Hydrophobicity Plot

Figure 17:
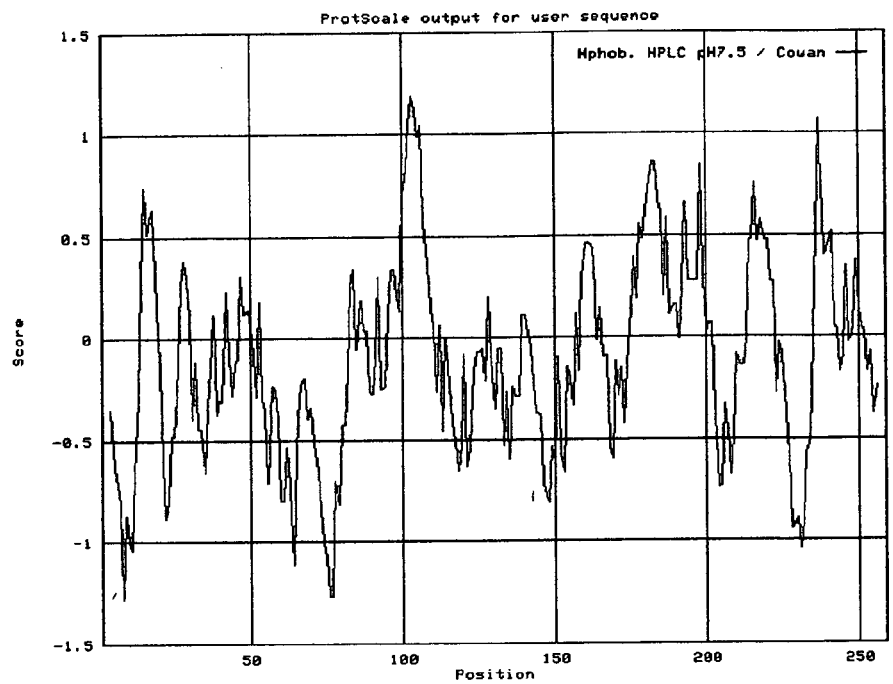
FIG. 17. Residue plot of hydrophobicity score for Oncoseq according to the Cowan-Whittaker method.

The development of a monoclonal antibody is envisioned to permit characterization of Oncoseq. To this end immunogenic peptides for use in immunizing mice are identified. Individual peptides 18-27 residues in length, drawn from 3-5 different regions of Oncoseq are identified, using the Cowan-Whittaker method (Peptide Research 3:75-80 (1990)). This method is based on hydrophobicity indices at pH 7.5 determined by HPLC. The hydrophobicity plot obtained by applying this method to the Oncoseq polypeptide is shown in FIG. 17. Sequences are specifically selected for their uniqueness and immunogenic potential. These sites contain the most hydrophilic regions that are in the region of turns and are not predicted to contain a glycosylation site.

Peptides are synthesized and purified for antibody development. Mice are injected subcutaneously with keyhole limpet hemocyanin conjugated with a chosen peptide or peptides, emulsified in Titer Max. Sera are obtained and screened by ELISA for a response to the peptides. Splenocytes from the mice possessing the highest anti-peptide response are fused with polyethylene glycol to SP2/O-Ag14 cells. Culture supernatants from the hybridomas are then screened by ELISA for secretion of anti-Oncoseq specific antibodies. Positive supernatants are then screened by immunoprecipitation, immunofluorescence, western blot analysis, and immunohistochemical reactivity with Oncoseq. Positive clones are sub-cloned twice by limiting dilution, generated in large quantities and used for subsequent studies.

Example 25

Immunogenic Peptides Using a Beta Turn Potential Plot

Figure 18:
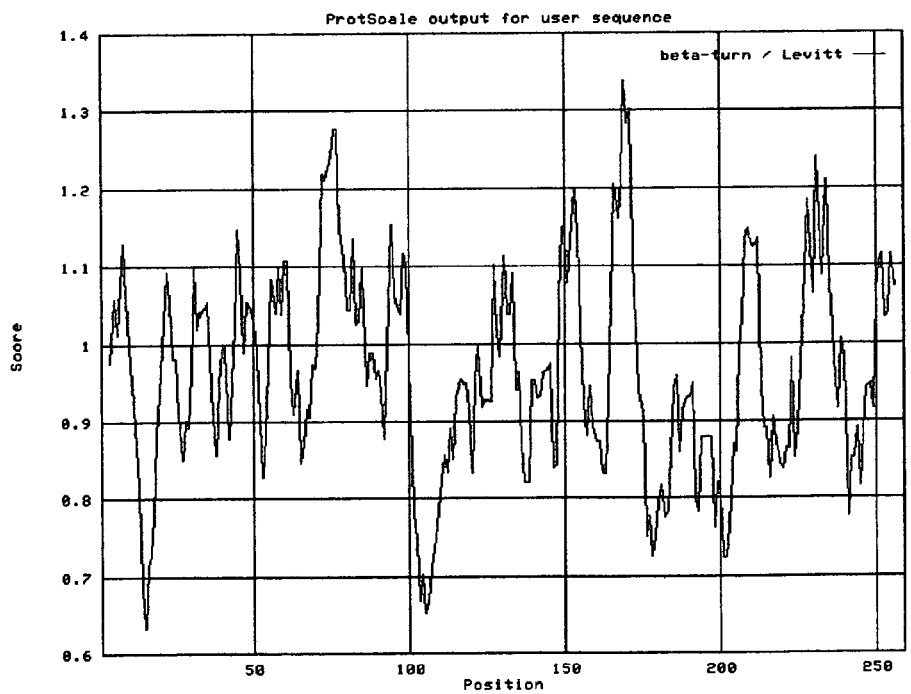
FIG. 18. Residue plot of beta turn score for Oncoseq according to the Levitt method.

Immunogenic peptides are identified and developed using methods similar to those in Example 24. Individual peptides 18-27 residues in length, drawn from 3-5 different regions of Oncoseq are identified, using the Levitt method to identify beta turn potential (Biochemistry 17:4277-4285 (1978)). The beta turn plot obtained by applying this method to the Oncoseq polypeptide is shown in FIG. 18. Sequences are specifically selected for their uniqueness and immunogenic potential. These sites are in the region of turns and are not predicted to contain a glycosylation site.

We claim:

1. An isolated polynucleotide comprising a nucleotide sequence encoding the polypeptide of SEQ ID NO:4 or a full complement thereto.

2. The polynucleotide described in claim 1 wherein the nucleotide sequence comprises positions 16-795 of SEQ ID NO:3 or its full length complement.

3. The polynucleotide described in claim 1 wherein the polynucleotide is a RNA.

4. The polynucleotide described in claim 1 wherein the polynucleotide is a DNA.

5. A vector comprising the polynucleotide sequence described in claim 1.

6. The vector described in claim 5 wherein the polynucleotide sequence is operably linked to provide for expression of the encoded polypeptide.

7. An isolated host cell comprising the vector described in claim 4.

8. A method of preparing the polypeptide of SEQ ID NO:4 comprising culturing a host cell comprising the vector described in claim 6 under conditions suitable for expression of the polypeptide, and isolating the polypeptide.

9. A composition comprising the polynucleotide of claim 1 and a pharmaceutically acceptable carrier.

10. A kit comprising the polynucleotide described in claim 1 placed within a container.

11. The polynucleotide of claim 1 further comprising a second polynucleotide sequence encoding a polypeptide label joined to the nucleotide sequence encoding the polypeptide of SEQ ID NO:4.

* * * * *